(12) United States Patent
Burn et al.

(10) Patent No.: US 8,598,350 B2
(45) Date of Patent: Dec. 3, 2013

(54) BRANCHED MATERIALS FOR PHOTOVOLTAIC DEVICES

(75) Inventors: Paul Leslie Burn, Kenmore (AU); Byeong-Kwan An, Oxford (GB); Paul Meredith, Brisbane (AU); Michael Gardner Deceglie, Fairfax, VA (US)

(73) Assignee: Isis Innovation Limited, Oxford (GB)

( * ) Notice: Subject to any disclaimer, the term of this patent is extended or adjusted under 35 U.S.C. 154(b) by 391 days.

(21) Appl. No.: 12/738,735

(22) PCT Filed: Oct. 17, 2008

(86) PCT No.: PCT/GB2008/003545
§ 371 (c)(1),
(2), (4) Date: Oct. 27, 2010

(87) PCT Pub. No.: WO2009/050492
PCT Pub. Date: Apr. 23, 2009

(65) Prior Publication Data
US 2011/0056561 A1     Mar. 10, 2011

(30) Foreign Application Priority Data

Oct. 19, 2007   (GB) .................................. 0720553.7

(51) Int. Cl.
*C07F 15/00* (2006.01)
*H01L 51/00* (2006.01)

(52) U.S. Cl.
USPC .............................. 546/2; 313/504; 313/506

(58) Field of Classification Search
USPC ...................................... 546/2; 313/504, 506
See application file for complete search history.

(56) References Cited

U.S. PATENT DOCUMENTS

2007/0017569 A1    1/2007  Gui et al.

FOREIGN PATENT DOCUMENTS

| EP | 1 622 178 | 2/2006 |
|----|-----------|--------|
| WO | WO 2004/009679 | 1/2004 |
| WO | WO 2004/009679 A2 | 2/2004 |

OTHER PUBLICATIONS

Kimura, M., et al, "Energy transfer within ruthenium-cored rigid metallodendrimers," Tetrahedron Letters 41 (2000) 6809-6813.
Ceroni, P., et al, "Luminescence as a tool to investigate dendrimer properties," Prog. Polym. Sci. 30 (2005) 453-473.
Satoh, N., et al, "Dye-sensitized solar cell using [pi]-conjugated dendrimer," Journal of Photopolymer Science & Technology, vol. 9, No. 2 (2006) 141-142.
Galoppini, E., "Linkers for anchoring sensitizers to semiconductor nanoparticles," Coordination Chemistry Reviews 248 (2004) 1283-1297.
International Search Report for PCT/GB2008/003545, mailed Apr. 16, 2009.
Kimura et al., "Energy transfer within ruthenium-cored rigid metallodendrimers", *Tetrahedron Letters*, vol. 41, No. 35, Aug. 1, 2000, pp. 6809-6813, XP004213954.
Ceroni et al., "Luminescence as a tool to investigate dendrimer properties", *Progress in Polymer Science*, vol. 30, No. 3-4, Mar. 1, 2005, pp. 453-473, XP004856621.
Satoh et al., "Dye-sensitized solar cell using [pi]-conjugated dendrimer", *Journal of Photopolymer Science and Technology*, vol. 19, No. 2, Aug. 15, 2006, pp. 141-142, XP008102028.
Gallopini, "Linkers for anchoring sensitizers to semiconductor nanoparticles", *Coordination Chemistry Reviews*, vol. 248, No, 13-14, Jul. 1, 2004, pp. 1283-1297, XP004578920.

*Primary Examiner* — Charanjit Aulakh
(74) *Attorney, Agent, or Firm* — Nixon & Vanderhye P.C.

(57) ABSTRACT

The invention provides a dye-sensitized photovoltaic device which comprises: a first electrode; a second electrode; and, disposed between the first and second electrodes: an electron acceptor material which comprises a semiconductive metal oxide, a redox mediator material, and a photosensitizing dye which comprises a dendrimer of formula (I): $[X]_m$-CORE-$[[Y]_p$-$[DENDRON]]_n$ wherein n, m, p, CORE, DENDRON, X and Y are as defined herein. The invention further provides a photosensitizing dye which is a dendrimer of formula (I), and the use, as a photosensitizing dye in a dye-sensitized photovoltaic device, of a compound which is a dendrimer of formula (T). Novel dendrimers of formula (T) are also provided. Novel catechol-based compounds are also provided. The catechol-based compounds can be used together with the dendrimers of formula (T) as the photosensitizing dyes in a photovoltaic device. Accordingly, the invention further provides photosensitizing dyes and dye-sensitized photovoltaic devices comprising such catechol compounds, and the use of such catechol compounds as photosensitizing dyes in a dye-sensitized photovoltaic device.

11 Claims, 16 Drawing Sheets

US 8,598,350 B2

BRANCHED MATERIALS FOR PHOTOVOLTAIC DEVICES

This application is the U.S. national phase of International Application No. PCT/GB2008/003545 filed 17 Oct. 2008 which designated the U.S. and claims priority to GB Patent Application No. 0720553.7 filed 19 Oct. 2007, the entire contents of each of which are hereby incorporated by reference.

FIELD OF THE INVENTION

The present invention relates to dye-sensitized photovoltaic devices having, between two electrodes, an electron acceptor material comprising a semiconducting metal oxide, a photosensitizing dye and a redox mediator material.

BACKGROUND TO THE INVENTION

Nanostructured $TiO_2$ dye-sensitized solar cells (DSSCs) have been intensively investigated in the past decade as a promising renewable energy source. In such DSSCs, the dye sensitizer is one of the key components for high solar-to-electrical energy conversion efficiency. Thus, considerable effort has been made in developing photovoltaic sensitizers with high power conversion efficiencies. Until now, simple heteroleptic Ru(II) complexes with anchoring groups have achieved power conversion efficiencies over 11% in standard AM 1.5 sunlight. These efficiencies exceed those of other competitive "low cost-medium efficiency" technologies such as thin film amorphous silicon, cadmium telluride, copper indium gallium selenide, etc., but as yet cannot compete with the standard high efficiency polycrystalline or monocrystalline silicon cells (15-22%) or indeed the new high efficiency compound semi-conductor technologies based upon gallium arsenide (>30%). Besides Ru complexes, metal free organic dyes have also been utilised in DSSCs, and have thus far achieved power conversion efficiencies of over 9% under AM 1.5 G irradiation.

These simple structured Ru(II) complexes and organic small molecules are, however, not fully satisfactory for commercial outdoor device applications because, although high power conversion efficiencies can be observed initially, devices comprising such compounds exhibit poor device stability under long-term light exposure, volatile liquid electrolyte evaporation or leaking and thermal stress. For practical outdoor device applications, long-term device stability at high temperatures (e.g. ca. 80° C.) is an essential requirement in addition to high photoelectric conversion efficiency. There is therefore a continuing need to provide high performance DSSC sensitizers which not only provide high conversion efficiency but also facilitate long-term device stability.

SUMMARY OF THE INVENTION

It is a finding of the present invention that certain dendritic opto-electronic materials can be used as dye sensitizers in DSSCs, and are suitable for providing good power conversion efficiencies and improved device stabilities. Without wishing to be bound by theory, the branched structure of the dendrimers is thought to give rise to improved device performance by reducing intermolecular interactions and minimising dye aggregation. Furthermore, the hydrophobicity of the dendritic sensitizers is thought to prevent penetration of the redox mediator material (for instance, an electrolyte) onto the metal oxide material, thereby (a) reducing or preventing desorption of the sensitizer from the from the metal oxide surface and (b) retarding backward electron transfer from the metal oxide conduction band to the redox mediator material. The dendritic sensitizers show excellent thermal stability and mechanical strength owing to the rigidity of the dendritic structure. In addition, the materials may be synthesised from building blocks which extend the pi-conjugation length of the dye sensitizer, thereby improving light harvesting capacity.

Accordingly, in one aspect the invention provides a dye-sensitized photovoltaic device which comprises:
a first electrode;
a second electrode; and, disposed between the first and second electrodes:
   (a) an electron acceptor material which comprises a semiconductive metal oxide;
   (b) a redox mediator material; and
   (c) a photosensitizing dye which comprises a dendrimer of formula (I):

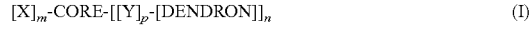

wherein
   n is an integer from 1 to 6;
   m is an integer from 1 to 6;
   each p is independently either 0 or an integer from 1 to 5
   CORE is non-polymeric organic group, a metal atom or metal ion, or a group which comprises a metal atom or metal ion, wherein CORE provides at least (n+m) points of attachment, each of said (n+m) points of attachment being bonded to one X, Y or DENDRON group;
   each DENDRON is the same or different and represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups;
   —[Y]$_p$— is a linking group bonded to CORE and terminating in a single bond to the first branching group of DENDRON, wherein each Y is the same or different and is selected from aryl, heteroaryl, vinyl, acetylenyl, $C_{1-15}$ alkylene and $C_{1-15}$ alkyleneoxy groups; and
   each X, which is the same or different, is an anchoring group which is (a) other than DENDRON, and (b) attached to said semiconductive metal oxide.

In another aspect, the invention provides the use, as a photosensitizing dye in a dye-sensitized photovoltaic device, of a compound which is a dendrimer of formula (I):

wherein
   n is an integer from 1 to 6;
   m is an integer from 1 to 6;
   each p is independently either 0 or an integer from 1 to 5;
   CORE is non-polymeric organic group, a metal atom or metal ion, or a group which comprises a metal atom or metal ion, wherein CORE provides at least (n+m) points of attachment, each of said (n+m) points of attachment being bonded to one X, Y or DENDRON group;
   each DENDRON is the same or different and represents an at least partially conjugated dendritic molecular structure comprising at least one branching group and optionally at least one linking group, the branching groups being selected from aryl and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups;

—$[Y]_p$— is a linking group bonded to CORE and terminating in a single bond to the first branching group of DENDRON, wherein each Y is the same or different and is selected from aryl, heteroaryl, vinyl, acetylenyl, $C_{1-15}$ alkylene and $C_{1-15}$ alkyleneoxy groups; and each X, which is the same or different, is an anchoring group which is (a) other than DENDRON, and (b) capable of attachment to a semiconductive metal oxide.

In another aspect, the invention provides a photosensitizing dye which comprises a dendrimer of formula (I) as defined above.

In another aspect, the invention provides a compound which is a dendrimer of formula (I):

$$[X]_m\text{-CORE-}[[Y]_p\text{-[DENDRON]}]_n \quad (I)$$

wherein n is an integer from 1 to 6;

m is an integer from 1 to 6;

each p is independently either 0 or an integer from 1 to 5;

CORE is a metal atom or a metal ion or a group which comprises a metal atom or metal ion, wherein CORE provides at least (n+m) points of attachment, each of said (n+m) points of attachment being bonded to one X, Y or DENDRON group;

each DENDRON is the same or different and represents an at least partially conjugated dendritic molecular structure comprising at least one branching group and optionally at least one linking group, the branching groups being selected from aryl and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups;

—$[Y]_p$— is a linking group bonded to CORE and terminating in a single bond to the first branching group of DENDRON, wherein each Y is the same or different and is selected from aryl, heteroaryl, vinyl, acetylenyl, $C_{1-15}$ alkylene and $C_{1-15}$ alkyleneoxy groups; and each X, which is the same or different, is an anchoring group which is (a) other than DENDRON, and (b) capable of attachment to a semiconductive metal oxide.

It is a further finding of the present invention that other, non-dendritic dye sensitizer compounds can be used together with the dendrimer sensitizer compounds of formula (I) in a dye-sensitized photovoltaic device. In particular, the present invention provides a novel class of catechol-based sensitizers which can be used together with the dendrimer sensitizers of formula (I).

Accordingly, in another aspect, the present invention provides a compound of formula (VII):

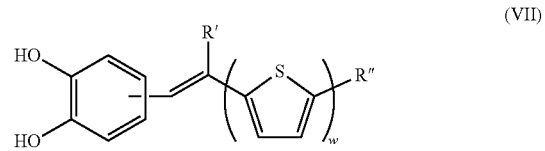

(VII)

wherein R' is H or CN; w is an integer of 2 to 5; and R" is H, unsubstituted or substituted $C_{1-15}$ alkyl or DENDRON, wherein DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

The invention further provides a photosensitizing dye which comprises a compound of formula (VII) as defined above.

The invention further provides the use of a compound of formula (VII) as defined above as a photosensitizing dye in a dye-sensitized photovoltaic device.

The invention further provides a dye-sensitized photovoltaic device which comprises a first electrode; a second electrode; and, disposed between the first and second electrodes: (a) an electron acceptor material which comprises a semiconductive metal oxide; (b) a redox mediator material; and (c) a photosensitizing dye which comprises a compound of formula (VII) as defined above.

DETAILED DESCRIPTION OF THE INVENTION

Figure 1:
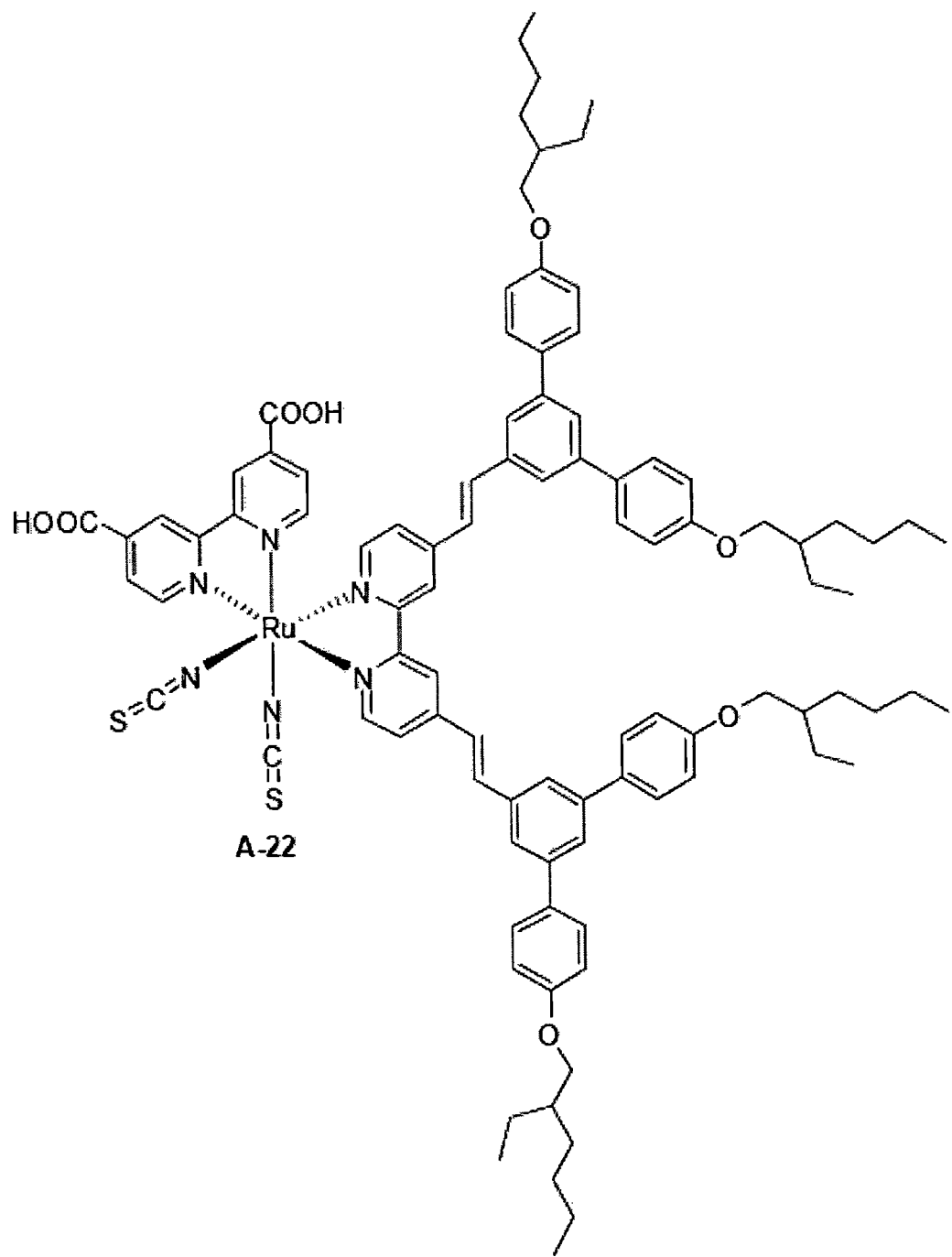
FIG. 1 shows the chemical structure of a dye sentitizer compound of the invention, A-22.
Figure 2:
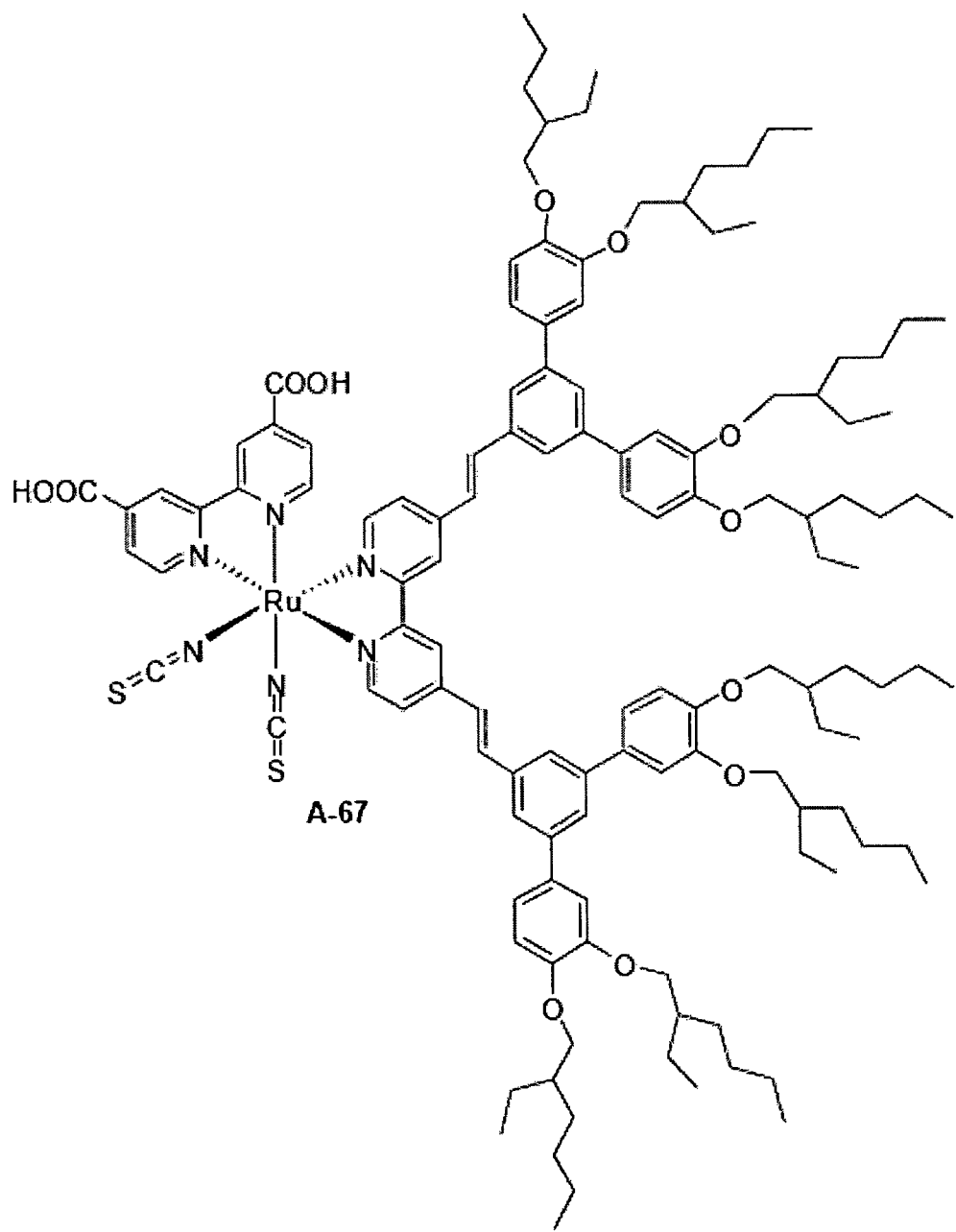
FIG. 2 shows the chemical structure of a dye sentitizer compound of the invention, A-67.
Figure 3:
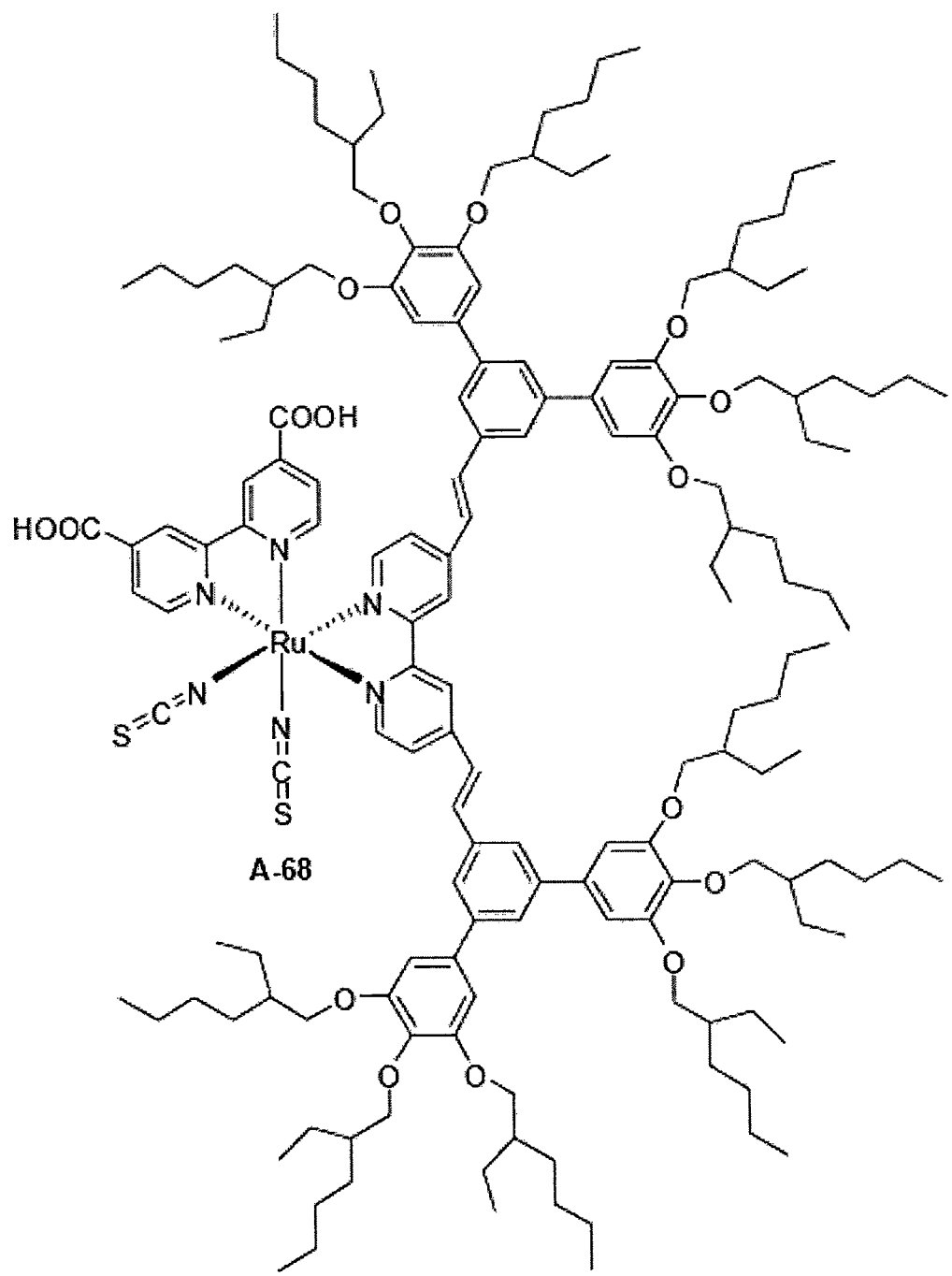
FIG. 3 shows the chemical structure of a dye sentitizer compound of the invention, A-68.

Dye-sensitized photovoltaic devices according to the present invention comprise an electron acceptor material, a photosensitizing dye and a redox mediator material, all of which are disposed between a first electrode and a second electrode. The first and second electrodes are an anode and a cathode, one or both of which is transparent to allow the ingress of light. The electron acceptor material comprises a semiconductive metal oxide. Typically, the dye-sensitized photovoltaic device is a dye-sensitized solar cell (DSSC).

The electron acceptor material may be any n-type, or electron transporting, semiconductive metal oxide. Typically, the electron acceptor material comprises a film or a layer of said semiconductive metal oxide. Usually, the metal oxide film is disposed on a surface of one of the electrodes. Typically, the electrode on which the metal oxide film is disposed is a transparent indium tin oxide (ITO), F-doped tin oxide or F-doped indium tin oxide (F-ITO) working electrode. The semi-conductive metal oxide is usually an oxide of a d-block metal or an oxide of an f-block metal, or an oxide of an element of the third main group. Typically, the semi-conductive metal oxide is usually an oxide of a d-block metal. More typically, the semiconductive metal oxide is titania. The titania may be mesoporous titania. The use of a mesoporous titania film in dye-sensitized photovoltaic cells significantly increases the cross section of light harvesting by the photosensitizing dye while maintaining good contact with the redox mediator material. Typically, the electron acceptor material comprises porous titania. As used herein "porous titania" means mesoporous titania or nanoporous titania, as opposed to dense or "solid" $TiO_2$. Mesoporous and nanoporous titania contains pores with diameters in the nanometer scale, and can be formed synthetically, for example by sintering together titania nanocrystals, as is described in by K. M Coakley et al., *Chem. Mater.* 2004, 16, 4533-4542. Layers of such nanoporous titania can be deposited using doctor blade coating techniques or any other liquid coating application technique, for instance spin coating, dip coating, screen printing and ink jet printing, all of which are well known to the skilled person. The use of nanocrystalline titania ($TiO_2$) has been shown to be particularly advantageous. The term "nanocrystalline", as used herein, means that the semiconductive metal oxide, in particular $TiO_2$, is in polycrystalline form with a granularity of the order of several nanometers, for example 10 to 50 nanometers. The semiconductive metal oxide may be structured or templated with a defined pore geometry or shape. In one embodiment, the electron acceptor material comprises said semiconductive metal oxide disposed on metal posts. Typically, the semiconductive metal oxide is titania. Alternatively, the semiconductive metal oxide can be another metal oxide which has a wide band gap, for instance zinc oxide.

The redox mediator material may be any suitable material which is capable of returning the oxidized sensitizer to its ground state by electron donation to the oxidized sensitizer. Thus, the redox mediator material may be any suitable electrolyte, hole transporter material or ionic transport material. The redox mediator material may be in the solid, liquid or gas phase. More usually, however, the redox mediator material is in the solid or liquid phase.

Typically, the redox mediator material is an electrolyte. The electrolyte may be a liquid electrolyte, a gel type electrolyte or a polyelectrolyte. Among suitable electrolytes are those including a redox system consisting of a mixture of at least one electrochemically active salt and at least one molecule designed to form an oxidation-reduction system with either the anion or cation of the said salt. Typically, said electrochemically active salt of the electrolyte has a melting point below ambient temperature, or forms with the aforesaid molecule a phase with a melting point below ambient temperature. Thus, typically, the electrolyte is an ionic liquid electrolyte. Such electrolytes have been described in EP0737358. Alternatively, the electrolyte may be a quasi-solid state electrolyte, i.e. a gel. Such electrolytes are described in EP1087412. Typically, the electrolyte comprises iodide/triiodide ($I^-/I_3^-$) as a redox couple. More typically, the electrolyte is an ionic liquid which comprises iodide/triiodide ($I^-/I_3^-$) as a redox couple.

In one embodiment, the redox mediator material is a hole transporter material. Typically, the hole transporter material is neutral. Typically, the hole transporter material is in the solid state. However, liquid and gas (particularly liquid) hole-transporter materials are also envisaged. The hole transporter material may be any suitable p-type or hole-transporting, semiconducting material. It may be inorganic or organic, a conjugated polymer or a small molecule. Suitable hole transporter materials include those used in OLEDs; a broad range of such hole transporter materials is well known to the skilled person.

In one embodiment, the hole transporter material comprises a dendrimer. Typically, the dendrimer is solution processable. The dendrimer may comprise one or more surface groups which are specifically designed to be complementary to the photosensitizing dye.

The choice of the first and second electrodes of the photovoltaic devices of the present invention may depend on the structure type. Typically the semiconductive metal oxide is deposited onto indium-tin oxide (ITO), more typically onto F-doped ITO, which are transparent materials. Thus, the first electrode is usually transparent and typically comprises ITO. More typically, the first electrode comprises F-doped ITO. However, transparent conducting polymers, such as PAT (polyaniline) or PEDOT can also be used. Usually, the second electrode comprises a high work function metal, for instance gold, silver, nickel, palladium or platinum, and typically platinum. Usually, the metal is deposited onto a conductive substrate, for instance conducting glass, by sputtering or vapour deposition as appropriate. Thus, more typically, the second electrode (or "counter electrode") is a platinum-sputtered conducting glass electrode. The high work function metal may also be deposited from solution using standard techniques and materials (for example colloidal platinum) and may also be porous or structured to increase the total surface area for charge exchange.

The metal oxide layer is sensitized by at least one chromophoric substance, known as the photosensitizing dye, or dye sensitizer. One method of sensitising is where the photosensitizing dye absorbs a photon to produce an excited state, which efficiently transfers its electron into the conduction band of the semiconductive metal oxide (usually $TiO_2$). The oxidized sensitizer is subsequently restored by electron donation from the redox mediator material, for instance from an iodide/triiodide redox couple in an electrolyte. The injected electron flows through the semiconductor network to arrive at the back electrode, and then flows through the external load to the counter electrode. At the counter electrode, in turn, reduction of the redox mediator material (typically an electrolyte) completes the circuit. In the case of an iodide/triiodide electrolyte, reduction of triiodide regenerates iodide, to complete the circuit. Thus, in the photovoltaic devices of the invention, ultrafast electron injection from a photoexcited dye into the conduction band of an oxide semiconductor, subsequent dye regeneration and electron transport to the counter electrode, are responsible for the efficient generation of electricity.

The photosensitising dyes employed in the devices of the present invention are dendrimers of formula (I) as defined above. Such dendrimers, which typically comprise rigid aromatic segments and bulky alkyl or alkoxy chains, are good candidates for addressing the following issues simultaneously: (i) improving light harvesting capacity; (ii) minimising dye aggregation; (iii) retarding a backward electron transfer from the conduction band of the semiconductive metal oxide (typically $TiO_2$) to the redox mediator material (typically, to triiodide), (iv) preventing dye desorption from the surface of the semiconductive metal oxide by the penetration of redox mediator material (e.g. a liquid ionic electrolyte), and (v) enhancing the thermal stability of the dye. Indeed, the dendrimers of formula (I) are found to have the following distinctive advantages over simple structured (or linear type) sensitizers: (a) simple building blocks which facilitate extension of the pi-conjugation lengths as desired (possible solution for (i)), (b) effective reduction of intermolecular interactions due to the branched structures (possible solution for (ii)), (c) high hydrophobicity, usually as a result of peripheral bulky alkyl chains (possible solution for (iii) and (iv)), and (d) excellent thermal stability and mechanical strength owing to the rigidity of the aromatic dendrons (possible solution for (v)).

The photosensitive dye is chromophoric. Thus, the dendrimers of formula (I) must include at least one chromophore, i.e. a chemical group which is chromophoric. Typically, the CORE group of the dendrimers of formula (I) is or comprises a chromophore. Alternatively, or in addition, one or more of the DENDRON groups may be, or comprise, a chromophore. There may be more than one chromophore within the molecule, for example all DENDRON groups may be chromophoric, or all moieties within the molecule may be chromophoric. The chromophores may all be in the same area of the compound, for example all chromophores may be present on a single DENDRON, with other parts of the molecule, e.g. CORE being non-chromophoric. Alternatively, the chromophores may all be in the CORE. The optical properties of the or each chromophore can be manipulated by appropriate design of the compound. For example, the length of the chromophore can be manipulated in order to achieve different optical properties.

The following definitions apply to the compounds defined herein, including the dendrimer compounds of formula (I):

As used herein, the term "dendrimer" represents a structure such as the structure of formula (I) having a core and a number of dendrons attached to the core.

As used herein, the phrase "at least partially conjugated" means that at least a portion of the dendron is made up of alternating double and/or triple, and single bonds or lone pairs, apart from the surface groups. Preferably all the dendrons or branching structures are made up of alternating single or double bonds or lone pairs; such a structure being termed a conjugated dendron. However this does not mean that the π system is fully delocalised. The delocalisation of the π system is dependent on the regiochemistry of the attachments.

As used herein the term "distal" means the part or parts of the molecule furthest from the core when following the bond sequence out from the core. It will be appreciated that due to the geometry of the bonds and moieties within a dendron a distal unit may be closer in space to the core than an earlier moiety in the dendron. The distal aryl and/or heteroaryl groups which may terminate the dendritic molecular structures described herein may be substituted, for example by one or more surface groups described below.

As used herein the term acetylenyl refers to acetylenyl groups that are divalent, vinyl refers to vinyl groups that are di- or trivalent, and aryl or heteroaryl refers to aryl or heteroaryl groups that are mono-, di-, tri- or multivalent.

It is to be understood that the term "metal ion" or "metal cation", as used herein, describes the charge state the metal would have without any ligands attached (the oxidation state). Typically, in the dendrimers of the invention that contain a metal cation the overall charge of the dendrimer is neutral and the metal-ligand bonding will have more or less covalent character depending on the metal and ligand involved.

As used herein the term $C_{1-15}$ alkyl is an unsubstituted or substituted linear or branched alkyl group or moiety containing from 1 to 15 carbon atoms such as a $C_{1-8}$ alkyl group or moiety or a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different. When an alkyl group is substituted it typically bears one or more (typically, one, two or three) substituents selected from substituted or unsubstituted $C_{1-20}$ alkyl, substituted or unsubstituted aryl (as defined herein), cyano, amino, $C_{1-10}$ alkylamino, di($C_{1-10}$)alkylamino, arylamino, diarylamino, arylalkylamino, amido, acylamido, hydroxy, oxo, halogen, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid, phosphonate ester and cyclic ether.

As used herein, a $C_{2-15}$ alkenyl group or moiety is a linear or branched alkenyl group or moiety containing from 2 to 15 carbon atoms respectively such as a $C_{2-8}$ alkenyl group or moiety or a $C_{2-4}$ alkenyl group or moiety. For the avoidance of doubt, where two or more alkenyl moieties are present in a group, the alkenyl moieties may be the same or different.

As used herein, a halogen is typically chlorine, fluorine, bromine or iodine. It is preferably chlorine, fluorine or bromine.

As used herein the term amino represents a group of formula —NH$_2$. The term $C_{1-15}$ alkylamino represents a group of formula —NHR' wherein R' is a $C_{1-15}$ alkyl group, preferably a $C_{1-15}$ alkyl group, as defined previously. The term di($C_{1-15}$)alkylamino represents a group of formula —NR'R" wherein R' and R" are the same or different and represent $C_{1-15}$ alkyl groups, preferably $C_{1-6}$ alkyl groups, as defined previously. As used herein the term amido represents a group of formula —C(O)NH$_2$.

As used herein the term aryl refers to $C_{6-14}$ aryl groups which may be mono- or polycyclic, such as phenyl, naphthyl and fluorenyl. An aryl group may be unsubstituted or substituted at any position. Unless otherwise stated, it carries 0, 1, 2 or 3 substituents. Preferred substituents on an aryl group include halogen, $C_{1-15}$ alkyl, $C_{2-15}$ alkenyl, —C(O)R wherein R is hydrogen or $C_{1-15}$ alkyl, —CO$_2$R wherein R is hydrogen or $C_{1-15}$ alkyl, hydroxy, $C_{1-15}$ alkoxy, $C_{2-15}$ alkenyloxy, $C_{1-15}$ alkylthio, $C_{2-15}$ alkenylthio, $C_{1-6}$ haloalkyl, $C_{2-15}$ haloalkenyl, $C_{1-15}$ haloalkoxy, $C_{2-15}$ haloalkenyloxy, amino, $C_{1-15}$ alkylamino, di($C_{1-15}$)alkylamino, $C_{6-14}$ aryloxy, —O$_2$SR wherein each R is the same or different and represents $C_{1-15}$ alkyl or $C_{2-15}$ alkenyl, —SiR$_3$ wherein each R is the same or different and represents hydrogen, $C_{1-15}$ alkyl or $C_{2-15}$ alkenyl, $C_{6-14}$ arylthio, $C_{6-14}$ aryl and 5- to 10-membered heteroaryl, and wherein the substituents are themselves unsubstituted or substituted. When the substituents are themselves substituted, suitable substituents on the substituents include 1, 2, 3 or 4 groups selected from $C_{1-15}$ alkyl, $C_{2-15}$ alkenyl, $C_{1-15}$ alkoxy, $C_{2-15}$ alkenyloxy, hydroxy and halogen. Particularly suitable are 1 or 2 groups selected from $C_{1-8}$ alkyl, $C_{2-8}$ alkenyl, $C_{1-8}$ alkoxy and $C_{2-8}$ alkenyloxy. In particular, when an aryl group is substituted by a $C_{6-14}$ aryl group or by a 5- to 10-membered heteroaryl group, these substituents are themselves unsubstituted or substituted by one or more substituents selected from $C_{1-15}$ alkyl, $C_{2-15}$ alkenyl, $C_{1-15}$ alkoxy and $C_{2-15}$ alkenyloxy. When an aryl group is substituted by groups other than $C_{6-14}$ aryl groups or 5- to 10-membered heteroaryl groups, the substituents are themselves preferably unsubstituted.

As used herein, a heteroaryl group is typically a 5- to 14-membered aromatic ring, such as a 5- to 10-membered ring, more preferably a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, triazinyl, thiazolyl, imidazolyl, pyrazolyl, oxazolyl, isothiazolyl, benzofuranyl, isobenzofuranyl, benzothiophenyl, indolyl, indazolyl, carbazolyl, acridinyl, purinyl, cinnolinyl, quinoxalinyl, naphthyridinyl, benzimidazolyl, benzoxazolyl, quinolinyl, quinazolinyl and isoquinolinyl.

When the heteroaryl group is a monocyclic heteroaryl group, preferred groups include thiophenyl, pyrrolyl, pyridyl, imidazolyl, triazinyl and triazolyl.

As used herein, references to a heteroaryl group include fused ring systems in which a heteroaryl group is fused to an aryl group. When the heteroaryl group is such a fused heteroaryl group, preferred examples are fused ring systems wherein a 5- to 6-membered heteroaryl group is fused to one or two phenyl groups. Examples of such fused ring systems are benzofuranyl, isobenzofuranyl, benzopyranyl, cinnolinyl, carbazolyl, benzotriazolyl, phenanthridinyl, benzothiophenyl, indolyl, indazolyl, benzimidazolyl, benzoxazolyl, quinolinyl, quinazolinyl and isoquinolinyl moieties.

A heteroaryl group may be unsubstituted or substituted at any position. Unless otherwise stated, it carries 0, 1, 2 or 3 substituents. Preferred substituents on a heteroaryl group include those listed above in relation to aryl groups. When a heteroaryl group is substituted by a $C_{6-14}$ aryl group or by a 5- to 10-membered heteroaryl group, these substituents are themselves unsubstituted or substituted by one or more substituents selected from $C_{1-15}$ alkyl, $C_{2-15}$ alkenyl, $C_{1-15}$ alkoxy and $C_{2-15}$ alkenyloxy. When a heteroaryl group is substituted by groups other than $C_{6-14}$ aryl groups or 5- to 10-membered heteroaryl groups, the substituents are themselves preferably unsubstituted.

As used herein, an alkoxy group is typically a said alkyl group attached to an oxygen atom. Similarly, alkenyloxy groups and aryloxy groups are typically a said alkenyl group or aryl group respectively attached to an oxygen atom. An alkylthio group is typically a said alkyl group attached to a thio group. Similarly, alkenylthio groups and arylthio groups are typically a said alkenyl group or aryl group respectively attached to a thio group. A haloalkyl or haloalkoxy group is typically a said alkyl or alkoxy group substituted by one or more said halogen atoms. Typically, it is substituted by 1, 2 or 3 said halogen atoms. Haloalkyl and haloalkoxy groups include perhaloalkyl and perhaloalkoxy groups such as —$CX_3$ and —$OCX_3$ wherein X is a said halogen atom, for example chlorine or fluorine, as well as longer alkyl and/or alkoxy chains such as $C_{2-6}$ chains substituted by one or more halogen atoms.

Haloalkenyl and haloalkenyloxy groups are, by analogy, typically a said alkenyl or alkenyloxy group substituted by one or more said halogen atoms. Typically, it is substituted by 1, 2 or 3 said halogen atoms.

A $C_{1-15}$ alkylene group is an unsubstituted or substituted bidentate moiety obtained by removing two hydrogen atoms, either both from the same carbon atom, or one from each of two different carbon atoms, of a hydrocarbon compound having from 1 to 15 carbon atoms (unless otherwise specified), which may be aliphatic or alicyclic, and which may be saturated, partially unsaturated, or fully unsaturated. Thus, the term "$C_{1-15}$ alkylene" includes the sub-classes $C_{2-15}$ alkenylene, $C_{2-15}$ alkynylene, and cycloalkylene, etc. Typically it is $C_{1-10}$ alkylene, for instance $C_{1-6}$ alkylene. Typically it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be unsubstituted or substituted, for instance, as specified above for alkyl. Examples of linear saturated $C_{1-6}$ alkylene groups include, but are not limited to, —$(CH_2)_n$— where n is an integer from 1 to 6, for example, —$CH_2$— (methylene), —$CH_2CH_2$— (ethylene), —$CH_2CH_2CH_2$— (propylene), and —$CH_2CH_2CH_2CH_2$— (butylene).

A $C_{1-15}$ alkyleneoxy group is an unsubstituted or substituted bidentate moiety comprising a $C_{1-15}$ alkylene group bonded to an oxygen atom, i.e. —O—($C_{1-15}$ alkylene)- or —($C_{1-15}$ alkylene)-O—. Examples of linear saturated $C_{1-6}$ alkyleneoxy groups include, but are not limited to, —O—$(CH_2)_n$— where n is an integer from 1 to 6, for example, —O—$CH_2$—, —O—$CH_2CH_2$—, —O—$CH_2CH_2CH_2$—, and —O—$CH_2CH_2CH_2CH_2$—. A specific example of a larger alkyleneoxy group is the group —O-2-ethylhexyl.

As used herein, the term "hydroxyl group" represents a group of formula —OH. As would be understood by the skilled person, the hydroxyl group may be an acidic hydroxyl group (an acidic —OH group). The term "acidic hydroxyl group" or "acidic —OH group" as used herein, is a group which is capable of dissociating to some extent in water to form $H^+$ (i.e. $H_3O^+$) ions and the conjugate base moiety —$O^-$, such that the pH of the solution is below 7. Examples of acidic hydroxyl groups include the —OH groups of carboxylic acids, phosphonic acid, sulfonic acid, phenol or catechol.

As used herein, the terms "carboxyl" and "carboxylic acid" each represent a group of the formula: —C(=O)OH, or —COOH. As would be understood by the skilled person, a carboxylic acid group (for instance, when employed in the present invention as group which is attached or attachable to the semiconductive metal oxide) can exist in protonated and deprotonated forms (for instance, —C(=O)OH and —C(=O)$O^-$).

As used herein, the term "salt of a carboxylic acid" means a salt comprising the carboxylate anion, —$COO^-$, and a counter cation. Typically, the salt is of the formula —C(=O)$O^-Z^+$, wherein $Z^+$ is a monovalent cation. Typically, $Z^+$ is an alkali metal cation or a cationic alkaline earth metal monohydroxide. Thus, $Z^+$ may be $Na^+$, $K^+$, $[CaOH]^+$ or $[MgOH]^+$, for instance.

As used herein, the term "phosphonic acid" represents a group of the formula: —P(=O)(OH)$_2$. As would be understood by the skilled person, a phosphonic acid group (for instance, when employed in the present invention as a group which is attached or attachable to the semiconductive metal oxide) can exist in protonated and deprotonated forms (for example, —P(=O)(OH)$_2$, —P(=O)($O^-$)$_2$ and —P(=O)(OH)($O^-$)).

As used herein, the term "salt of a phosphonic acid" means a salt comprising the anion —P(=O)($O^-$)$_2$ or —P(=O)(OH)($O^-$) and a counter cation. Typically, the salt is of the formula —[P(=O)(OH)($O^-$)]$Z^+$, —[P(=O)($O^-$)$_2$].$2Z^+$ or —[P(=O)($O^-$)$_2$]$Z^{2+}$, wherein $Z^+$ is a monovalent cation and $Z^{2+}$ is a dication. Typically, $Z^+$ is an alkali metal cation or a cationic alkaline earth metal monohydroxide. Thus, $Z^+$ may be $Na^+$, $K^+$, $[CaOH]^+$ or $[MgOH]^+$, for instance. Typically, $Z^{2+}$ is an alkaline earth metal dication. Thus, $Z^{2+}$ may be $Ca^{2+}$ or $Mg^{2+}$, for example.

As used herein, the term "sulfonic acid" represents a group of the formula: —S(=O)$_2$OH. As would be understood by the skilled person, a sulfonic acid group (for instance, when employed in the present invention as a group which is attached or attachable to the semiconductive metal oxide) can exist in protonated and deprotonated forms (for example, —S(=O)$_2$OH and —S(=O)$_2O^-$).

As used herein, the term "salt of a sulfonic acid" means a salt comprising the anion —S(=O)$_2O^-$ and a counter cation. Typically, the salt is of the formula —S(=O)$_2O^{-Z+}$, wherein $Z^+$ is a monovalent cation. Typically, $Z^+$ is an alkali metal cation or a cationic alkaline earth metal monohydroxide. Thus, $Z^+$ may be $Na^+$, $K^+$, $[CaOH]^+$ or $[MgOH]^+$, for instance.

As used herein, the term "a catechol group" refers to any group which comprises an unsubstituted or substituted benzene-1,2-diol moiety. As would be understood by the skilled person, a catechol group (for instance, when employed in the present invention as a group which is attached or attachable to the semiconductive metal oxide) can exist in protonated and deprotonated forms (for example, -Ph(OH)$_2$, -Ph(OH)(O$^-$) and -Ph(O$^-$)$_2$). Similarly, a hydroxyl group of an aryl or heteroaryl group in which a ring carbon atom of said aryl or heteroaryl group is substituted with the hydroxyl group, can exist in protonated or deprotonated form (i.e. as —Ar—OH and —Ar—O$^-$). A salt of such an aryl or heteroaryl group means a salt comprising the anion —Ar—O$^-$ and a counter cation, which is typically a monovalent cation, for instance an alkali metal cation, usually Na$^+$ or K$^+$. Similarly a salt of a catechol group means a salt which comprises a group comprising (a) the unsubstituted or substituted anionic moiety -Ph(OH)(O$^-$) or (b) the unsubstituted or substituted anionic moiety -Ph(O$^-$)$_2$, and a counter cation. The counter cation is typically an alkali metal cation or an alkaline earth metal cation. Thus, the counter cation may be Na$^+$, K$^+$, Ca$^{2+}$ or Mg$^{2+}$, for instance.

The term "d-block metal" as used herein means any one of the three series of elements arising from the filling of the 3d, 4d and 5d shells, and situated in the periodic table following the alkaline earth metals. Thus, the term "d-block metal", as used herein, includes for instance Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd and Hg. Accordingly, the d-block metal in the complexes of the invention is typically selected from Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd and Hg.

Typically, in the dendrimers of formula (I), n is 1, 2, 3 or 4. More typically, n is 2.

Typically, in the dendrimers of formula (I), m is an integer of 1 to 4. More typically, m is 2, 3 or 4. Even more typically, m is 2.

As noted above, CORE is non-polymeric organic group, a metal atom or metal ion, or a group which comprises a metal atom or metal ion, wherein CORE provides at least (n+m) points of attachment, each of said (n+m) points of attachment being bonded to one X, Y or DENDRON group.

When the core is a non-polymeric organic group it can be a chromophore (e.g. a conjugated group) or non-luminescent. Examples of cores which can be incorporated as chromophores include aryl and heteroaryl groups such as fluorenes, naphthalenes and porphyrin and perylene rings. As used herein, "non-polymeric" means that the core is not a polymeric group, although it may be in the form or a dimer, trimer or oligomer, or may be macrocyclic. When the core is in the form of an oligomer consisting of a number of units, it will preferably contain eight or fewer units. Suitable units are single aryl or heteroaryl groups (e.g. a single fluorene unit). When it is a dimer, trimer or oligomer, it may comprise more than one such aryl or heteroaryl group, which are the same or different, bonded together and optionally substituted. Where the core comprises more than one aryl or heteroaryl group (i.e. more than one "(hetero)aryl" group) each (hetero)aryl group may be linked to another of said (hetero)aryl groups by a single bond or by a suitable linking group. Suitable linking groups include unsubstituted or substituted vinyl groups or acetylenyl groups. The said (hetero)aryl groups may be linked together in this way to form a dimer, trimer, oligomer or macrocycle. Thus, in one embodiment, the core comprises a cyanine group. Other suitable cores include difluorene, trifluorene and biphenyl groups as well as other combinations of single aryl and/or heteroaryl groups such as phenyl and thiophenyl. Examples of non-luminescent cores include aryl-substituted alkyl groups, such as tetraphenylmethane.

While these are only examples of suitable groups it will be appreciated that a huge number of similar groups can function as cores provided they are capable of provides at least (n+m) points of attachment, each of said (n+m) points of attachment being bonded to one X, Y or DENDRON group.

Typically, the core is a metal atom or metal ion, or a group which comprises a metal atom or metal ion. Typically, in this embodiment, CORE comprises a metal cation and attached ligands; i.e. the ligands form part of the core itself. Typically, therefore, CORE comprises a metal complex, which metal complex comprises a metal atom or metal ion and one or more ligands. Typically, the metal atom or metal ion is a metal cation.

Suitable metals include:
lanthanide metals: such as cerium, samarium, europium, terbium, dysprosium, thulium, erbium and neodymium;
d-block metals, especially those in rows 2 and 3, that is, elements 39 to 48 and 72 to 80, such as iridium, platinum, rhodium, osmium, ruthenium, rhenium, scandium, chromium, manganese, iron, cobalt, nickel and copper; and
main group metals of the Periodic Table, such as metals from Groups IA, IIA, IIB, IIIB e.g. lithium, beryllium, magnesium, zinc, aluminum, gallium and indium.

Typically, the metal is selected from Ru, Fe, Os, Ir and Zn. Even more typically, M is Ru. Usually, M is Ru(II).

The metal is typically near the centre of the core and the core is typically a chromophoric. If it is not chromophoric one or more of the dendrons should contain a chromophore. It is preferred that the metal ion chromophore is sited at the core of the molecule, because then it will be relatively isolated from the core chromophores of adjacent molecules, which minimizes possible concentration quenching or triplet-triplet annihilation. The atoms or groups coordinating/binding to the metal typically form part of the core itself.

Typically, when the core is a metal atom or metal ion, or a group which comprises a metal atom or metal ion, the metal atom or metal ion is not bonded directly to the first branching group of the or each DENDRON.

Typically, CORE comprises a metal complex, which metal complex comprises a metal atom or metal ion and one or more ligands, wherein the or each X group is bonded to a ligand of said metal complex and the or each DENDRON or, where present, the or each Y group, is bonded to a ligand of said metal complex. More typically, CORE comprises a metal complex, which metal complex comprises a metal atom or metal ion, a first ligand and a second ligand, wherein the or each X group is bonded to said first ligand and the or each DENDRON or, where present, the or each Y group, is bonded to said second ligand.

Preferred ligands which coordinate/bind to the metal include mono-, bi- and tri-dentate ligands, with bidentate ligands being preferred. Particular mention can be made of bidentate ligands which comprise a carbocyclic ring (which acts as a carbon donor) and/or a heterocyclic ring (which acts as a heteroatom donor, preferably a nitrogen donor). The carbocyclic rings may be chosen from aryl groups, for example phenyl. The heterocyclic rings may be chosen from heteroaryl groups, for example pyridine. Typically, the ligand is a bidentate ligand which comprises two nitrogen-containing heterocyclic rings, for instance pyridyl rings. The heterocyclic rings are preferably directly linked by a single bond, for example as shown in a preferred ligand, 2,2'-bipyridine.

The or each DENDRON or Y group and the or each X group, may be bound to a carbocyclic or heterocyclic ring of such a bidentate ligand. Furthermore, the DENDRON, Y or X group may be bound to any position of the heterocyclic ring, although for six-membered ring systems it is preferred that the DENDRON, Y or X group is bound to either the meta- or para-position relative to the bond between the heterocyclic ring and the metal. Typically, the or each X group is bonded to a first such bidentate ligand and the or each DENDRON or, where present, the or each Y group, is bonded to a second such bidentate ligand.

In one embodiment, the dendrimer is a metal complex of formula (II):

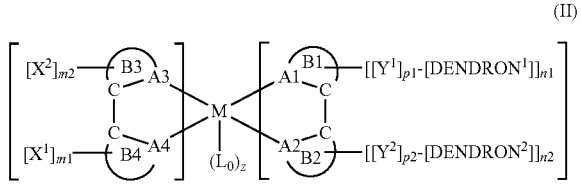

wherein
M is a metal atom or metal ion;
each of A1, A2, A3 and A4, which are the same or different, is independently selected from carbon and nitrogen;
each of B1, B2, B3 and B4, which are the same or different, is independently an aryl or heteroaryl ring which is unsubstituted or substituted and optionally fused to one or more other aryl or heteroaryl rings;
each DENDRON$^1$ and each DENDRON$^2$, which are the same or different, represents an at least partially conjugated dendritic molecular structure comprising at least one branching group and optionally at least one linking group, the branching groups being selected from aryl and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups;
—[$Y^1$]$_{p1}$— is a linking group bonded to a ring atom of B1 and terminating in a single bond to the first branching group of DENDRON$^1$, wherein each $Y^1$ is the same or different and is selected from aryl, heteroaryl, vinyl, acetylenyl, $C_{1-15}$ alkylene and $C_{1-15}$ alkyleneoxy groups;
p1 is 0 or an integer of 1 to 5;
n1 is 0, 1 or 2;
—[$Y^2$]$_{p2}$— is a linking group bonded to a ring atom of B2 and terminating in a single bond to the first branching group of DENDRON$^2$, wherein each $Y^2$ is the same or different and is selected from aryl, heteroaryl, vinyl, acetylenyl, $C_{1-15}$ alkylene and $C_{1-15}$ alkyleneoxy groups;
p2 is 0 or an integer of 1 to 5;
n2 is 0, 1 or 2;

(n1+n2) is not zero;
each $X^1$ and each $X^2$, which are the same or different, is an anchoring group which is (a) other than DENDRON$^1$ and other than DENDRON$^2$, and (b) attached to said semiconductive metal oxide;
m1 is 0 or an integer of 1 to 3;
m2 is 0 or an integer of 1 to 3;
(m1+m2) is not zero;
z is 0, 1, 2, 3 or 4; and
the or each $L_0$, where present, is a ligand.

M may be any of the suitable metals referred to above. Typically, M is a d-block metal. More typically, M is selected from Ru, Fe, Os, Ir and Zn. Even more typically, M is Ru. Usually, M is Ru(II).

Typically, each of B1, B2, B3 and B4 is independently selected from six-membered aryl and five- or six-membered heteroaryl rings. Typically, the six-membered aryl ring is phenyl and the five- or six-membered heteroaryl ring is a nitrogen-containing heteroaryl ring. More typically, each of B1, B2, B3 and B4 is independently selected from pyridyl and phenyl. Even more typically, the bidentate ligands comprising B1, B2, B3 and B4 are selected from 2-phenylpyridine and 2,2'-bipyridine.

Usually, B1 and B2 are both pyridyl rings and B1 and B2 together form a bipyridine ligand. Typically, the ligand comprising B1 and B2 is a 2,2'-bipyridine ligand wherein the nitrogen atoms of the 2,2'-bipyridine ligand is bonded to M. Typically, therefore, A1 and A2 are both N. In one embodiment, each of B1, B2, B3 and B4 is a pyridyl ring, thus, both of the bidentate ligands are bipyridyl ligands. Typically, thees two bidentate ligands are both 2,2'-bipyridine ligands wherein the nitrogen atoms of the 2,2'-bipyridine ligands are bonded to M. Typically, therefore, each of A1, A2, A3 ad A4 is N.

Typically, n1 and n2 are both 1. Usually, m1 and m2 are both 1.

Typically, z is 0, 1 or 2. More typically, z is 2.

Typically, the overall charge of the metal complex of formula (II) is neutral. Typically, the metal complex of formula (II) additionally comprises further ligands, $L_0$, which are typically of a different structure from the bidentate ligands comprising B1, B2, B3 and B4. The number of further ligands $L_0$ present and their charges will depend on the metal, M and its oxidation state. As the skilled person will appreciate, the ligands $L_0$ make up the coordination sphere of the metal, such that there is sufficient ligand binding to complete the coordination sphere of the metal.

Typically, z is 2, such that the metal complex of formula (II) additionally comprises two further groups, $L_0$, which are the same or different, each of which is bonded to the metal centre wherein each $L_0$ is a monodentate ligand or wherein both $L_0$ ligands together form a bidentate ligand. Usually, each $L_0$ is a monodentate ligand. More typically, each $L_0$ is a monodentate, monoanionic ligand. Typically, M is Ru(II).

Typically, therefore, M is Ru(II) and the metal complex of formula (II) further comprises two $L_0$ groups, both of which are bonded to said Ru(II), wherein each $L_0$, which is the same or different, is a monodentate ligand or both $L_0$ groups together form a bidentate ligand. In one embodiment, both $L_0$ groups are isothiocyanate ligands.

In one embodiment the dendrimer is a metal complex of formula (III):

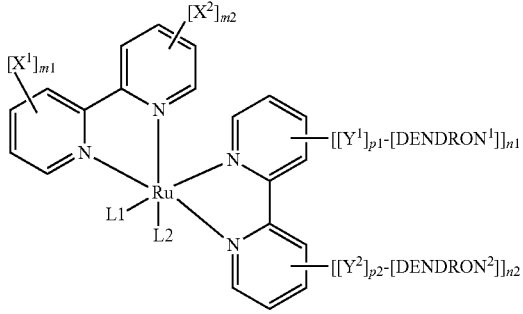

(III)

wherein
X¹, m1, X², m2, Y¹, p1, Y², p2, DENDRON¹, n1, DENDRON² and n2 are as defined above for the metal complex of formula (II); and each of L1 and L2, which are the same or different, is a monodentate ligand or L1 and L2 together form a bidentate ligand.

Usually, each of L1 and L2 is a monodentate, monoanionic ligand. In one embodiment, L1 and L2 are both isothiocyanate ligands.

As noted above, each DENDRON, DENDRON¹ or DENDRON² is the same or different and represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups. Where branching groups are described as being bonded to three or more groups, the latter can be branching or linking groups, or can be the aryl and/or heteroaryl rings which terminate the dendritic molecular structure. Where linking groups are described as being bonded to two groups, the latter can be branching or linking groups, or can be the aryl and/or heteroaryl rings which terminate the dendritic molecular structure.

The branching groups are selected from aryl and heteroaryl groups. These groups are selected because they form groups which are at least trivalent and which are hence capable of bonding to three or more groups. One of said groups to which a branching group is bonded will be a branching or linking group of the previous generation, or the CORE of the dendrimer or a Y group. The other two or more groups will be linking groups and/or branching groups of the next generation, or the aryl and/or heteroaryl groups which terminate the dendritic molecular structure.

When a branching group is an aryl group, suitable groups include phenyl, naphthalene, anthracene and, where appropriate, substituted variations. Typically, when a branching group is an aryl group it is a phenyl ring. More typically the branching group is a phenyl ring coupled at ring positions 1, 3 and 5. Thus, typically the branching group is a group of the following formula:

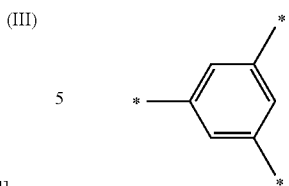

wherein one of said asterisks "*" represents a point of attachment to a branching or linking group of the previous generation, or the CORE of the dendrimer or a Y group, and the other two of said asterisks "*" each represent a point of attachment to linking groups and/or branching groups of the next generation, or the aryl and/or heteroaryl groups which terminate the dendritic molecular structure.

When a branching group is a heteroaryl group, suitable groups include pyridine, carbazolyl, triazole, triazine and, where appropriate, substituted variations. Typically, the heteroaryl group is selected from unsubstituted or substituted carbazolyl, triazole, and triazine. Carbazolyl and triazinyl are preferred. Carbazolyl is particularly preferred.

Thus, typically the branching group is a group of the following formula:

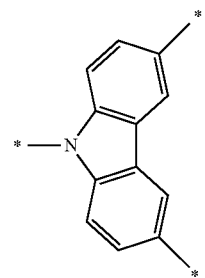

wherein the asterisk "*" at the nitrogen atom represents a point of attachment to a branching or linking group of the previous generation, or the CORE of the dendrimer or a Y group, and the other two of said asterisks "*" each represent a point of attachment to linking groups and/or branching groups of the next generation, or the aryl and/or heteroaryl groups which terminate the dendritic molecular structure.

Usually, the branching groups are selected from (a) aryl groups and (b) heteroaryl groups other than pyridyl. Thus, typically, the branching groups are selected from (a) aryl groups and (b) heteroaryl groups other than heteroaryl groups which comprise a six-membered heteroaryl ring, which six-membered heteroaryl ring contains only one ring nitrogen atom. Even more typically, the branching groups are selected from aryl groups, carbazolyl groups, triazole groups and triazinyl groups. Even more typically, the branching groups are selected from aryl groups, carbazolyl groups and triazinyl groups. Even more typically, the branching groups are selected from (a) aryl groups and (b) heteroaryl groups which comprise a 5-membered heteroaryl ring. Even more typically, the branching groups are selected from (a) aryl groups and (b) heteroaryl groups which comprise a 5-membered nitrogen-containing heteroaryl ring. Even more typically, the branching groups are selected from aryl groups and carbazolyl groups.

In one embodiment, the branching groups are selected from (a) aryl groups and (b) heteroaryl groups which do not contain any ring nitrogen atoms.

The branching groups are unsubstituted or substituted. Suitable substituents include those listed below as solubilising groups, and also those listed below as cross-linkable groups. It is preferred that the branching groups are not substituted by solubilising groups. Preferred branching groups are phenyl groups that do not have solubilising groups attached.

The linking groups of DENDRON are selected from aryl, heteroaryl, vinyl, acetylenyl and $C_{1-15}$ alkyleneoxy groups. The linking groups are chosen because they are able to form divalent moieties which are capable of bonding to two groups. The groups to which said linking groups are bonded include other linking groups, branching groups and/or the aryl and/or heteroaryl groups which terminate the dendritic molecular structure.

When a linking group is an aryl group, suitable groups include $C_{6-14}$ aryl groups such as phenyl, naphthalenyl, anthracenyl, fluorenyl and, where appropriate, substituted variations. Usually, when a linking group is an aryl group it is a phenyl or fluorenyl group. When the linking group is a phenyl ring, it is preferably coupled at ring positions 1 and 4. When the linking group is a fluorenyl ring, it is preferably coupled at ring positions 2 and 7. When a linking group is a heteroaryl group, suitable groups include pyridine, oxadiazole, thiophene and, where appropriate, substituted variations. Preferred heteroaryl linking groups include thiophene and pyridine.

The linking groups are unsubstituted or substituted. Suitable substituents include those listed below for surface groups, and also those listed below as cross-linkable groups. When a linking group is aryl, it is preferably an unsubstituted phenyl, or a fluorenyl which is unsubstituted or substituted by 1 or 2 surface groups at the 9-position. Preferred substituents for the fluorenyl group include 1 or 2, preferably 2, substituents selected from $C_{1-15}$ alkyl, $C_{1-15}$ alkoxy, $C_{1-15}$ haloalkyl, $C_{6-14}$ aryl. Alternatively, the two substituents on the 9-position of the fluorenyl group can together complete a 5- to 7-membered ring, such as a carbocyclyl ring. Preferably when a linking group is aryl it is unsubstituted phenyl or unsubstituted or substituted fluorenyl.

More than one of the moieties described as linking groups above can couple together to form larger linking groups. For example, a phenyl ring and a further phenyl ring can couple to form a biphenyl group which can itself be a linking group between two branching groups or between a branching group and an aryl or heteroaryl ring which terminates the dendritic molecular structure.

The dendritic molecular structure terminates at its distal points in aryl and/or heteroaryl groups. Typical such aryl and/or heteroaryl groups are as follows. Typical aryl groups include $C_{6-14}$ aryl groups, such as a group selected from phenyl, fluorenyl and naphthyl, typically phenyl or fluorenyl, more typically phenyl. Typical heteroaryl groups include, 5- to 10-membered heteroaryl groups containing, within the ring, one, two or three heteroatoms selected from oxygen, sulphur and nitrogen. Exemplary heteroaryl groups include groups selected from pyridyl, thiophenyl, benzamidazolyl, carbazolyl, pyrimidinyl, pyrazinyl, pyridazinyl, quinolinyl, isoquinolinyl, quinoxalinyl, benzothiophenyl, phthalazinyl, quinazolinyl, imidazolyl, pyrazolinyl, oxazolinyl, oxadiazolinyl, triazolyl, triazinyl, thiadiazolyl, benzimidazolyl, benzoxazolyl, phenanthridinyl, furyl and benzothiophenyl. Preferably these aryl and/or heteroaryl groups are substituted by one or more surface groups defined below.

Typically, each DENDRON is the same or different and represents an at least partially conjugated dendritic molecular structure comprising at least one branching group and optionally at least one linking group, the branching groups being selected from aryl groups and heteroaryl groups, and the linking groups being selected from aryl, heteroaryl, vinyl and acetylenyl groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

Typically, each DENDRON, DENDRON¹ or DENDRON² is a group of formula (IV):

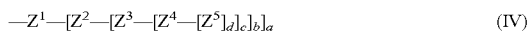

$$—Z^1—[Z^2—[Z^3—[Z^4—[Z^5]_d]_c]_b]_a \qquad (IV)$$

wherein
$Z^1$ is a branching group which is selected from aryl and heteroaryl;
a is an integer from 2 to 5;
$Z^2$ is a group of formula $-(L^2)_e$-$B^2$, wherein:
  e is 0 or an integer from 1 to 5;
  each $L^2$, which is the same or different, is a linking group which is selected from aryl, heteroaryl, vinyl, acetylenyl and $C_{1-15}$ alkyleneoxy groups; and
  $B^2$ is a branching group or, when b is 0, a terminal group, which branching or terminal group is selected from aryl and heteroaryl groups;
b is 0 or an integer from 2 to 5;
$Z^3$ is a group of formula $-(L^3)_f$-$B^3$, wherein:
  f is 0 or an integer from 1 to 5;
  each $L^3$, which is the same or different, is a linking group which is selected from aryl, heteroaryl, vinyl, acetylenyl and $C_{1-15}$ alkyleneoxy groups; and
  $B^3$ is a branching group or, when c is 0, a terminal group, which branching or terminal group is selected from aryl and heteroaryl groups;
c is 0 or an integer from 2 to 5;
$Z^4$ is a group of formula $-(L^4)_g$-$B^4$, wherein:
  g is 0 or an integer from 1 to 5;
  each $L^4$, which is the same or different, is a linking group which is selected from aryl, heteroaryl, vinyl, acetylenyl and $C_{1-15}$ alkyleneoxy groups; and
  $B^4$ is a branching group or, when d is 0, a terminal group, which branching or terminal group is selected from aryl and heteroaryl groups;
d is 0 or an integer from 2 to 5;
$Z_5$ is a group of formula $-(L^5)_h$-$T^5$, wherein:
  h is 0 or an integer from 1 to 5;
  each $L^5$, which is the same or different, is a linking group which is selected from aryl, heteroaryl, vinyl, acetylenyl and $C_{1-15}$ alkyleneoxy groups; and
  $T^5$ is a terminal group selected from aryl and heteroaryl groups;
provided that, when present as terminal groups, said $B^2$, $B^3$, $B^4$ or $T^5$ groups are either unsubstituted or substituted with one, two, three or four surface groups.

Preferred $Z^1$ groups and, when $B^2$, $B^3$ and $B^4$ are branching groups, preferred $B^2$, $B^3$ and $B^4$ groups, are those branching groups referred to above as being typical, usual or preferred. Similarly $T^5$ and, when $B^2$, $B^3$ and $B^4$ are branching groups, $B^2$, $B^3$ and $B^4$ are usually the preferred aryl and/or heteroaryl groups referred to above. Preferred $L^2$, $L^3$, $L^4$ and $L^5$ groups are the same as the linking groups referred to above as being typical, usual or preferred.

Typically, e, f, g and h are each independently either 0 or 1. Typically, e, f, g and h are zero. Typically, a is 2. Typically d is either 0 or 2. Typically, c is either 0 or 2. Typically b is either 0 or 2.

More typically, d is zero. More typically, d and c are both zero. Even more typically, b, c and d are all zero.

Usually, the branching groups of each DENDRON, DENDRON$^1$ or DENDRON$^2$ are selected from phenyl and carbazole groups, and wherein said terminal groups are selected from phenyl, fluorenyl and carbazole groups, more preferably phenyl and carbazole groups. Typically, the linking groups of each DENDRON, DENDRON$^1$ or DENDRON$^2$, where present, are selected from vinyl, acetylenyl, fluorenyl, thienyl or phenylene groups.

In the dendrimers of formulae (I) and (II), each of —[Y]$_p$—, —[Y$^1$]$_{p1}$— and —[Y$^2$]$_{p2}$—, is a linking group bonded to CORE and terminating in a single bond to the first branching group of DENDRON, wherein each Y is the same or different and is selected from aryl, heteroaryl, vinyl, acetylenyl, C$_{1-15}$ alkylene and C$_{1-15}$ alkyleneoxy groups.

Each linking group Y, Y$^1$ and Y$^2$ is a divalent moiety which is capable of bonding to two groups.

p is 0 or an integer of 1 to 5, as are p1 and p2. Thus, up to 5 linking groups, Y, Y$^1$ or Y$^2$ can couple together to form a larger linking group —[Y]$_p$—, —[Y$^1$]$_{p1}$— or —[Y$^2$]$_{p2}$—. For example, a phenyl ring and a further phenyl ring can couple to form a biphenyl group, or two vinyl groups can couple to form a bivinyl group. The linking groups Y, Y$^1$ and Y$^2$ are unsubstituted or substituted. Suitable substituents include those listed above for alkyl groups. Y, or each of Y$^1$ and Y$^2$, may be a C$_{2-15}$ alkenylene group. More typically, Y, or each of Y$^1$ and Y$^2$, is a vinyl group.

Typically, in the dendrimers of formula (I) each p is either 0 or 1. More typically, each p is 1. Even more typically, each p is 1 and Y is a vinyl group.

Similarly, in the dendrimers of formula (II), p1 and p2 are typically either 0 or 1. More typically, p1 and p2 are both 1. Even more typically, p1 and p2 are both 1 and Y$^1$ and Y$^2$ are each vinyl groups.

Typically, each [Y]$_p$-[DENDRON], [Y$_1$]$_{p1}$-[DENDRON$^1$] or [Y$_2$]$_{p2}$-[DENDRON$^2$] is a group of formula (VIII) or (IX), wherein R$_1$, R$_2$ and R$_3$, which are the same or different, are selected from hydrogen or a surface group as defined hereinbelow:

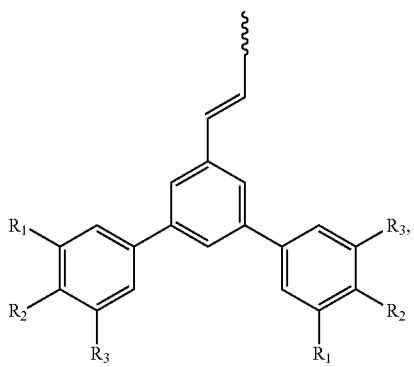

(VIII)

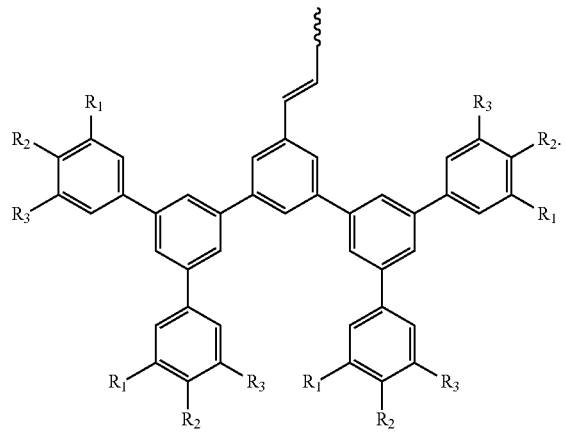

(IX)

Typically, R$_1$, R$_2$ and R$_3$ are each selected from H and —O-2-ethylhexyl. More typically, either (a) R$_2$ is —O-ethylhexyl and R$_1$ and R$_3$ are both H; (b) R$_1$ and R$_2$ are both —O-2-ethylhexyl and R$_3$ is H; or (c) R$_1$, R$_2$ and R$_3$ are each —O-2-ethylhexyl.

As used herein, the term "a group which is capable of attachment to a semiconductive metal oxide" means any group which is capable of attachment, by any suitable means, to a semiconductive metal oxide, for instance to titania, such that the molecule to which the group belongs (usually a dendrimer of formula (I)) is held to or within said semiconductive metal oxide by virtue of the attachment. Similarly, the term "a group which is attached to said semiconductive metal oxide" means any group which is attached, by any suitable means, to the semiconductive metal oxide, such that the molecule to which the group belongs (usually a dendrimer of formula (I)) is held to or within said semiconductive metal oxide.

Without wishing to be bound by theory, the attachment of the group to the semiconductive metal oxide may be through the formation of one or more chemical bonds between the group and the semiconductive metal oxide (for instance, one or more covalent bonds, ionic bonds, hydrogen bonds or other non-covalent bonds), through a physical interaction between the group and the semiconductive metal oxide (e.g. due to an electrostatic attraction between the two), or through a mechanical interaction between the two (e.g. due to mechanical interlocking). The group may facilitate adsorption of the molecule to which the group belongs to a surface of said semiconductive metal oxide, or absorption of said molecule into said semiconductive metal oxide. Typically, a chemical bond is formed between the semiconductive metal oxide and the group, thereby bonding the molecule to which the group belongs (usually a dendrimer of formula (I)) to the semiconductive metal oxide. Typically, the molecule to which the group belongs is thereby immobilized on a surface of the semiconductive metal oxide.

Typically, the anchoring group which is capable of attachment to the semiconductive metal oxide, or which is attached to said semiconductive metal oxide, X, X$^1$ or X$^2$, is a group which comprises an —OH group. Other suitable anchoring groups, X, X$^1$ or X$^2$, include groups which comprise a cyano group and chelating groups with pi-conducting character, for instance oxymes, dioxymes, hydroxyquinolines, salicylates and α-keto enolates.

When the group which is capable of attachment to the semiconductive metal oxide, or the group which is attached to said semiconductive metal oxide, X, $X^1$ or $X^2$, is a group which comprises an —OH group, the —OH group is usually an acidic —OH group. Thus, the —OH group may be an —OH group within a carboxylic acid, phosphonic acid, sulfonic acid, phenol or catechol group.

As would be understood by the skilled person, the acidic —OH group may exist in the deprotonated form, —O⁻ as well as in the protonated form —OH. Without wishing to be bound by theory, it is believed that the oxygen atom of the —OH group or the deprotonated hydroxyl group, —O⁻, bonds to the titania, thereby forming a bond between the oxygen atom of the hydroxyl group and the titania. Thus, for instance, when bonded to titania, the hydroxyl group may form an —O—[titanic] covalent linkage, for instance an O—Ti covalent bond, or an ionic bond.

The group which is capable of attachment to the semiconductive metal oxide, or the group which is attached to said semiconductive metal oxide, X, $X^1$ or $X^2$, may be a group which comprises a salt of a hydroxyl group. The terms "salt of a hydroxyl group" and "salt of an —OH group", as used herein, means a salt comprising the anion —O⁻ and a counter cation. Typically, the salt is of the formula —O⁻Z⁺, wherein $Z^+$ is a monovalent cation. Typically, $Z^+$ is an alkali metal cation or a cationic alkaline earth metal monohydroxide. Thus, $Z^+$ may be Na⁺, K⁺, [CaOH]⁺ or [MgOH]⁺, for instance.

Typically, therefore, X, $X^1$ or $X^2$ is a group which comprises an —OH group or a group which comprises a salt of an —OH group. Usually, the —OH group is an acidic —OH group.

More typically, X, $X^1$ or $X^2$ is a group which comprises: a carboxylic acid group or a salt of a carboxylic acid group; a phosphonic acid group or a salt of a phosphonic acid group; a sulfonic acid group or a salt of a sulfonic acid group; or an aryl or heteroaryl group, wherein a ring carbon atom of said aryl or heteroaryl group is substituted with a hydroxyl group, or a salt of such an aryl or heteroaryl group. Usually, X, $X^1$ or $X^2$ is a carboxylic acid group or a salt thereof, a catechol group or a salt thereof, a phenol group or a salt thereof or a phosphonic acid group or a salt thereof. More typically, X, $X^1$ or $X^2$ is a carboxylic acid group, a catechol group, a phenol group or a phosphonic acid group. Even more typically, X, $X^1$ or $X^2$ is a carboxylic acid group.

Suitable surface groups for the dendrimers, which are preferably present, and are attached to the distal aryl and/or heteroaryl groups, include branched and unbranched alkyl, especially t-butyl, branched and unbranched alkoxy, for example 2-ethylhexyloxy, hydroxy, alkylsilane, carboxy, carbalkoxy, and vinyl groups. Another suitable unbranched alkyl surface group is an n-propyl moiety. In this case, the distal aryl and/or heteroaryl groups preferably bear two such surface groups, e.g. two n-propyl groups.

Typically, therefore, one or more of said terminal aryl and/or heteroaryl groups is substituted with one, two, three or four surface groups. More typically, one or more of said terminal aryl and/or heteroaryl groups is substituted with one or two surface groups. More preferably, one or more of said terminal aryl and/or heteroaryl groups is substituted with one surface group.

Advantageously, the presence of one or more surface groups can increase the hydrophobicity of the dendrimer. This can further reduce or prevent penetration of the redox mediator material of the photovoltaic device (usually a liquid electrolyte) onto the surface of the conductive metal oxide, which in turn reduces or prevents dye desorption from the surface of the metal oxide. The use of bulky, hydrophobic surface groups can also reduce further or prevent a backward electron transfer from the conduction band of the metal oxide to the redox mediator material. Thus, the performance and stability of the device may be improved further by the use of appropriate surface groups.

Typically, the or each of said surface groups, which may be the same or different, is independently selected from a sulphur-containing or silicon-containing group; a sulphonyl group; a polyether group; a cyclic ether group; a $C_{1-15}$ alkyl (preferably a t-butyl or n-propyl group, more preferably t-butyl) group; a $C_{2-15}$ alkenyl group; an amino group; a mono-, di- or tri-($C_{1-15}$)alkylamino group; a —COOR group wherein R is hydrogen or $C_{1-15}$ alkyl; an —OR group wherein R is hydrogen, aryl, or $C_{1-15}$ alkyl or $C_{2-15}$ alkenyl (preferably —O-ethylhexyl); an —$O_2$SR group wherein R is $C_{1-15}$ alkyl or $C_{2-15}$ alkenyl; an —SR group wherein R is aryl, $C_{1-15}$ alkyl or $C_{2-15}$ alkenyl; an —$SiR_3$ group wherein the R groups are the same or different and are hydrogen, $C_{1-15}$ alkyl or $C_{2-15}$ alkenyl; an —SR' group wherein R' is aryl, $C_{1-15}$ alkyl or $C_{2-15}$ alkenyl; aryl; or heteroaryl.

The surface group can be chosen to obtain a dendrimer surface which is hydrophobic. As mentioned above a hydrophobic dendrimer surface serves to prevent the redox mediator material penetrating past the dendrimer and onto the titania electron acceptor material. Advantageously, this in turn (a) retards backward electron transfer from the metal oxide conduction band to the electrolyte; and (b) prevents dye desorption from the surface of the titania by penetration of the redox mediator material. Hence, it will be appreciated that it is preferred that the surface groups are groups which contain at least two carbon atoms, for example $C_2$-$C_{15}$ alkyl or OR where R is aryl or $C_2$-$C_{15}$ alkyl or alkenyl.

More preferably, the surface groups will contain 4 or more carbons for example tert-butyl or —O-2-ethylhexyl. In another embodiment, the surface groups on at least one of the terminal aryl or heteroaryl groups will contain a total of at least 4 or more carbon atoms. For example, a terminal aryl or heteroaryl group may bear two n-propyl groups, hence the surface groups on this terminal aryl or heteroaryl group contain 6 carbon atoms.

In addition, the surface group can be chosen such that the individual dendrimers can be crosslinked together, after they have been attached to the conductive metal oxide. Advantageously, this increases the stability of the photovoltaic device. Thus in one embodiment, the or each of said surface groups, or at least one or more of the surface groups present, is a cross-linkable group which can be cross-linked upon irradiation or by chemical reaction. Alternatively the or each of said surface groups, or at least one or more of the surface groups present, comprises a protecting group which can be removed to leave a group which can be cross-linked.

As the skilled person will appreciate, different surface groups may be present on different dendrons or different distal groups of a dendron.

Furthermore, the surface groups can be selected so the dendrimers are soluble in solvents suitable for solution processing. Indeed, it is preferred that the dendrimer is solution processable, i.e. the surface groups are such that the dendrimer can be dissolved in a solvent.

In one embodiment, the dendrimer is of the following formula (V):

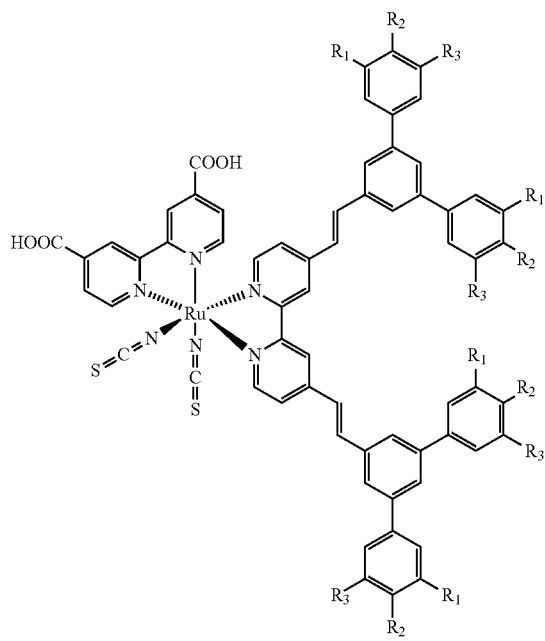

(V)

wherein:
(a) R$_2$ is —O-2-ethylhexyl and R$_1$ and R$_3$ are both H;
(b) R$_1$ and R$_2$ are both —O-2-ethylhexyl and R$_3$ is H; or
(c) R$_1$, R$_2$ and R$_3$ are each —O-2-ethylhexyl.

In another embodiment, the dendrimer is of the following formula (X):

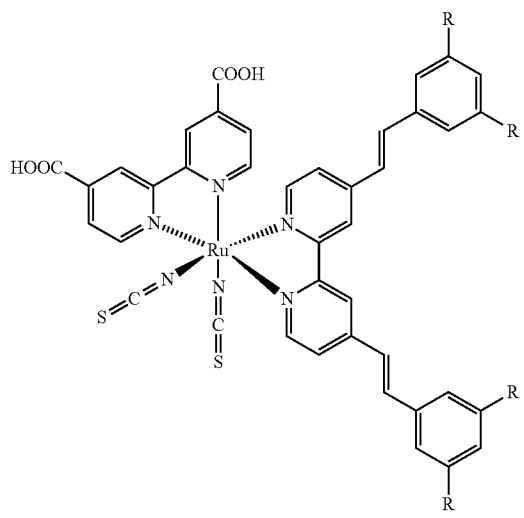

(X)

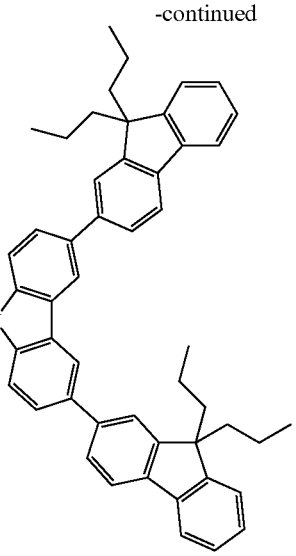

It is a further finding of the invention that the conversion efficiencies of the photovoltaic devices which comprise a photosensitive dye of formula (I) could be further enhanced by the introduction of one or more additional photosensitive dyes. Such additional dyes, which are usually smaller than the dendritic dyes, can be co-adsorbed with the dendritic dyes onto the conductive metal oxide, and could thereby further improve device performance.

Accordingly, in one embodiment, the dye-sensitized photovoltaic device of the invention comprises a second photosensitizing dye attached to said conductive metal oxide, which second photosensitizing dye is other than said dendrimer of formula (I).

The second photosensitizing dye may be any suitable photosensitizing dye which is not a dendrimer. Such dyes are well known to the skilled person, and include transition metal complexes, in particular ruthenium complexes, but also iron and osmium complexes, comprising one or more heterocyclic ligands. Such ligands include bidentate, tridentate or polydentate pyridyl-containing ligands. Dye sensitizers of this type are described, inter alfa, in EP1622178, EP0333641, EP0525070, EP0613466 and EP0758337.

In one embodiment, the second photosensitizing dye is unsubstituted or substituted benzene-1,2-diol (i.e. catechol). Usually, the benzene-1,2-diol, or catechol, is substituted at one or more of the 3, 4, 5 and 6 ring positions with a group which is conjugated with the ring. When used as a dye sensitizer in a photovoltaic device, such compounds are capable of "one-step" electron injection from the ground state of the dye to the conduction band of the semiconductive metal oxide. When the oxide is titania, this process is known as "direct dye-to-TiO$_2$ charge transfer" (DTCT).

Typically, therefore, the second photosensitizing dye is benzene-1,2-diol which is either unsubstituted or substituted in the 3, 4, 5 or 6 position with a group of formula (VI):

$$\text{-G-[J]}_j\text{-R''} \qquad (VI)$$

wherein G is unsubstituted or substituted C$_{2-6}$ alkenylene or unsubstituted or substituted C$_{1-6}$ alkyl; j is 0 or an integer of 1 to 6; each J, which is the same or different, is an unsubstituted or substituted heteroarylene group, or an unsubstituted or substituted arylene group; and R'' is H, C$_{1-15}$ alkyl, N(R''')$_3$$^+$ or DENDRON, wherein each R''', which is the same or different, is H or C$_{1-6}$ alkyl and wherein DENDRON is as defined herein. Thus, DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

More typically, in this embodiment, the second photosensitizing dye is benzene-1,2-diol which is either unsubstituted or substituted in the 3, 4, 5 or 6 position with a group of formula (VI):

$$-G-[J]_j-R'' \quad (VI)$$

wherein G is unsubstituted or substituted $C_{2-6}$ alkenylene; j is an integer of 1 to 6; each J, which is the same or different, is an unsubstituted or substituted heteroarylene group, or an unsubstituted or substituted arylene group; and R" is H, $C_{1-15}$ alkyl or DENDRON, wherein DENDRON is as defined herein.

Typically, each J, which is the same or different, is a 5- or 6-membered unsubstituted or substituted heteroarylene group, or a 5- or 6-membered unsubstituted or substituted arylene group (typically a 6-membered unsubstituted or substituted arylene group). Typically j is an integer of 1 to 5. More typically, j is an integer of 1 to 4. Even more typically, j is an integer of 1 to 3. Typically, G is a substituted $C_{2-6}$ alkenylene. More typically, G is a $C_{2-6}$ alkenylene which is substituted with a cyano group. Even more typically, G is a 2-cyanoethylene group. Typically, R" is H.

Thus, in one embodiment, the second photosensitizing dye is a compound of formula (VII):

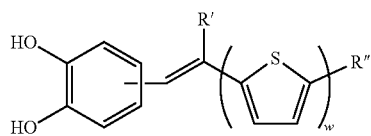

(VII)

wherein R' is H or CN; w is an integer of 1 to 6; and R" is H, $C_{1-15}$ alkyl or DENDRON, wherein DENDRON is as defined herein. Thus, DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and $C_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups. Typically, R' is CN. Typically, w is an integer of 1 to 5, more typically an integer of 1 to 4, even more typically an integer of 1 to 3. Typically, R" is H. In one embodiment, w is an integer of 2 to 5, more typically, an integer of 2 to 4, even more typically an integer of 2 or 3.

More typically, the second photosensitizing dye is any one of the following compounds:

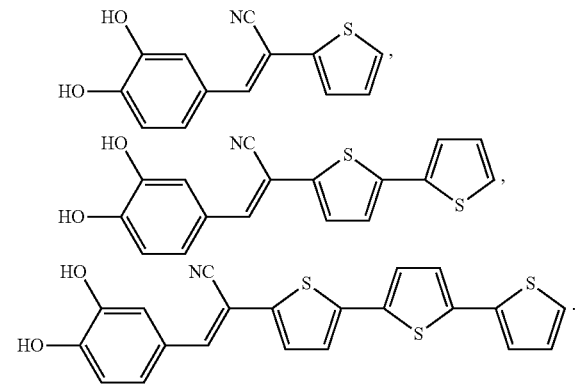

In another embodiment, the second photosensitizing dye is a Ru(II) complex, typically a heteroleptic Ru(II) complex. Heteroleptic Ru(II) complexes are known to be useful as dye sensitizers in photovoltaic cells. Usually, the heteroleptic Ru(II) complex comprises one or more 2,2' bipyridyl ligands. Complexes of this type are described inter alia, in EP1622178, EP0333641, EP0525070, EP0613466 and EP0758337. Examples of heteroleptic Ru(II) complexes which may be used as the second photosensitizing dye include the following compounds:

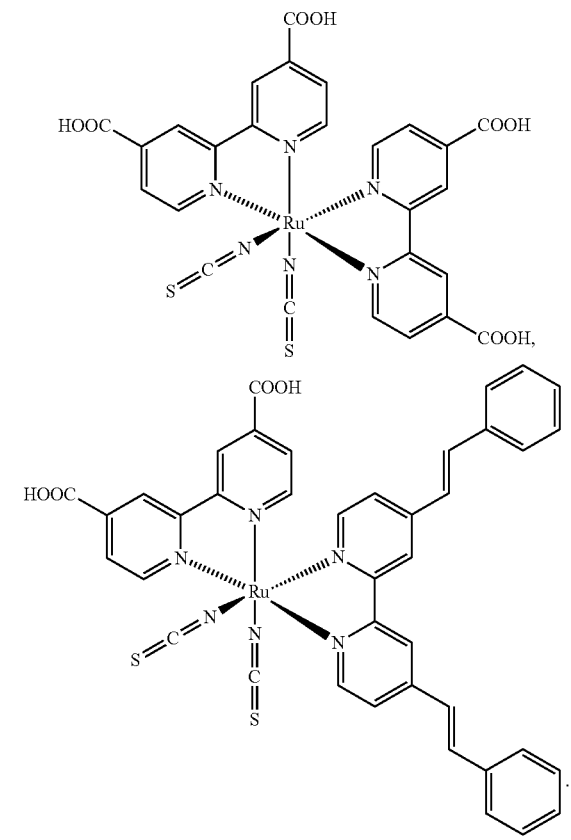

In one embodiment, the dye-sensitized photovoltaic device of the invention, which comprises said dendritic photosensitizing dye of formula (I) and said second photosensitizing dye, further comprises a third photosensitizing dye, which second and third photosensitising dyes are other than said dendrimer of formula (I). The second and third photosensitizing dyes may be the same or different; typically, each is independently selected from photosensitizing dyes which comprise Ru and photosensitizing dyes which comprise a catechol group. Thus, the device which comprises said dendritic photosensitizing dye of formula (I) may further comprise one or more Ru-containing dyes and/or one or more dyes which comprise a catechol group. Typically, the second photosensitizing dye is a Ru(II) complex, for instance a heteroleptic Ru(II) complex as described above, and the third photosensitizing dye is an unsubstituted or substituted benzene-1,2-diol (i.e. catechol) compound as defined above.

Some of the dendrimer compounds of formula (I) are novel. Thus, the invention further provides a compound which is a dendrimer of formula (I):

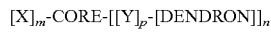

[X]$_m$-CORE-[[Y]$_p$-[DENDRON]]$_n$     (I)

wherein
n is an integer from 1 to 6;
m is an integer from 1 to 6;
each p is independently either 0 or an integer from 1 to 5;
CORE is a metal atom or a metal ion or a group which comprises a metal atom or metal ion, wherein CORE provides at least (n+m) points of attachment, each of said (n+m) points of attachment being bonded to one X, Y or DENDRON group;
each DENDRON is the same or different and represents an at least partially conjugated dendritic molecular structure comprising at least one branching group and optionally at least one linking group, the branching groups being selected from aryl and heteroaryl groups, and the linking groups being selected from aryl, heteroaryl, vinyl, acetylenyl and C$_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups;
—[Y]$_p$— is a linking group bonded to CORE and terminating in a single bond to the first branching group of DENDRON, wherein each Y is the same or different and is selected from aryl, heteroaryl, vinyl, acetylenyl, C$_{1-15}$ alkylene and C$_{1-15}$ alkyleneoxy groups; and
each X, which is the same or different, is an anchoring group which is (a) other than DENDRON, and (b) capable of attachment to a semiconductive metal oxide.

The dendrimers of the invention can be built in a convergent or divergent route, but a convergent route is preferred. Convergent and divergent routes for the preparation of dendrimers are well known in the art, and are described, for instance, in WO99/21935, WO01/59030, WO02/067343, WO2004/020448, WO2004/020504, WO2004/020547 and WO2004/101707. Such methods can readily be used by the skilled person to synthesise dendrimers of formula (I).

With particular regard to dendrimers in which the CORE is a metal atom or a metal ion or a group which comprises a metal atom or metal ion, the dendrons can be attached to appropriate ligands, which ligands can subsequently be attached to the metal to form a dendritic metal complex. Optionally other non-dendritic ligands can subsequently be attached to said complex. Alternatively a ligand with a suitably reactive functional group can be complexed to the metal, and then reacted with appropriately functionalised dendrons. In this latter method, not all ligands have to have the reactive functional groups, and thus this method allows the attachment of dendrons to some but not all of the ligands complexed to the metal. The strategy for a sample convergent synthesis of a first generation dendrimer of the invention is shown in Scheme 1.

Examples 1 to 3 and 8 describe exemplary methods for preparing dendrimers of the invention. These methods can, however, be readily modified in order to prepare other dendrimers falling within the invention. A person skilled in the art will readily be able to prepare suitable starting materials to make dendrimers having, for example, different surface groups or different linking groups. A simple change of reactant can result in the dendrimers being attached to a different point of the core, or different surface groups being present at the distal ends of the dendrimers.

The present invention further provides a novel class of catechol-based sensitizers which can be used together with the dendrimer sensitizers of formula (I). Accordingly, the present invention provides a compound of formula (VII):

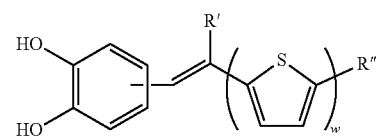

wherein R' is H or CN, typically CN; w is an integer of 2 to 5; and R" is H, C$_{1-15}$ alkyl or DENDRON, wherein DENDRON is as defined herein. Thus, DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and C$_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

Figure 8:
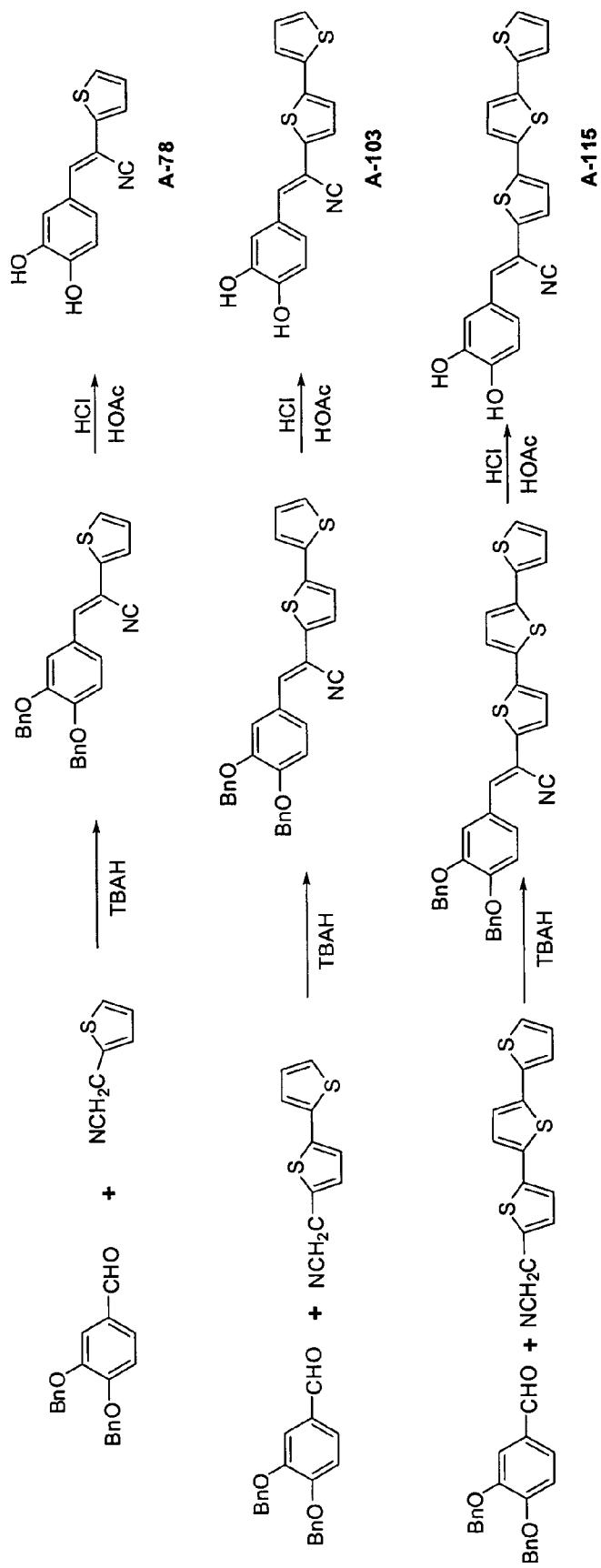
FIG. 8 shows schematically the synthesis routes for the catechol DTCT dye sensitizers A-78, A-103 and A-115.

Such catechol compounds can be synthesised using any suitable process known to those skilled in the art, or by the processes described herein in the Examples below; exemplary syntheses are shown in FIG. 8 and described in Example 6, (i)-(iii).

Typically, the compound of the invention, of formula (VII), is any one of the following compounds:

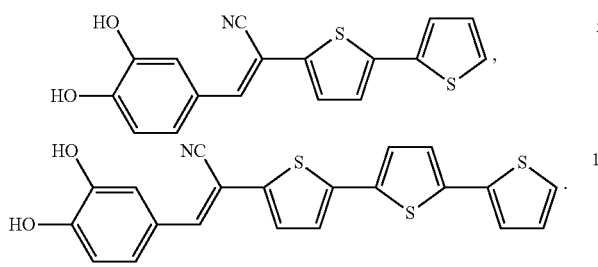

The dye-sensitized photovoltaic devices of the invention may be made by conventional processes.

A process for producing a dye-sensitized photovoltaic device of the invention comprises: (i) forming a layer of the electron acceptor material on, or over, a substrate comprising the first electrode; (ii) depositing the photosensitive dye on, or over, the electron acceptor layer; (iii) forming a layer of the redox mediator material on, or over, the photosensitive dye and electron acceptor layer; and (iv) forming the second electrode on, or over, the redox mediator material. Typically, the substrate comprising a first electrode is indium tin oxide (ITO) on glass. Typically, the ITO is F-doped ITO. The electron acceptor layer may be deposited by evaporation, Glancing Angle Deposition (GLAD), vacuum sputtering, spin coating, doctor blading or solution processing techniques, as appropriate. Doctor blading is a well-known process for producing a layer of metal oxide material in which a slurry of the material is spread onto the substrate using the edge of a moving blade. Typically, forming the electron acceptor layer involves deposition of the layer, followed by drying the as-deposited layer. More typically, the step of forming the electron acceptor layer involves deposition of the layer, followed by drying and annealing the deposited layer. Typically the annealing is carried out at a temperature of from 400° C. to 550° C. Typically the metal oxide is titania. The material of the first and/or second electrode may be deposited by sputtering, vapour deposition or spin coating of a liquid precursor solution. The dye, i.e. the dendrimer of formula (I), may be deposited by solution processing. Conventional solution processing techniques such as spin coating, printing, dip-coating and soaking can be used to deposit the dye. In the case of a liquid electrolyte the cell is made by putting the second electrode, which comprises a high work function metal on a substrate, onto the first substrate whilst leaving a gap using suitable spacing materials. The cell is then filled with the electrolyte. In the case of solid hole transport materials these can be added either by solution processing techniques or evaporated onto the titania/dye composition. The cathode is then deposited onto the hole transport layer usually by evaporation or by deposition from a liquid precursor before appropriate heat treatment to create the high work function metallic layer which may or may not be porous or structured to enhance the process of charge exchange.

The invention will be described further in the Examples which follow:

Examples

Examples 1 to 3

Synthesis of dendrimers A-22 (Example 1), A-67 (Example 2) and A-68 (Example 3)

Scheme 1. Synthesis of Ru sensitizers A-22, A-67 and A-68

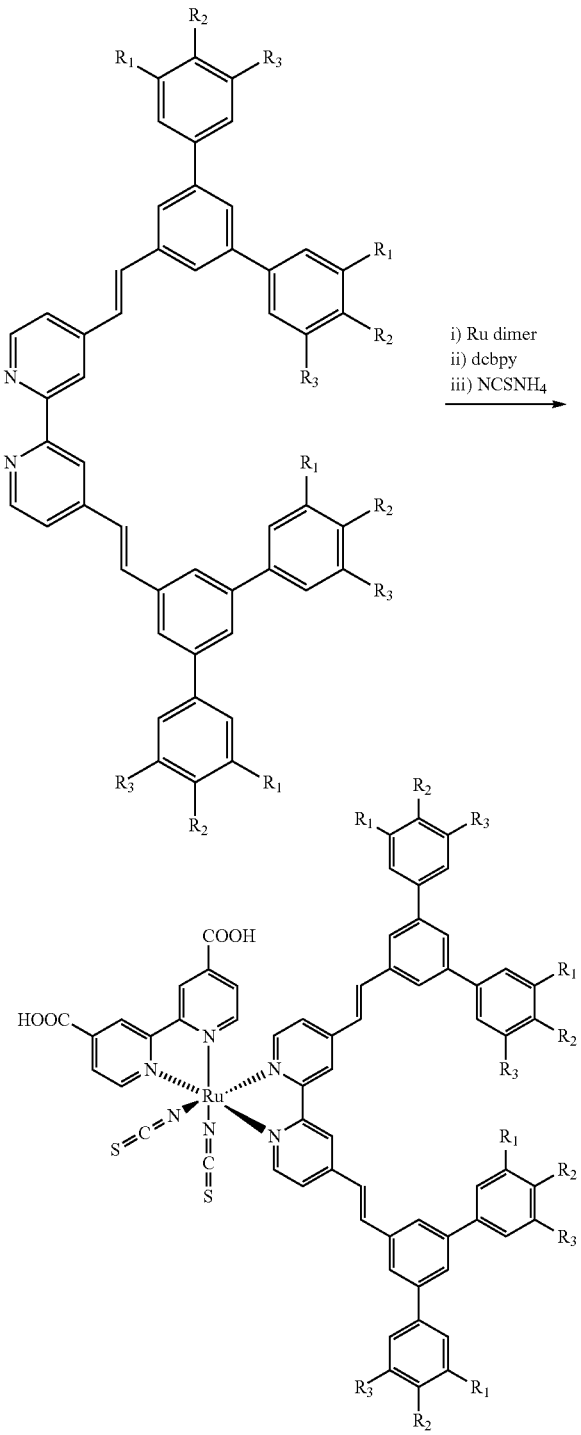

A-22: $R_1$ and $R_3$ = H, $R_2$ = 2-ethylhexyloxy
A-67: $R_1$ = H, $R_2$ and $R_3$ = 2-ethylhexyloxy
A-68: $R_1$, $R_2$ and $R_3$ = 2-ethylhexyloxy (i) Synthesis of DiPy-G1-MEH Scheme 2. Synthesis of DiPy-G1-MEH

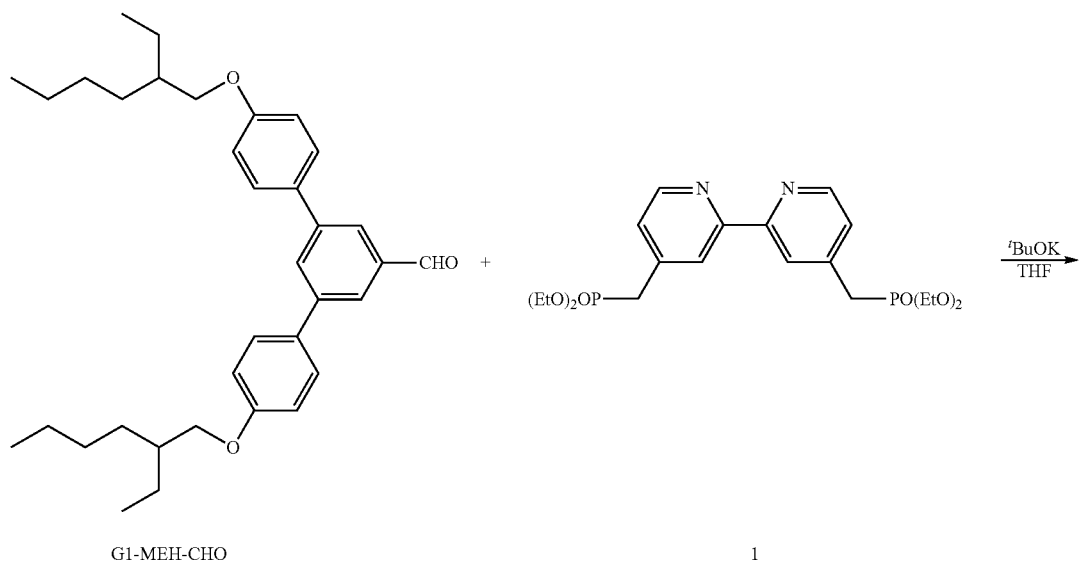

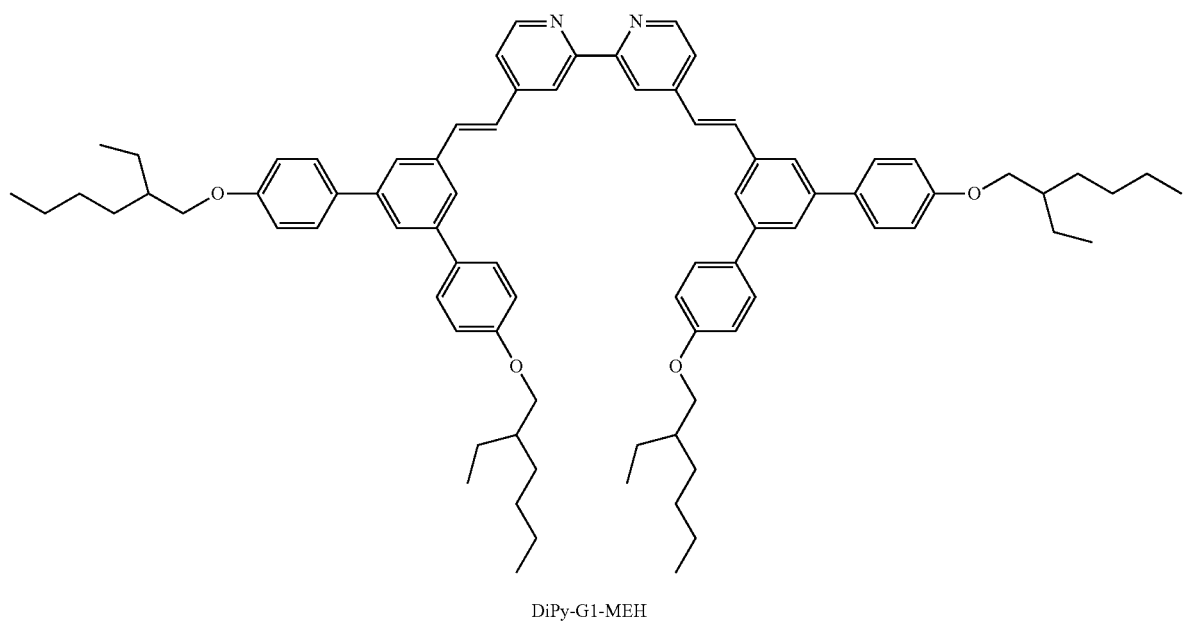

Potassium tert-butoxide (0.62 g, 5.5 mmol) was added to a solution of the compound 1 (1.00 g, 2.2 mmol) and G1-MEH-CHO (2.53 g, 4.9 mmol) in THF (30 mL). Compound 1 was prepared according to the following reference; (1) A. P. Smith et al, *Organic Syntheses*, 2004, 10, 107, (2) L. Viau et al, *Tetrahedron Lett*, 2004, 45, 125. Compound 2 was prepared according to the following reference; S.-C. Lo et al, *Adv. Func. Mater.* 2005, 15, 1451. The reaction mixture was stirred for 3 hours at room temperature. After addition of water (20 mL), THF was removed under reduced pressure. The aqueous residue was extracted with dichloromethane (200 mL). The collected organic layers were washed with brine (100 mL) and water (200 mL), and dried over magnesium sulfate, and filtered. The crude product was purified by column chromatography (deactivated) on silica gel column (ethyl acetate: petroleum ether=1:3) to provide 2.36 g (yield=92%). $^1$H-NMR (400 MHz, CDCl$_3$) δ (ppm) 8.71 (d, 2H, J=4.0 Hz), 8.62 (s, 2H), 7.69 (s, 6H), 7.61 (d, 8H, J=8.0 Hz), 7.58 (d, 2H, J=16.0 Hz, trans vinylene), 7.25 (d, 2H, J=16.0 Hz, trans vinylene), 7.02 (d, 8H, J=12.0 Hz), 3.92 (d, 8H, J=4.0 Hz), 1.80-0.92 (m, 60H). EI MS calcd for C$_{82}$H$_{100}$N$_2$O$_4$ 1177.68 m/z, found: 1177.76 m/z.

(ii) Synthesis of DiPy-G1-DEH
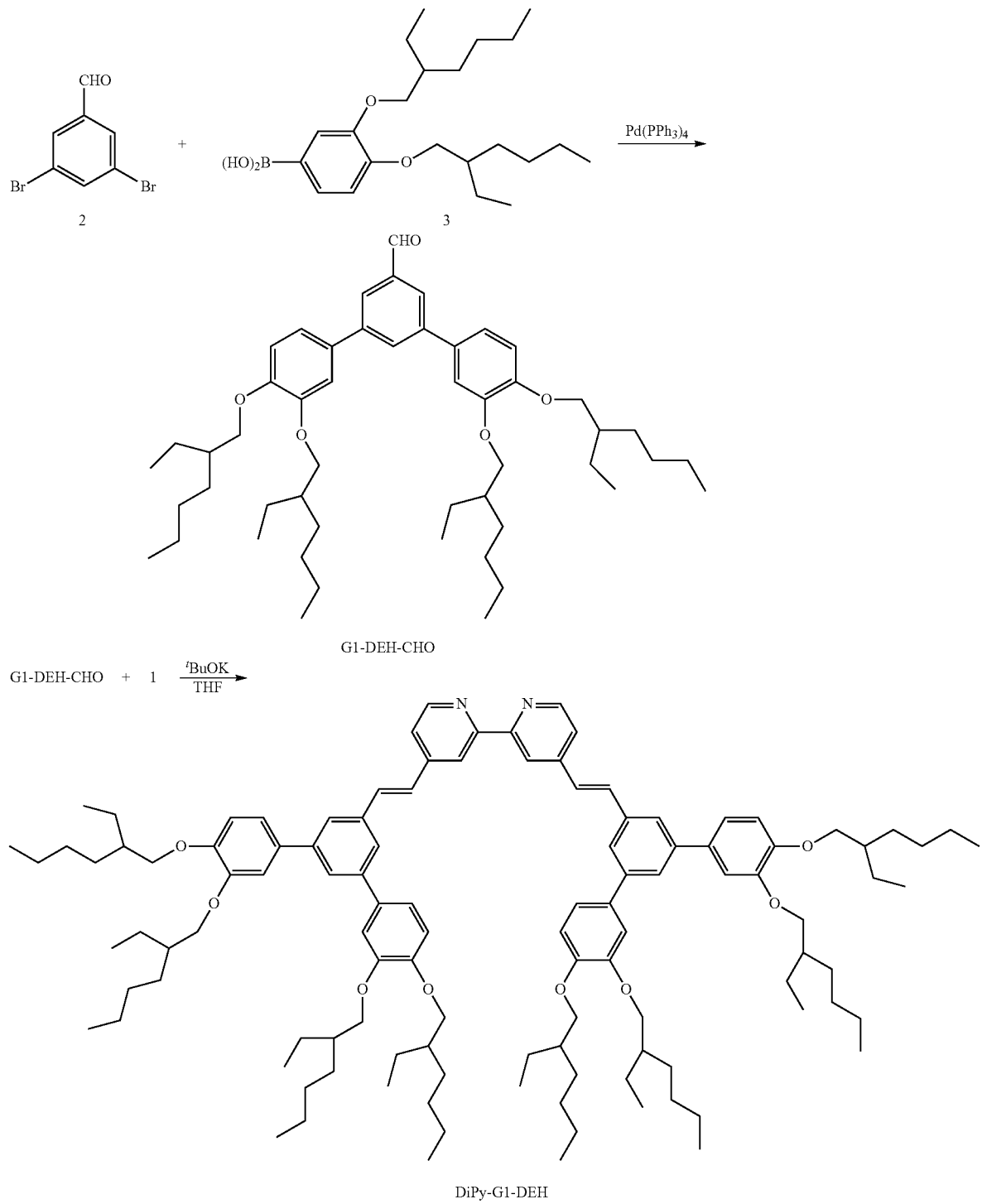
Compound 3
This compound was prepared by the modification of the method described in D. Stewart et al, *J. Mater. Chem.* 1998, 8, 47. Viscous liquid (yield=70%). $^1$H-NMR (400 MHz, CDCl$_3$) δ (ppm) 7.81 (d, 1H, J=8.0 Hz), 7.68 (s, 1H), 6.99 (d, 1H, J=8.0 Hz), 4.02-3.95 (m, 4H), 1.84-0.89 (m, 30H). EI MS calcd for C$_{22}$H$_{39}$BO$_4$ 378.35 m/z, found (+Na (23 m/z)): 401.28 m/z.
G1-DEH-CHO
To a degassed mixture of Pd(PPh$_3$)$_4$ (92 mg, 0.08 mmol) and compound 2 (1.6 g, 6 mmol) in THF (30 mL) were added the compound 3 (5.0 g, 13.2 mmol) and a saturated aqueous solution of potassium carbonate (2N, 15 mL). The mixture was refluxed for 12 hours and poured into a saturated solution of ammonium chloride, and extracted with diethyl ether (100 mL) three times. The combined extracts were washed with brine (100 mL) and dried over magnesium sulfate. After the solvent was removed by rotary evaporation, the remaining oil was purified by column chromatography on silica gel column (ethyl acetate: petroleum ether=1:10) to provide 3.74 g (yield=81%). $^1$H-NMR (400 MHz, CDCl$_3$) δ (ppm) 10.15 (s, 1H), 7.98 (m, 3H), 7.21-7.17 (m, 4H), 6.98 (d, 2H, J=8.0 Hz), 3.97-3.93 (m, 8H), 1.81-0.89 (m, 60H). EI MS calcd for C$_{51}$H$_{78}$O$_5$ 771.76 m/z, found (+Na (23 m/z)): 793.57 m/z.

DiPy-G1-DEH

This compound was prepared according to the procedure described for DiPy-G1-MEH utilizing the G1-DEH-CHO (2.0 g, 2.6 mmol), the compound 1 (0.53 g, 1.2 mmol) and potassium tert-butoxide (0.33 g, 2.9 mmol). The crude product was purified by column chromatography (deactivated) on silica gel column (ethyl acetate: petroleum ether=1:10) to provide 1.70 g (yield=87%). $^1$H-NMR (400 MHz, CDCl$_3$) δ (ppm) 8.71 (d, 2H, J=4.0 Hz), 8.64 (s, 2H), 7.68 (s, 6H), 7.60 (d, 2H, J=16.0 Hz, trans vinylene), 7.45 (dd, 2H, J=4.0 Hz), 7.26 (d, 2H, J=16.0 Hz, trans vinylene), 7.22-7.19 (m, 8H), 6.99 (d, 4H, J=8.0 Hz), 4.0-3.94 (m, 16H), 1.84-0.90 (m, 120H). MADI-TOF MS calcd for C$_{114}$H$_{164}$N$_2$O$_8$ 1690.53 m/z, found: 1690.23 m/z.

(ii) Synthesis of DiPy-G1-TEH

Scheme 4. Synthesis of DiPy-G1-TEH

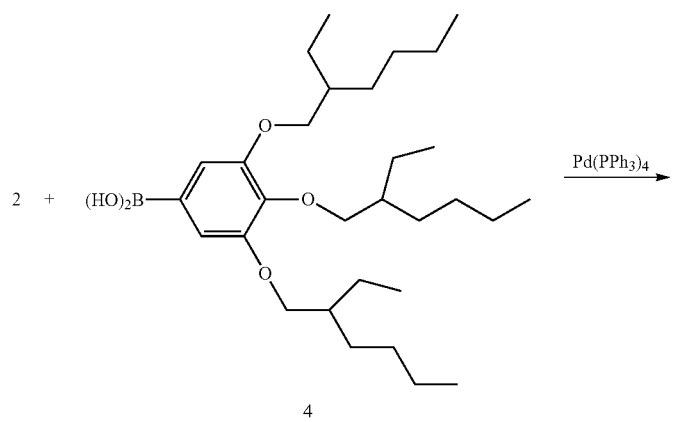

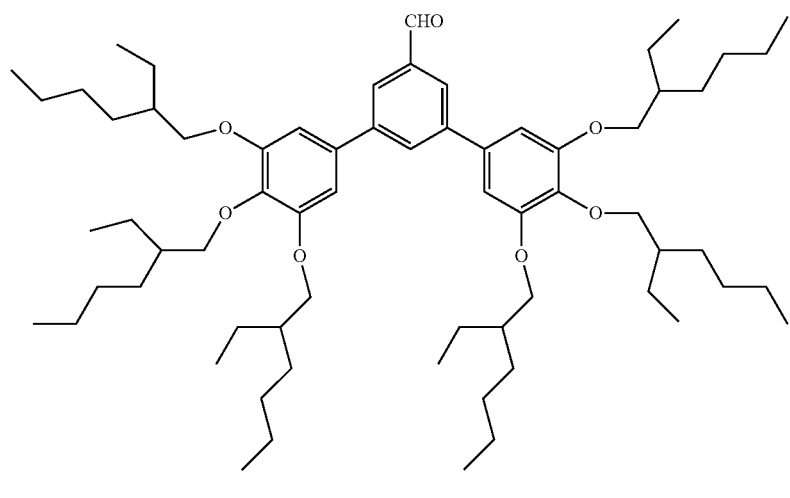

G1-TEH-CHO

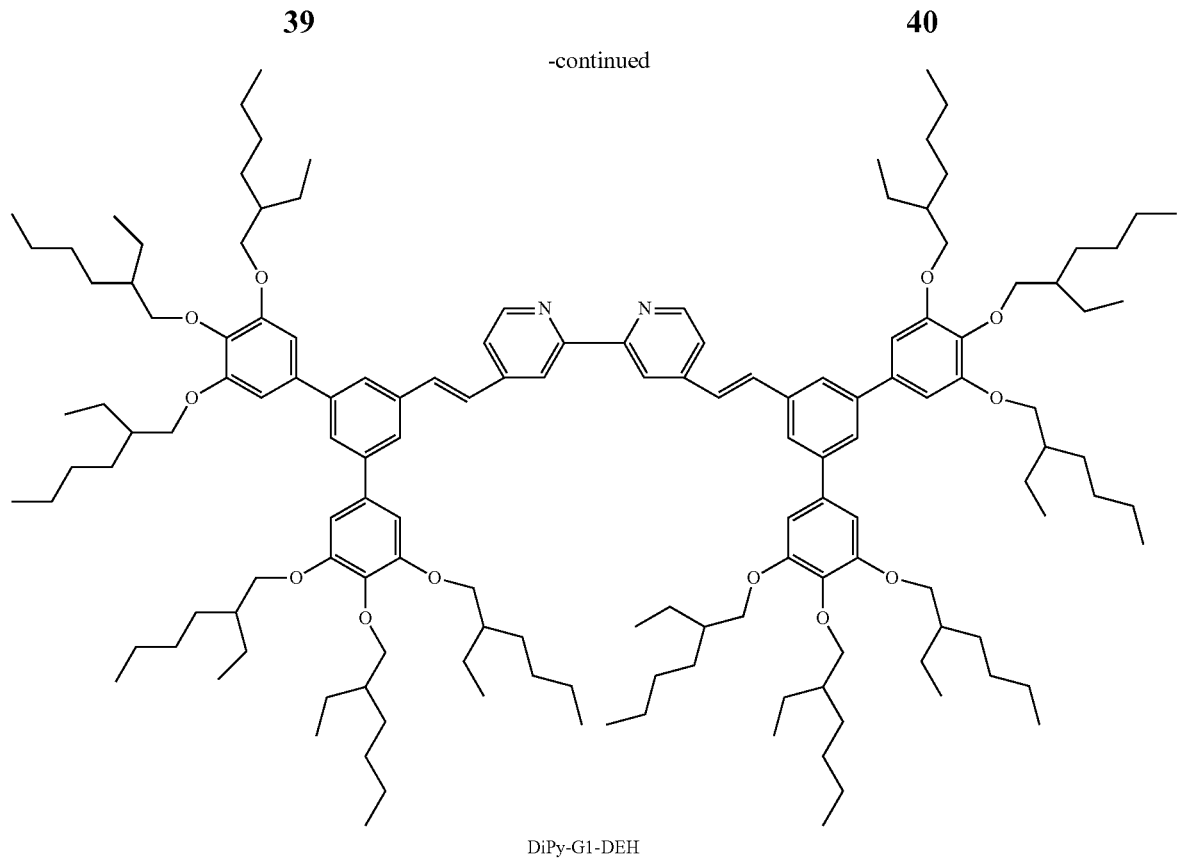

DiPy-G1-DEH

Compound 4

This compound was prepared by the modification of the method described in H. Lee et al, *Tetrahydron Lett.* 2004, 45, 1019. Viscous liquid (yield=63%). $^1$H-NMR (400 MHz, CDCl$_3$) δ (ppm) 7.40 (s, 2H), 3.99-3.95 (m, 6H), 1.78-0.89 (m, 45H). EI MS calcd for $C_{30}H_{55}BO_5$ 506.57 m/z, found (+Na (23 m/z)): 529.40 m/z.

G1-DEH-CHO

This compound was prepared according to the procedure described for G1-DEH-CHO utilizing the compound 2 (0.95 g, 3.6 mmol), the compound 4 (4.0 g, 7.9 mmol) and Pd(PPh$_3$)$_4$ (0.05 g, 0.05 mmol). The crude product was purified by column chromatography on silica gel column (ethyl acetate: petroleum ether=1:20) to provide 2.86 g (yield=78%). $^1$H-NMR (400 MHz, CDCl$_3$) δ (ppm) 10.16 (s, 1H), 7.99 (s, 2H), 7.95 (s, 1H), 6.81 (s, 4H), 3.95-3.88 (m, 12H), 1.81-0.89 (m, 90H). EI MS calcd for $C_{67}H_{110}O_7$ 1027.59 m/z, found (+Na (23 m/z)): 1049.82 m/z.

DiPy-G1-DEH

This compound was prepared according to the procedure described for DiPy-G1-MEH utilizing the G1-TEH-CHO (2.7 g, 2.6 mmol), the compound 1 (0.54 g, 1.2 mmol) and potassium tert-butoxide (0.33 g, 2.9 mmol). The crude product was purified by column chromatography (deactivated) on silica gel column (ethyl acetate: petroleum ether=1:10) to provide 2.45 g (yield=95%). $^1$H-NMR (400 MHz, CDCl$_3$) δ (ppm) 8.71 (d, 2H, J=4.0 Hz), 8.65 (s, 2H), 7.69 (s, 6H), 7.66 (s, 2H), 7.61 (d, 2H, J=16.0 Hz, trans vinylene), 7.26 (d, 2H, J=16.0 Hz, trans vinylene), 6.82 (s, 8H), 3.99-3.87 (m, 24H), 1.84-0.89 (m, 180H). MADI-TOF MS calcd for $C_{146}H_{228}N_2O_{12}$ 2203.38 m/z, found: 2203.61 m/z.

(iv) Synthesis of Ru Complex

Scheme 5. Synthesis of Ru complex A-22

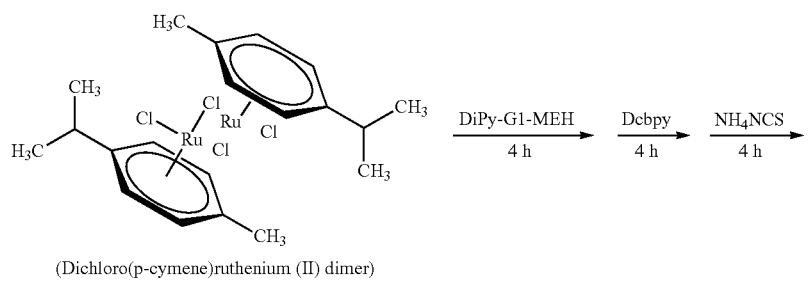

(Dichloro(p-cymene)ruthenium (II) dimer)

-continued

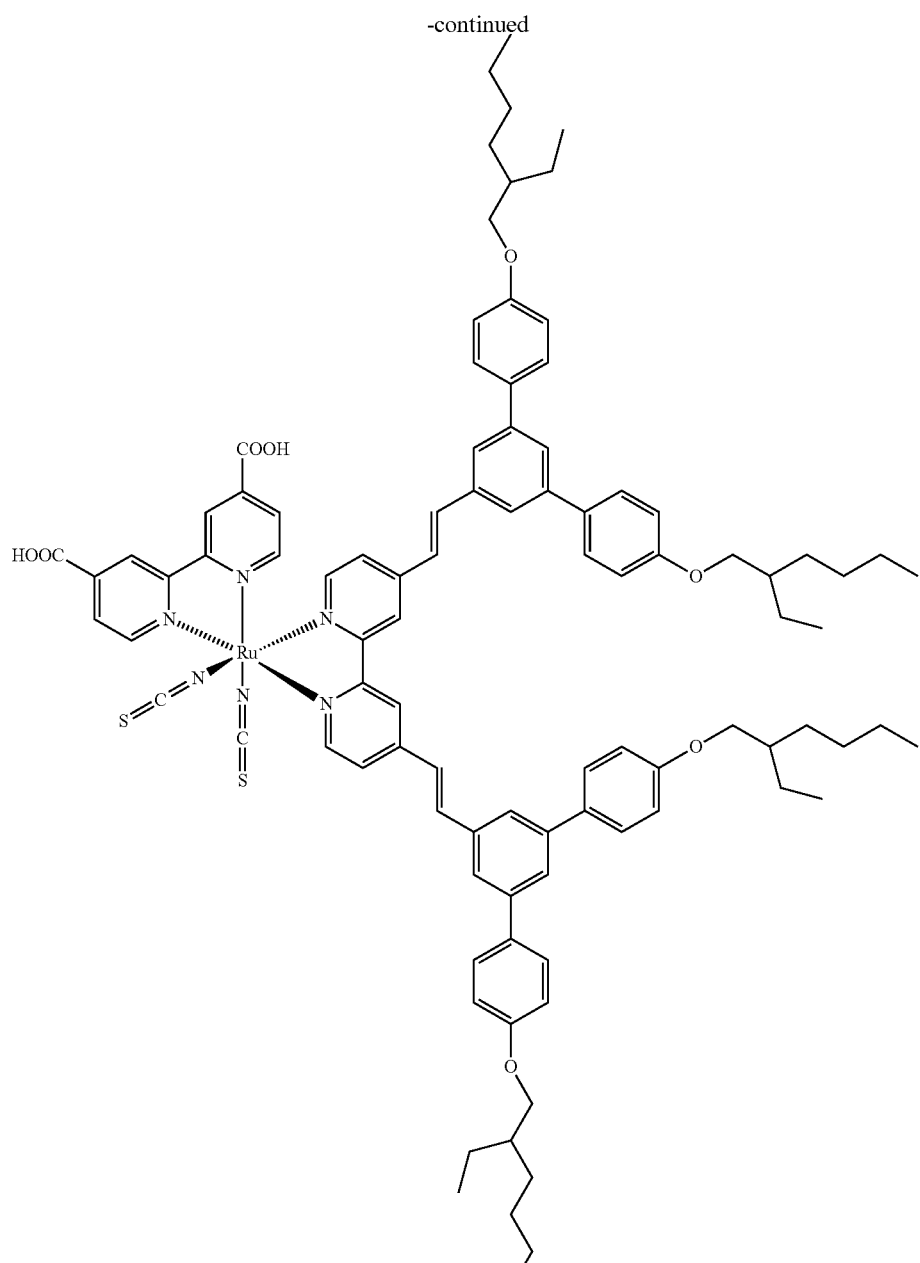

A-22

General procedure for A-22, A-67 and A-68:

{RuCl(p-cymene)}$_2$ (50 mg, 0.08 mmol) and DiPy-G1-MEH (276 mg, 0.16 mmol) were dissolved in distilled DMF (25 mL). The reaction mixture was heated at 80° C. under nitrogen for 4 hours. Then, 2,2'-bipyridine-4,4'-dicarboxaldehyde (Dcbpy) (40 mg, 0.16 mmol) was added and refluxed at 150-160 degrees C. for another 4 hours under reduced light to avoid isomerization (2,2'-bipyridine-4,4'-dicarboxaldehyde was prepared according to the method described in N. Garelli et al, *J. Org. Chem.* 1992, 57, 3046). Subsequently, an excess of NH$_4$NCS (310 mg, 4.1 mmol) was added to the mixture and heated at 150° C. for a further 4 h. The reaction mixture was cooled to room temperature and the solvent was removed by using a raotary evaporator under vacuum. Water (20 mL) was added to the flask and the insoluble solid was collected on a sintered glass crucible by suction filtration, and washed with distilled water. The crude complex was dissolved on a solution of tetrabutylammonium hydroxide (TBAH) in methanol (5 mL). the concentrated solution was charged onto a Sephadex LH-20 column and eluted with methanol. The main band was collected and concentrated. The required complex was isolated upon addition of 0.01M HNO$_3$.

Characterising Data for A-22 (Example 1)

Dark black solid (yield=63.0%)
$^1$H-NMR (400 MHz, DMSO-d) δ (ppm) 9.44 (d, 1H, J=4.0 Hz), 9.17 (d, 1H, J=4.0 Hz), 9.08 (s, 1H), 8.99 (s, 1H), 8.93 (s, 1H), 8.84 (s, 1H), 8.28 (d, 1H), 8.08 (d, 1H), 8.07 (s, 1H), 8.03 (s, 1H), 7.92-7.32 (m, 20H), 7.02 (dd, 8H, J=8.0, 20.0 Hz), 3.88 (dd, 8H, J=8.0, 16.0 Hz), 1.74-0.86 (m, 60H). MADI-TOF MS calcd for $C_{96}H_{108}N_6O_8RuS_2$ 1639.12 m/z, found: 1638.7 m/z.

Characterising Data for A-67 (Example 2)

Dark black solid (yield=54.0%)

$^1$H-NMR (500 MHz, DMSO-d, 373K) δ (ppm) 9.55 (d, 1H), 9.28 (d, 1H), 9.17 (s, 1H), 8.95 (s, 1H), 8.90 (s, 1H), 8.80 (s, 1H), 8.28 (d, 1H), 8.15 (d, 1H), 8.07 (s, 1H), 8.03 (s, 1H), 7.90-7.20 (m, 20H), 7.02 (dd, 4H, J=10.0, 20.0 Hz), 3.88 (m, 16H), 1.74-0.86 (m, 120H). MADI-TOF MS calcd for $C_{128}H_{172}N_6O_{12}RuS_2$ 2151.97 m/z, found: 2151.10 m/z.

Characterising Data for A-68 (Example 3)

Dark black solid (yield=30.1%)

$^1$H-NMR (500 MHz, DMSO-d, 373K) δ (ppm) 9.55 (d, 1H), 9.25 (d, 1H), 9.05 (s, 1H), 8.95 (s, 1H), 8.90 (s, 1H), 8.80 (s, 1H), 8.28 (d, 1H), 8.13 (d, 1H), 8.05 (s, 1H), 8.03 (s, 1H), 7.80-7.38 (m, 12H), 7.02 (s, 4H), 6.95 (s, 4H), 3.95-3.83 (m, 24H), 1.74-0.87 (m, 180H). MADI-TOF MS calcd for $C_{160}H_{236}N_6O_{16}RuS_2$ 2664.82 m/z, found: 2664.60 m/z.

Example 4

Fundamental Properties of Dendritic Ru Sensitizers A-22, A-67 and A-68

Fundamental optical and physical properties of the dendritic Ru sensitizers A-22, A-67 and A-68 were characterised by comparison with the simple Ru sensitizers N3 and A-29. This was done in order to check the versatility of dendritic structures and predict their performances in dye-sensitized solar cell (DSSC) devices. The structures of N3 and A-29 are as follows:

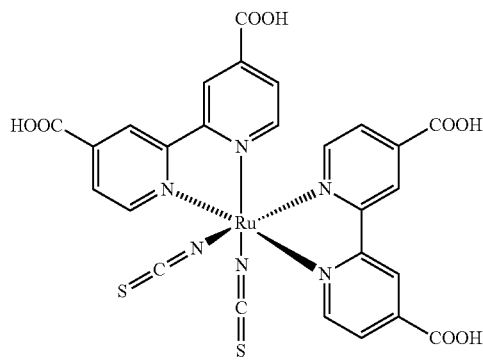

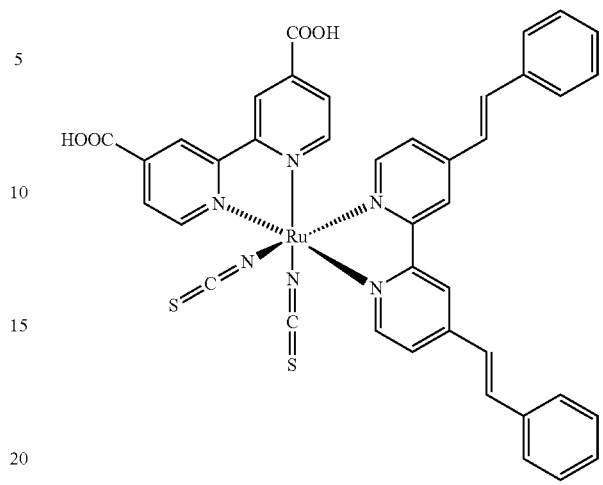

N3 is a known Ru sensitizer. A-29 was prepared for investigating the characteristics of dendritic structures versus a non-dendritic structure; the conjugation length of the bipyridyl ligand in A-29 is the same as that of the bipyridyl ligand in each of the dendritic compounds.

It was found that the dendritic sensitizers A-22, A-67 and A-68 met requirements for high performance DSSC sensitizers with both high conversion efficiency and good stability.

(i) Light Harvesting Capacity

The light harvesting efficiency is governed by the molar extinction coefficient of the dye. In the region of UV light (250 nm-450 nm), dendritic Ru sensitizers A-22, A-67 and A-68 each showed a higher molar extinction coefficient than the simple Ru sensitizers N3 and A-29. Without wishing to be bound by theory, this is thought to be due to the four additional phenoxyl chromophore groups in the dendritic sensitizers. In addition, in the region of visible light (450 nm-700 nm), the molar extinction coefficient of the lowest MLCT band of the dendritic Ru sensitizers is higher than that of the simple Ru sensitizers. The data obtained are presented in Table 1 below. The data show that dendritic sensitizers absorb more light than the simple Ru sensitizers.

TABLE 1

| Molar extinction coefficient of dyes | | | | | |
|---|---|---|---|---|---|
| | Simple Ru dyes | | Dendritic Ru dyes | | |
| | N3 | A-29 | A-22 | A-67 | A-68 |
| Molar extinction coefficient at 300 nm[1] (ε, × 10$^3$ M$^{-1}$cm$^{-1}$) | 53.0 | 60.3 | 94.5 | 94.1 | 91.0 |
| Molar extinction coefficient at MLCT[2] (ε, × 10$^3$ M$^{-1}$cm$^{-1}$) | 12.4 | 17.3 | 18.1 | 19.2 | 20.2 |

[1]Measured in DMF solution (1 × 10$^{-5}$ mol/L)
[2]Measured in DMF solution (5 × 10$^{-5}$ mol/L)

(ii) Minimising Dye Aggregation

Figure 4:
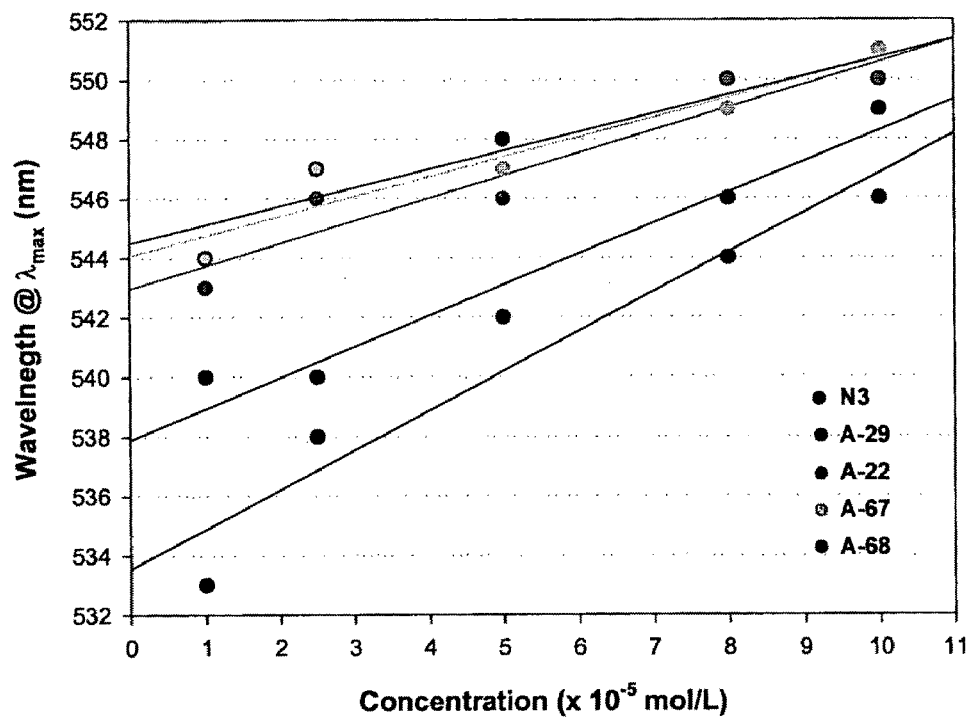
FIG. 4 is a graph of the concentration of dye sensitizer in DMF, in units of ×10⁶ mol/L, versus wavelength at $\lambda_{max}$ in units of nm (y axis); plots are shown for the simple Ru sensitizers N3 and A-29 (bottom two lines), as well as for the dendritic Ru sensitizers (uppermost three lines).

Dye aggregation of Ru sensitizers generally leads to a decreased photon-to-current conversion efficiency of the DSSC since it can lead to intermolecular quenching of the excited state. It was found that the maximum peak of the MLCT band of all ruthenium sensitizers is red-shifted as the dye concentration increases, which is most probably due to the intermolecular interactions of dyes (dye aggregation) (see FIG. 4). As shown in FIG. 4, the degree of red-shift of the maximum peak caused by increasing the dye concentration decreases as the bulkiness of the Ru sensitizer increases (i.e. in increasing order, N3→A-29→A-22→A-67→A-68). This indicates that dendritic Ru sensitizers are less susceptible to molecular aggregation than simple Ru sensitizers (N3 and A-29).

(iii) Preventing Dye Desorption from the Surface of $TiO_2$ by the Penetration of Liquid Ionic Electrolyte The hydrophobicity of the dye-desorbed $TiO_2$ substrate is thought to be important for preventing interaction of triiodide with bare $TiO_2$, which, in turn, retards a backward electron transfer from $TiO_2$ conduction band to the triiodide and prevents the desorption of the dyes from the $TiO_2$ surface. It was found by contact angle measurements (see Table 2) that the dendritic Ru sensitizers A-22, A-67 and A-68 show better hydrophobicity than the simple Ru sensitizers N3 and A-29, owing to their many peripheral bulky alkyl chains.

TABLE 2

Contact angles of a bare $TiO_2$ substrate and dye-adsorbed $TiO_2$ substrates

| Dye sensitizer | None (sintered bare $TiO_2$) | N3 | A-29 | A-22 | A-68 |
|---|---|---|---|---|---|
| Contact angle (°) | 40.4 | 16.0 | 55.3 | 137.8 | 136.6 |

(iv) Enhancing the Thermal Stability of Dyes

Figure 5:
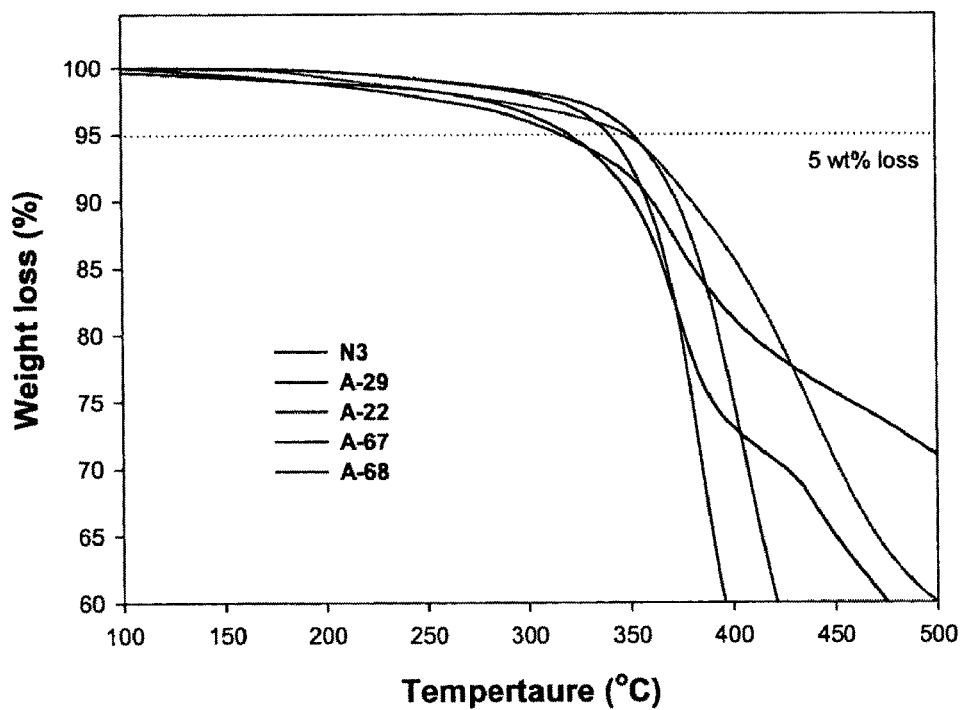
FIG. 5 is a graph of temperature in degrees centigrade (x axis) versus % weight loss (y axis) for the Ru sensitizer compounds N3, A-29, A-22, A-67 and A-68. The curves shown are the measured TGA curves for each of the compounds.

DSSC sensitizers require high thermal stability for long-term device stability because they are exposed to very harsh environments. According to thermogravimetric analysis (TGA), the dendritic Ru sensitizers A-22, A-67 and A-68 show higher thermal stability than simple Ru sensitizers N3 and A-29, owing to their robust and rigid aromatic dendritic ligand structures (see FIG. 5 and Table 3). FIG. 5 shows the TGA curves for each of N3, A-29, A-22, A-67 and A-68.

TABLE 3

Temperature of 5% loss of Ru sensitizers measured by TGA

| | Dye sensitizer | | | | |
|---|---|---|---|---|---|
| | N3 | A-29 | A-22 | A-67 | A-68 |
| Temperature of 5% loss (° C.) | 319 | 315 | 348 | 340 | 351 |

Example 5

Device Performance of Dendritic Ru Sensitizers

Figure 6:
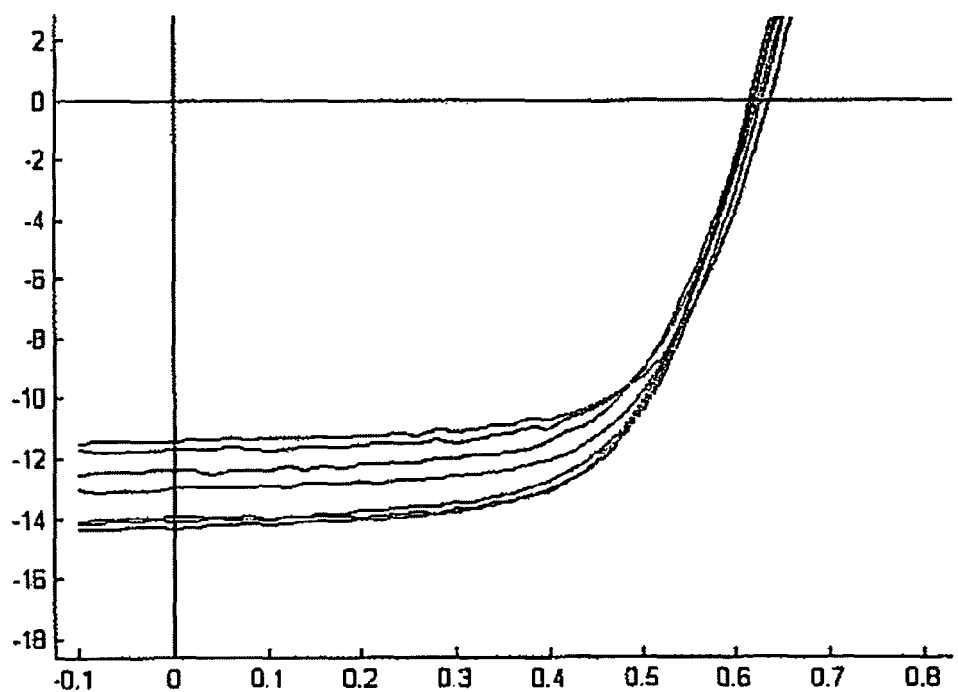
FIG. 6 is a graph of applied bias in units of Volts (x axis) versus current density in units of mA/cm² (y axis), which shows the device performance results for the dendritic Ru sensitizer A-22 under standard AM1.5G illumination with correction included for the spectral mismatch function.

The $TiO_2$ films used here were purchased from Dyesol Pty. Ltd. (Queanbeyan, NSW Australia). They consisted of a 11-12 µm thick films of 20 nm anatase TiO2 particles and 10 percent by weight 400 nm scattering particles on a glass substrate coated with a 15 ohms/square film of fluorine doped tin oxide (FTO). The surface area of the films was approximately 80 $m^2/g$. When purchased, the anode films were 11 mm long by 8 mm wide. This area was reduced to 11 mm long by approximately 2 mm wide by removing a portion of the film with a razor blade in order to minimise the effect of series resistance losses in the FTO. The exact width of the modified films was measured with a Vernier calliper. After modification, the films were calcined at 450° C. for 30 minutes in air. The platinum back contacts were also purchased from Dyesol Pty. Ltd. They consisted of a screen printed platinum film on a glass substrate coated with a 15 ohms/square film of fluorine doped tin oxide (FTO). A22 was introduced with a 0.3 mM solution in 1:1 dimethylformamide (DMF):dimethyl sulfoxide (DMSO). The dyes were introduced by immersing the photoanodes in the dye solutions for at least 18 hours. If the photoanodes were used immediately following calcining, the substrates were cooled to approximately 100° C. and immediately immersed in the dye solution to prevent the adsorption of water onto the film. If not used immediately, the anodes were heated to above 100° C. for 10 minutes prior to being immersed in the dye solution to remove any water on the film. Upon removal from the dye solution, the sensitised photoanodes were rinsed in either acetonitrile and DMF for the A22 cells. The cells were constructed by sealing the photoanode substrate to the Pt electrode substrate with a gasket cut from 25 µm DuPont Surlyn film. The gasket was cut slightly larger than the cell active area to prevent molten Surlyn from permeating the porous photoanode, and channels were left in the gasket to allow filling of the electrolyte. The electrolyte was filled through 1 mm diameter holes drilled in the substrate prior to the Pt deposition. The cells were filled through either the channels in the gasket or the pre-drilled holes with an electrolyte of 0.5 M LiI, 0.04 M I2 and 0.5 M 4-tert-butylpyridine. The cells were sealed using hot-melt glue. Finally the cells were contacted by soldering copper wires to each of the TCO substrates with a low-temperature indium and silver solder. The device performance of one of the dendritic Ru sensitizers, A-22, is summarised in FIG. 6 and Table 4. A-22 shows relatively high conversion efficiencies reproducibly.

TABLE 4

Summary of the observed cell characteristics for cells dyed with A-22 in 9:1 DMF/Acetonitrile
A-22 DMF/MeCN Cell Characteristics under the AM1.5 G (100 $mW/cm^2$)

| Device name | Cell area ($cm^2$) | $V_{oc}$ (V) | $J_{sc}$ (mA · $cm^2$) | FF (%) | PCE (%) |
|---|---|---|---|---|---|
| Device 1 | 0.206 | 0.75 | 12.21 | 0.70 | 6.40 |
| Device 2 | 0.214 | 0.72 | 13.55 | 0.64 | 6.32 |
| Device 3 | 0.209 | 0.72 | 13.35 | 0.67 | 6.42 |
| Device 4 | 0.196 | 0.72 | 13.75 | 0.64 | 6.38 |
| Device 5 | 0.208 | 0.71 | 13.34 | 0.64 | 6.09 |

Example 6

Optimisation Study: Adsorption of Ru Sensitizers onto $TiO_2$ Substrates

Studies were performed in order to find the best conditions for adsorption of the dendritic Ru sensitizers A-22, A-67 and A-68 onto $TiO_2$ substrates for use in devices. In those studies, various dipping solution conditions were studied, such as the dipping solvent composition, dipping solution temperature and solvent purity. A reliable method for studying these parameters was established, as follows: 3 mL of dye solution ($\times 10^4$ mol/L) was loaded in a pyrex round-bottomed flask. A suitably cut $TiO_2$ substrate was then loaded into the flask. The flask inlet was tightly sealed by a stopper and Teflon tape. After dipping for 24 hours, the solution was measured by UV/vis absorption spectroscopy, so that the concentration of the adsorbed dye onto the $TiO_2$ substrate could be calculated.

(i) Dipping Solution Temperature

It was found that increasing the dipping solution temperature from room temperature to 50° C. did not greatly enhance the concentration of the adsorbed dyes onto $TiO_2$. Furthermore, at the high dipping solution temperature of 80° C., the concentration of adsorbed A-67 molecules onto the TiO$_2$ substrates was slightly decreased. This result indicates that the dye desorption process from solution-dipped TiO$_2$ substrates is accelerated in high temperature environments. The results are summarised in Table 5 below.

TABLE 5

The number (N$_A$) of the adsorbed A-67 molecules onto the TiO$_2$ substrates[1] at different dipping temperatures for 24 hours

|  | Room temp | 50° C. | 80° C. |
|---|---|---|---|
| The number of the adsorbed A-67 onto the TiO$_2$ substrates (N$_A$[10$^{15}$ cm$^{-2}$]) | 62.8 | 63.1 | 59.5 |

[1] The area of the TiO$_2$ substrates is 0.88 cm$^2$ (0.8 cm × 1.1 cm).

In summary, it was found that the temperature of the dipping solvent did not enhance dye adsorption onto the TiO$_2$ substrates, which may be due to the competition of adsorption and desorption process induced by thermal energy.

(i) Purity of Dipping Solution

The moisture in the dipping solvent can affect the dye adsorption onto TiO$_2$. In order to check how much the moisture in DMF affects the concentration of dye adsorbed onto a TiO$_2$ substrate, the concentration of adsorbed A-67 molecules was measured at room temperature using both a non-distilled DMF solvent and a dried DMF solvent, distilled from commercial DMF. The results are summarised in Table 6 below, which show that the purity of the DMF did not have much effect on the amount of A-67 dye adsorbed onto the TiO$_2$ substrates.

TABLE 6

The number (N$_A$) of the adsorbed A-67 molecules onto the TiO$_2$ substrates[1] using distilled and non-distilled DMF solvents at room temperature for 24 hours.

|  | Distilled DMF | Non-distilled DMF |
|---|---|---|
| The number of the adsorbed A-67 onto the TiO$_2$ substrates (N$_A$[10$^{15}$ cm$^{-2}$]) | 62.8 | 61.9 |

[1] The area of the TiO$_2$ substrates is 0.88 cm$^2$ (0.8 cm × 1.1 cm).

(iii) Dipping Solution Composition

It is known that the polarity of dipping solvents and the solubility of dye molecules in dipping solvents strongly affect the concentration of dye adsorbed onto TiO$_2$ substrate. In order to find an optimum dipping solution combination for the dendritic Ru sensitizers, the amount of dye adsorbed onto TiO$_2$ substrates was measured at room temperature using various dipping solvent combinations.

Of the solvents tested, it was found that DMF (good solvent for A-22): MeCN (good adsorbing solvent on TiO$_2$) (1:1) was the best dipping solvent composition for high A-22 adsorption onto TiO$_2$ (see Table 7).

TABLE 7

The number (N$_A$) of the adsorbed A-22 molecules onto the TiO$_2$ substrates[1] using different dipping solvent compositions

| Solvent system | DMF | DMF:DMSO (1:1) | DMF:MeCN (9:1) | DMF:MeCN (4:1) | DMF:MeCN (1:1) |
|---|---|---|---|---|---|
| N$_A$ of adsorbed A-22 (N$_A$[10$^{15}$ cm$^{-2}$]) | 63.5 | 68.3 | 70.5 | 74.7 | 75.1 |

[1] The area of the TiO$_2$ substrates is 0.88 cm$^2$ (0.8 cm × 1.1 cm).

Of the solvents tested, it was found that DMF (good solvent for A-67): MeCN (good adsorbing solvent on TiO$_2$) (9:1) was the best dipping solvent composition for high A-67 adsorption onto TiO$_2$ (see Table 8).

TABLE 8

The number (N$_A$) of the adsorbed A-67 molecules onto the TiO$_2$ substrates[1] using different dipping solvent compositions

| Solvent system | N$_A$ of adsorbed A-67 (N$_A$[10$^{15}$ cm$^{-2}$]) |
|---|---|
| 62.8 | DMF |
| 35.5 | DMF:DMSO (3:1) |
| 37.4 | DMF:DMSO (9:1) |
| 58.1 | DMF:t-BuOH (9:1) |
| 66.0 | DMF:Acetone (9:1) |
| 58.2 | DMF:Toluene (9:1) |
| 55.0 | DMF:CHCl$_3$ (9:1) |
| 69.0 | DMF:MeCN (9:1) |
| 67.7 | DMF:MeCN (4:1) |

[1] The area of the TiO$_2$ substrates is 0.88 cm$^2$ (0.8 cm × 1.1 cm)

Of the solvents tested, it was found that DMF (good solvent for A-68): MeCN (good adsorbing solvent on TiO$_2$) (9:1) was the best dipping solvent composition for high A-67 adsorption onto TiO$_2$ (see Table 9).

TABLE 9

The number (N$_A$) of the adsorbed A-68 molecules onto the TiO$_2$ substrates[1] using different dipping solvent compositions

| Solvent system | DMF | DMF:MeCN (9:1) |
|---|---|---|
| N$_A$ of adsorbed A-68 (N$_A$[10$^{15}$ cm$^{-2}$]) | 63.5 | 75.1 |

[1] The area of the TiO$_2$ substrates is 0.88 cm$^2$ (0.8 cm × 1.1 cm)

However, overall there was not a strong relationship between the polarity of dipping solvent and dye adsorption.

In summary, it was found that a mixed solvent system, especially the DMF and acetonitrile (MeCN) mixture, could enhance effectively the adsorption of the dendritic dyes onto TiO$_2$. DMF is a good solvent for the dendritic Ru sensitizers A-22, A-67 and A-68, and MeCN is a known co-solvent for high dye-adsorption onto the TiO$_2$ substrates. However, the Ru sensitizers A-22, A-67 and A-68 have poor solubility in acetonitrile. Thus, it is necessary to mix two solvents suitably for high dye adsorption onto TiO$_2$. The amount of dendritic dye adsorbed onto TiO$_2$ was absorbed to decrease as the molecular volume increases (A-22→A-67→A-68) because of steric hindrance between the dye molecules.

Example 7

Figure 7:
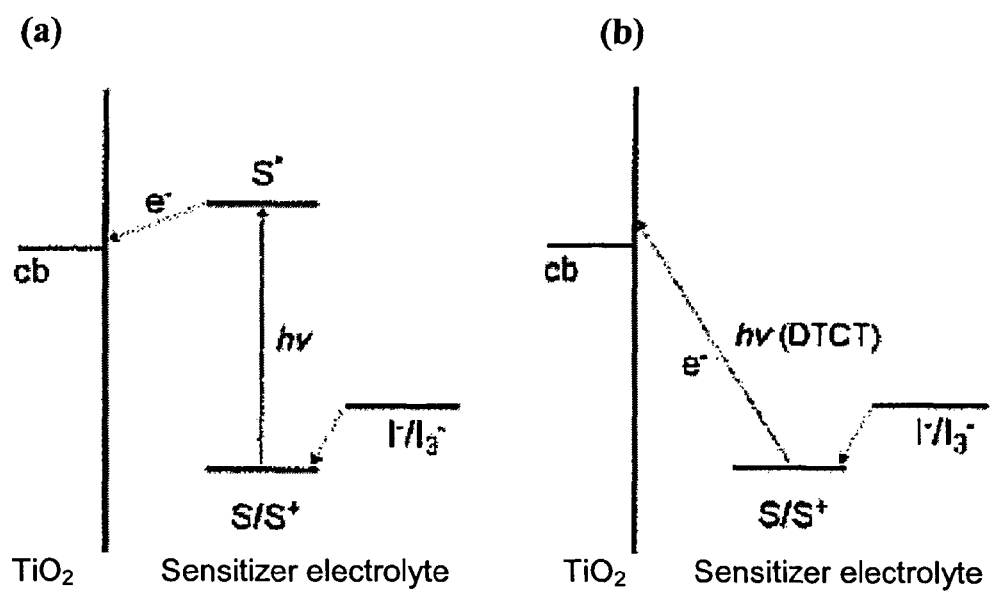
FIG. 7 is an energy diagram of the two different types of electron injection pathways from an adsorbed dye to $TiO_2$ in a dye-sensitized solar cell (DSSC); pathway (a) shows the two-step electron injection of the Grätzel type DSSC, in which electrons are injected from the excited state of the dye (e.g. a Ru(II) complex) to the conduction band of $TiO_2$; pathway (b) shows a one-step electron injection from the ground state of the dye to the conduction band of $TiO_2$ by photoinduced charge-transfer (CT) excitation of the dye-to-$TiO_2$ CT (DTCT) band.

Hybrid DSSCs Comprising a Dendritic Ru Dye Sensitizer and a Further Dye Sensitizer In general, DSSC's can be classified into two types, depending on the electron-injection pathway from the dye to the conduction band (CB) of $TiO_2$ (see FIG. 7). One is the Grätzel type DSSC in which electrons are injected from the excited state of the dye (e.g. a Ru(II) complex) to the conduction band of $TiO_2$ (two-step electron injection). The other is a 'one-step' electron injection from the ground state of the dye to the conduction band of $TiO_2$ by photoinduced charge-transfer (CT) excitation of the dye-to-$TiO_2$ CT (DTCT) band.

The conversion efficiency of DSSC's having dendritic Ru sensitizers such as A-22, A-67 and A-68 could be enhanced by co-adsorption of an additional photon-to-current conversion source, a sensitizer which is much smaller than the dendritic Ru dye sensitizer, onto the $TiO_2$ substrate. The sensitizer which is co-adsorbed with the Ru dendrimer could be a simple Ru sensitizer, for instance N3 or A29, or alternatively a DTCT dye. DTCT dyes include pi-conjugated catechol molecules; such molecules can be used for photovoltaic sensitizers by direct dye-to-$TiO_2$ charge transfer (DTCT), which produces a 'one-step' electron injection from the ground state of the dye to the conduction band of $TiO_2$. A new class of DTCT dyes, A-78, A-103 and A-115, was therefore designed and prepared. The structures of A-78, A-103 and A-115 are as follows:

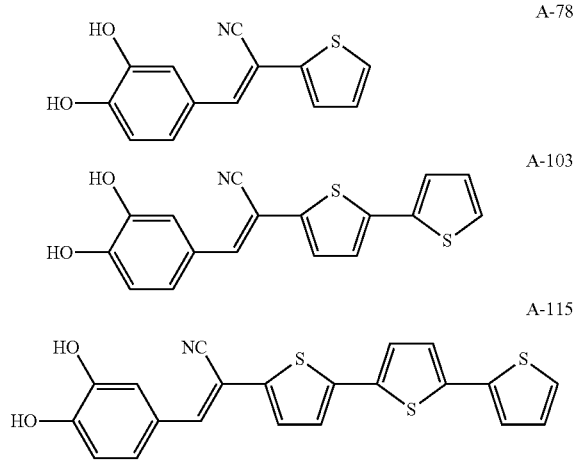

According to co-adsorption experiment results described hereinbelow, it was proven that dendritic Ru sensitizers, for instance A-22, A-67 and A-68, are suitable candidates for co-adsorption onto $TiO_2$ with a smaller sensitizer such as A-78, A-103 or A-115. Simple Ru sensitizers, on the other hand, are not good candidates for co-adsorption with DTCT dyes such as A-78, A-103 or A-115; this is because the simple Ru dyes are susceptible to desorption from $TiO_2$ during co-adsorption of the DTCT dye.

(i) Synthesis of A-78

Scheme 6. Synthesis of A-78

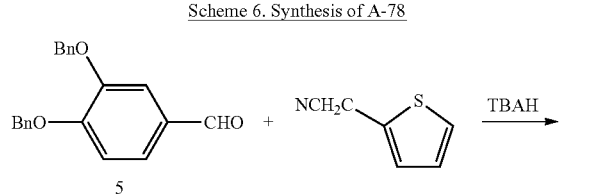

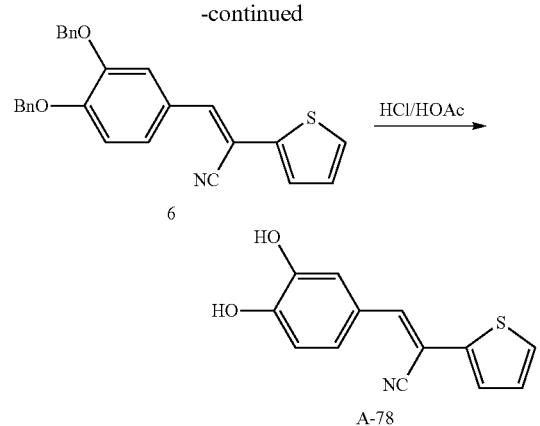

Compound 6

To a stirred solution of the compound 5 (1 g, 3.1 mmol) and 2-thiopheneacetonitrile (Aldrich, 0.39 g, 3.1 mmol) in t-butanol and THF mixture (10 mL:2 mL), tetrabutylammonium hydroxide (TBAH) solution (0.34 mL, 0.3 mmol) was slowly added. (Compound 5 was prepares according to the method described in C. C. Li et al, *J. Org. Chem.* 2003, 68, 8500.) After 2 hours, the mixture was poured into the water, and extracted with dichloromethane (200 mL). After the solvent was removed by rotary evaporation, the crude product was purified by column chromatography on silica gel column (ethyl acetate: petroleum ether=1:3) to provide 1.0 g (yield=75%).

$^1$H-NMR (400 MHz, $CDCl_3$) δ (ppm) 7.62 (s, 1H), 7.50 (d, 2H, J=8.0 Hz), 7.45 (d, 2H, J=8.0 Hz), 7.41-7.24 (m, 10H), 7.05 (t, 1H), 6.95 (d, 1H, J=8.0 Hz), 5.25 (s, 2H), 5.24 (s, 2H). EI MS calcd for $C_{27}H_{21}NO_2S$ 423.53 m/z, found (+$NH_4^+$ (18 m/z)): 441.16 m/z.

A-78

The compound 6 (0.8 g, 1.9 mmol) was dissolved in glacial acetic acid (5 mL) and concentrated HCl (5 mL), and stirred at 120° C. under $N_2$. After 2 hours, the reaction mixture was poured into water (100 mL), and extracted with dichloromethane (200 mL). The organic layer was washed with water (100 mL) three times and dried over magnesium sulfate. After the solvent was removed by rotary evaporation, the crude product was purified by column chromatography on silica gel column (ethyl acetate: petroleum ether=1:3) to provide 0.25 g (yield=55%). $^1$H-NMR (400 MHz, DMSO-d) δ (ppm) 7.60 (d, 1H, J=4.0 Hz), 7.55 (s, 1H), 7.48 (s, 1H), 7.34 (d, 1H, J=4.0 Hz), 7.14 (d, 1H, J=8.0 Hz), 6.85 (t, 1H), 6.83 (d, 1H, J=8.0 Hz). EI MS calcd for $C_{13}H_9NO_2S$ 243.28 m/z, found (+Na (23 m/z)): 266.02 m/z.

(ii) Synthesis of A-103

Scheme 7. Synthesis of A-103

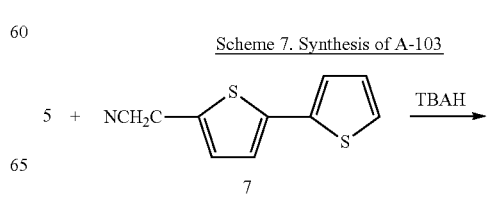

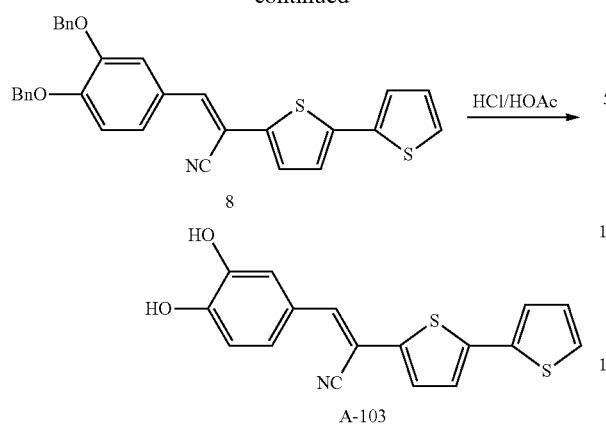

A-103

(iii) Synthesis of A-115

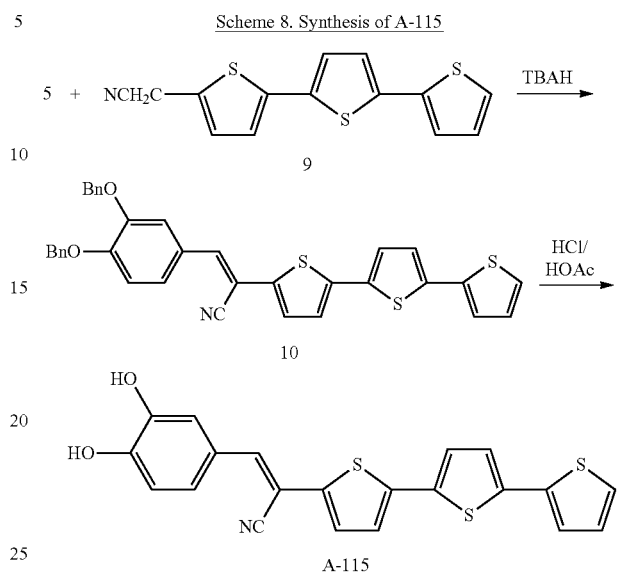

Scheme 8. Synthesis of A-115

Compound 7

To a degassed mixture of Pd(PPh$_3$)$_4$ (217 mg, 0.18 mmol) and 2-(5-bromothiophen-2-yl)acetonitrile (1.86 g, 9 mmol) in THF (25 mL) were added the 2-thienylboronic acid (Aldrich, 2.0 g, 15.6 mmol) and a saturated aqueous solution of potassium carbonate (2N, 15 mL). (2-(5-bromothiophen-2-yl)acetonitrile was prepared according to the method described in N. S. Cho et al, *Macromolecules*, 2004, 37, 5265.) The mixture was refluxed for 12 hours and poured into a saturated solution of ammonium chloride, and extracted with diethyl ether (100 mL) three times. The combined extracts were washed with brine (100 mL) and dried over magnesium sulfate. After the solvent was removed by rotary evaporation, the remaining oil was purified by column chromatography on silica gel column (ethyl acetate: petroleum ether=1:5) to provide 0.71 g (yield=38%). $^1$H-NMR (400 MHz, CDCl$_3$) δ (ppm) 7.24 (d, 1H, J=4 Hz), 7.15 (d, 1H, J=4 Hz), 7.05-7.02 (m, 2H), 6.97 (d, 1H, J=4 Hz), 3.90 (s, 2H).

A-103

To a stirred solution of the compound 5 (0.78 g, 2.4 mmol) and the compound 7 (0.5 g, 2.4 mmol) in t-butanol and THF mixture (10 mL:2 mL), tetrabutylammonium hydroxide (TBAH) solution (0.24 mL, 0.2 mmol) was slowly added. After 2 hours, the mixture was poured into the water, and extracted with dichloromethane (200 mL). After the solvent was removed by rotary evaporation, the crude product was purified by column chromatography on silica gel column (ethyl acetate: petroleum ether=1:5) to provide 1.0 g (yield=83%) of the compound 8.

The compound 8 (0.8 g, 1.6 mmol) was dissolved in glacial acetic acid (10 mL) and concentrated HCl (5 mL), and stirred at 120° C. under N$_2$. After 2 hours, the reaction mixture was poured into water (100 mL), and extracted with dichloromethane (200 mL). The organic layer was washed with water (100 mL) three times and dried over magnesium sulfate. After the solvent was removed by rotary evaporation, the crude product was purified by column chromatography on silica gel column (ethyl acetate: petroleum ether=1:3) to provide 0.32 g of A-103 (yield=62%). $^1$H-NMR (400 MHz, methanol-d) δ (ppm) 7.53 (s, 1H), 7.41-7.07 (m, 6H), 7.09 (m, 1H), 6.85 (dd, 1H, J=4, 8 Hz). EI MS calcd for C$_{17}$H$_{11}$NO$_2$S$_2$ 325.40 m/z, found (+Na (23 m/z)): 348.01 m/z.

The synthesis of A-103 is shown schematically in FIG. 8.

Compound 9

To a degassed mixture of Pd(PPh$_3$)$_4$ (0.23 g, 0.2 mmol) and 2-(5-bromothiophen-2-yl)acetonitrile (2.0 g, 9.9 mmol) in THF (40 mL) were added the 2,2'-bithiophen-5-ylboronic acid (3.5 mg, 16.9 mmol) and a saturated aqueous solution of potassium carbonate (2N, 20 mL). (2,2'-bithiophen-5-ylboronic acid was prepared according to the method described in M. Melucci et al, *J. Org. Chem.* 2002, 67, 8877.) The mixture was refluxed for 12 hours and poured into a saturated solution of ammonium chloride, and extracted with diethyl ether (100 mL) three times. The combined extracts were washed with brine (100 mL) and dried over magnesium sulfate. After the solvent was removed by rotary evaporation, the remaining oil was purified by column chromatography on silica gel column (ethyl acetate: petroleum ether=1:5) to provide 0.80 g (yield=28%). $^1$H-NMR (400 MHz, CDCl$_3$) δ (ppm) 7.24 (d, 1H, J=4 Hz), 7.18 (d, 1H, J=4 Hz), 7.08 (d, 1H, J=4 Hz), 7.06-7.03 (m, 3H), 6.98 (d, 1H, J=4 Hz), 3.91 (s, 2H).

A-115

To a stirred solution of the compound 5 (0.78 g, 2.4 mmol) and the compound 9 (0.70 g, 2.4 mmol) in t-butanol and THF mixture (10 mL:2 mL), tetrabutylammonium hydroxide (TBAH) solution (0.24 mL, 0.2 mmol) was slowly added. After 2 hours, the mixture was poured into the water, and extracted with dichloromethane (200 mL). After the solvent was removed by rotary evaporation, the crude product was purified by column chromatography on silica gel column (ethyl acetate: petroleum ether=1:5) to provide 0.6 g (yield=42%) of the compound 10.

The compound 10 (0.15 g, 0.3 mmol) was dissolved in glacial acetic acid (15 mL) and concentrated HCl (5 mL), and stirred at 120° C. under N$_2$. After 2 hours, the reaction mixture was poured into water (100 mL), and extracted with dichloromethane (200 mL). The organic layer was washed with water (100 mL) three times and dried over magnesium sulfate. After the solvent was removed by rotary evaporation, the crude product was purified by column chromatography on silica gel column (ethyl acetate: petroleum ether=1:1) to provide 0.09 g of A-115 (yield=86%). $^1$H-NMR (400 MHz, acetone-d) δ (ppm) 8.70 (s, 1H, —OH), 8.60 (s, 1H, —OH), 7.68 (s, 1H), 7.50 (m, 3H), 7.35-7.24 (m, 6H), 7.12 (t, 1H), 6.90 (d, 1H, J=4 Hz). EI MS calcd for $C_{21}H_{13}NO_2S_3$ 407.53 m/z, found: 406.20 m/z The synthesis of A-115 is shown schematically in FIG. 8.

(iv) Summary of Properties of A-78, A-103 and A-115

The newly designed pi-conjugated catechol molecules, A-78, A-103 and A-115 show good dye adsorption onto both $TiO_2$ nanoparticles and $TiO_2$ substrates.

The colour of solutions of the catechol dyes (in MeOH, $5\times10^{-5}$ mol/L) became deeper and darker when $TiO_2$ nanoparticles (ca. 5 nm, Anatase) were added, which indicates that the catechol molecules form a charge transfer (CT) complex with the $TiO_2$ nanoparticles.

The adsorption maxima and cut-off peaks of catechol molecules are red-shifted as the number of thiophene moieties increases (A-78→A-103→A115). This indicates that light harvesting efficiency of the dye increases as the pi-conjugation length of the catechol molecule increases. The colour of the $TiO_2$ substrate with catechol molecule adsorbed becomes darker as the pi-conjugation length increases; this is because of the red-shift of the CT bands of the dye-$TiO_2$ substrate complexes.

The direct dye-to-$TiO_2$ charge transfer (DTCT) of A-78, A-103 and A-115 is confirmed by the observation of fluorescence quenching for dye-adsorbed $TiO_2$ substrates. The catechol molecules were also adsorbed onto $SiO_2$ (TLC) plates, which do not form charge transfer complexes with catechols. Unlike the dye-adsorbed $TiO_2$ substrates, the dye-adsorbed $SiO_2$ plates did not show significant colour change. This was due to the absence of CT complex formation between the $SiO_2$ and the catechol dye molecules.

Figure 9:
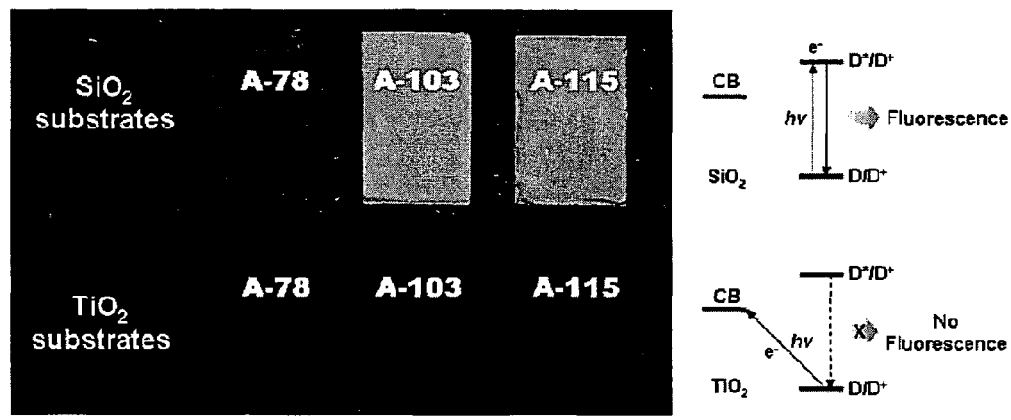
FIG. 9 is a photograph of the catechol A-78-, A-103- and A-115-adsorbed $SiO_2$ (TLC) and $TiO_2$ substrates under the illumination of 365 nm light.

The presence of CT complexes of dye molecules with $TiO_2$ substrates is even more apparent when the substrates are illuminated with UV light. The dye-adsorbed $SiO_2$ substrates show a strong fluorescence under the illumination of 365 nm light, whereas the dye-adsorbed $TiO_2$ substrates show strong fluorescence quenching due to the formation of a DTCT complex in which excitons are transferred directly from the ground state of the dye to the conduction band of $TiO_2$. This is illustrated in FIG. 9.

Figure 10:
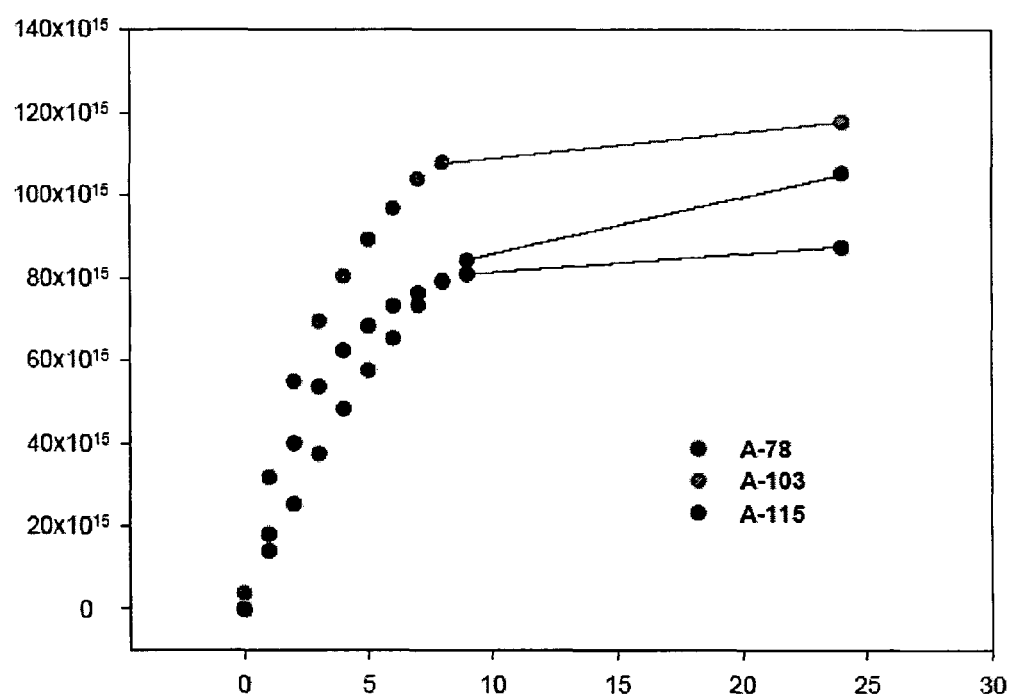
FIG. 10 is a graph of the number of catechol dye molecules adsorbed onto the $TiO_2$ substrate in units of $N_A/cm^2$ (y axis) versus substrate dipping time in units of hours (x axis). Results are shown for three dyes: A-78 (lowest number of adsorbed molecules at 24 hours), A-103 (highest number of adsorbed molecules at 24 hours) and A-115 (intermediate number of adsorbed molecules at 24 hours).

FIG. 10 shows the number of dye molecules adsorbed onto the $TiO_2$ substrates versus substrate dipping time, for A-78, A-103 and A-115. The sintered $TiO_2$ substrates were dipped for 24 hours at room temperature. The area of the substrates was 0.88 cm$^2$ (0.8 cm×1.1 cm). The amount of catechol dye (number of dye molecules) which can be adsorbed onto the $TiO_2$ substrates seems to be related to the acidity and molecular size of catechol molecules. Among the catechol molecules tested, A-103 has the highest adsorbsion number ($N_A$/cm$^2$=117.3×10$^{15}$), which is even higher than the simple Ru sensitizer N3 ($N_A$/cm$^2$=109.2×10$^{15}$) in $^t$BuOH/acetonitrile.

Figure 11:
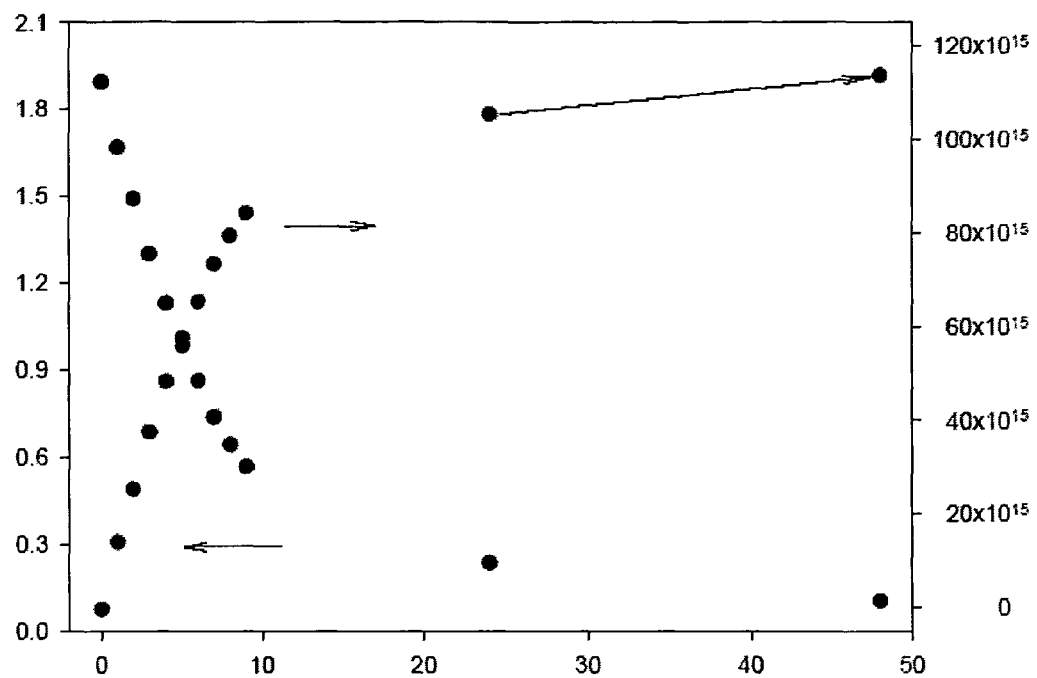
FIG. 11 is a graph of dipping time in units of hours (x axis) versus A-115 dye solution absorbance (left hand y axis) and the number of A-115 dye molecules adsorbed onto the $TiO_2$ substrate in units of $N_A/cm^2$ (right hand y axis).

As can be seen in FIG. 10, the slope of the number of A-78 and A-103 dye molecules adsorbed onto the $TiO_2$ substrate versus substrate dipping time reaches plateau level after 9 hours, whereas the slope for A-115 is still steep at that time. Furthermore, it was observed that A-115 molecules can be continuously adsorbed onto $TiO_2$ substrates even after dipping for 24 hours: $N_A$/cm$^2$ (24 hours)=105.3×10$^{15}$, whereas $N_A$/cm$^2$ (48 hours)=113.6×10$^{15}$; an 8% increase was observed from 24 to 48 hours. This can be seen in FIG. 11, which shows the decrease in the absorbance at 416 nm of a solution of A-115 in MeOH (5×10$^{15}$ mol/L) as well as the increase in the number of A-115 molecules adsorbed onto a sintered $TiO_2$ substrate, after dipping the $TiO_2$ substrate in the A-115 solution for 48 hours at room temperature. The area of the substrates used was 0.88 cm$^2$ (0.8 cm×1.1 cm).

(v) Co-Adsorption of Photovoltaic Sensitizers onto the $TiO_2$ Substrates

Figure 13:
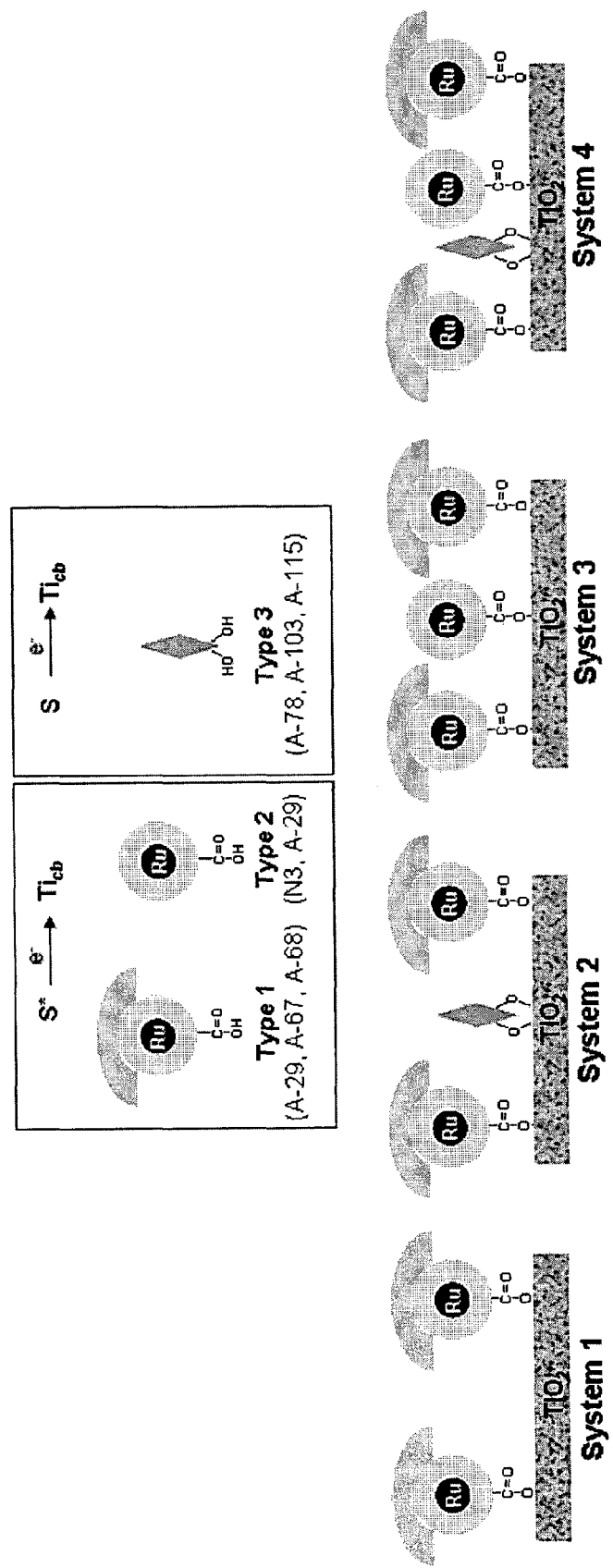
FIG. 13 is a schematic illustration of the co-adsorption of a dendritic Ru dye sensitizer ("Type 1", for instance A-22, A-67 or A-68) and an additional dye sensitizer ("Type 2" or "Type 3") onto the $TiO_2$ substrate. The additional dye sensitizer may be a simple Ru dye sensitizer ("Type 2", for instance N3 or A-29) or a catechol DTCT dye sensitizer ("Type 3", for instance A-78, A-103 or A-115).

The light harvesting and photon-to-current conversion efficiency of the dendritic A-series-based photovoltaic devices can be enhanced by the co-adsorption of small-sized catechol dyes (e.g. A-78, A-103 and A-115) or Ru dyes (e.g. N3, A-29) onto the bulky dendritic Ru dye-adsorbed $TiO_2$ substrates, since these small dyes can be additionally adsorbed onto the surface of the $TiO_2$ nanoparticles, which, in turn, increases the light harvesting efficiency and prevents the contact of $TiO_2$ nanoparticles with redox mediator (e.g. ionic electrolyte) molecules (FIG. 13).

For the efficient co-adsorption of catechol dyes onto the A-series dye-adsorbed $TiO_2$ substrates, A-series dyes should not be desorbed from the $TiO_2$ substrates.

Figure 12:
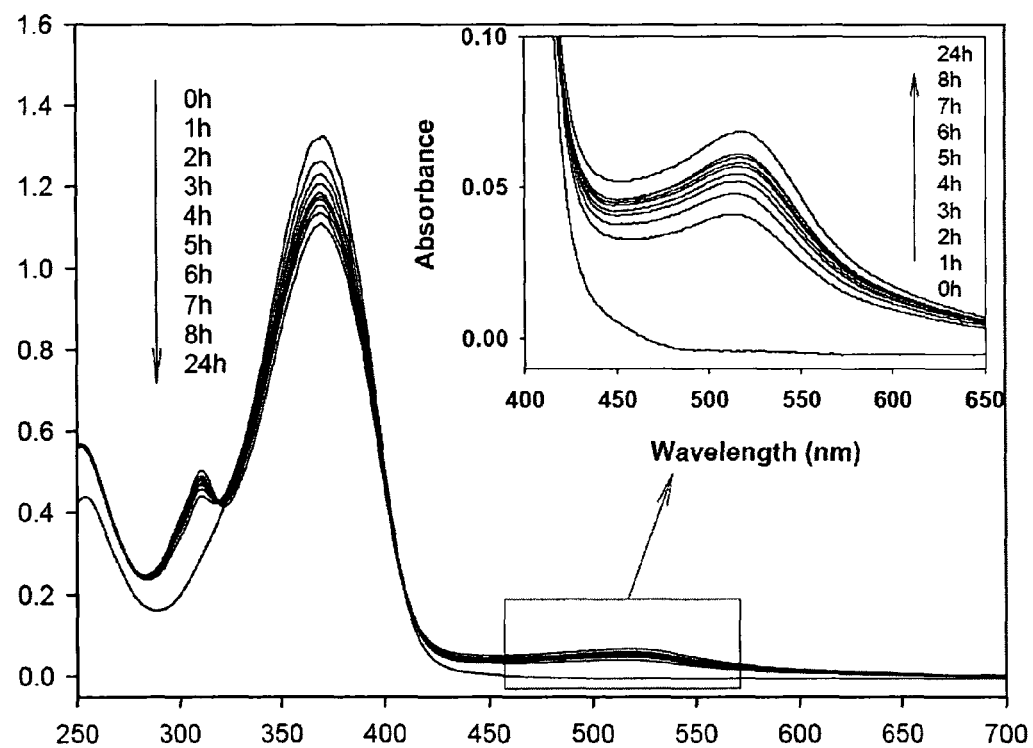
FIG. 12 is a graph of wavelength in units of nm (x axis) versus absorbance of the MeOH dipping solution (y axis). The decrease in the large peak over time is due to the adsorption of the catechol dye A-78 to the $TiO_2$ substrate, whereas the increase in the smaller peak (inset graph) is due to the concurrent desorption of N3.
Figure 14:
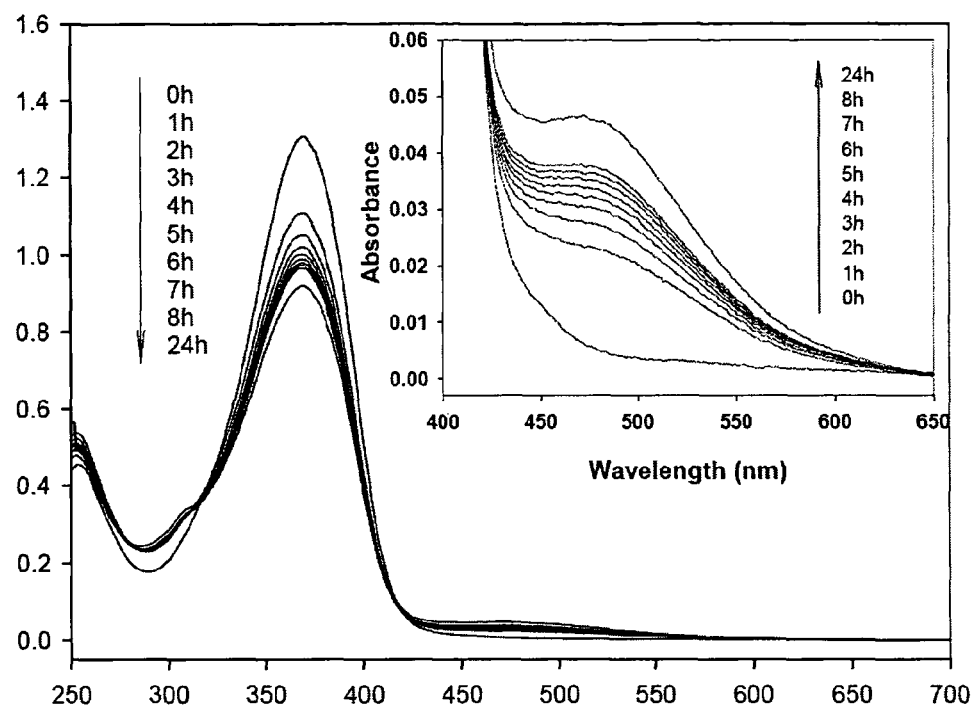
FIG. 14 is a graph of wavelength in units of nm (x axis) versus absorbance of the MeOH dipping solution (y axis). The decrease in the large peak over time is due to the adsorption of the catechol dye A-78 onto the $TiO_2$ substrate, whereas the increase in the smaller peak (inset graph) is due to the concurrent desorption of A-29.

(a) Co-Adsorption of the Catechol dye A-78 onto N3- and A-29-adsorbed $TiO_2$ Substrates It was found that N3- and A29-adsorbed $TiO_2$ substrates are not good for co-adsorption because N3 and A-29 molecules are desorbed from the $TiO_2$ substrates during co-adsorption of A-78 onto the $TiO_2$ substrates. This can be observed in FIGS. 12 and 14. FIG. 12 shows the absorbance change of A-78 in MeOH (5×10$^5$ mol/L) after dipping of a N3-adsorbed $TiO_2$ substrate for 24 hours at room temperature. FIG. 14 shows the absorbance change of A-78 in MeOH (5×10$^5$ mol/L) after dipping of an A-29-adsorbed $TiO_2$ substrate for 24 hours at room temperature.

Figure 15:
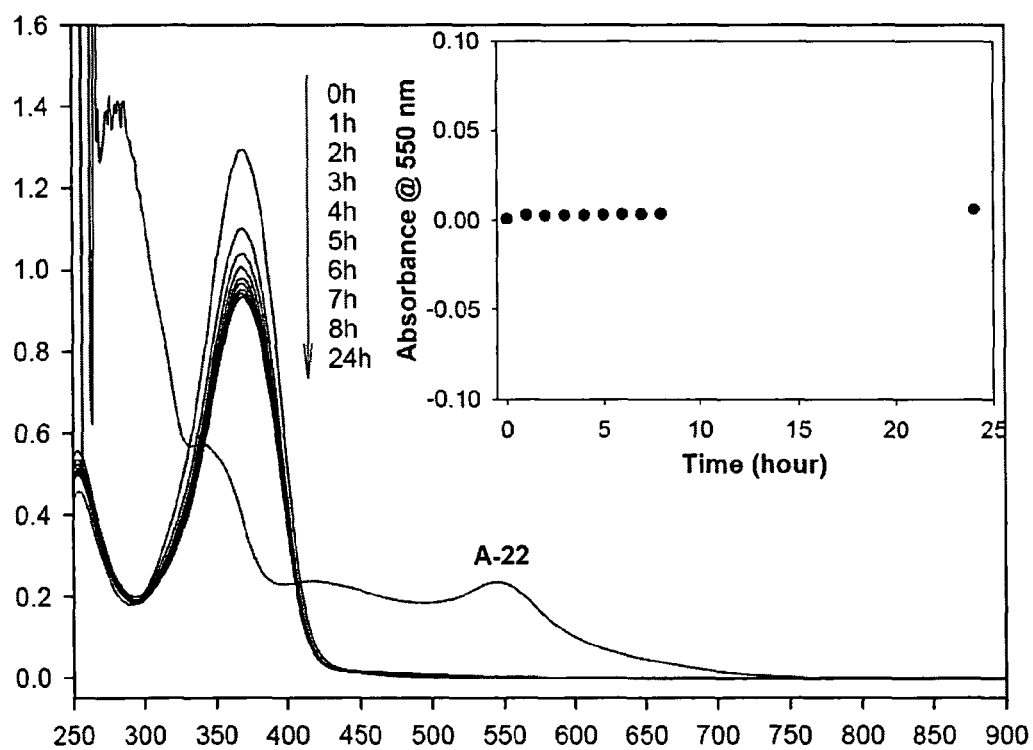
FIG. 15 is a graph of wavelength in units of nm (x axis) versus absorbance of the MeOH dipping solution (y axis). The decrease in the large peak over time is due to the adsorption of the catechol dye A-78 onto the $TiO_2$ substrate. The inset is a graph of absorbance at 550 nm (due to dendrimer A-22) (y axis) versus time in units of hours (x axis); no desorption of A-22 was observed.
Figure 16:
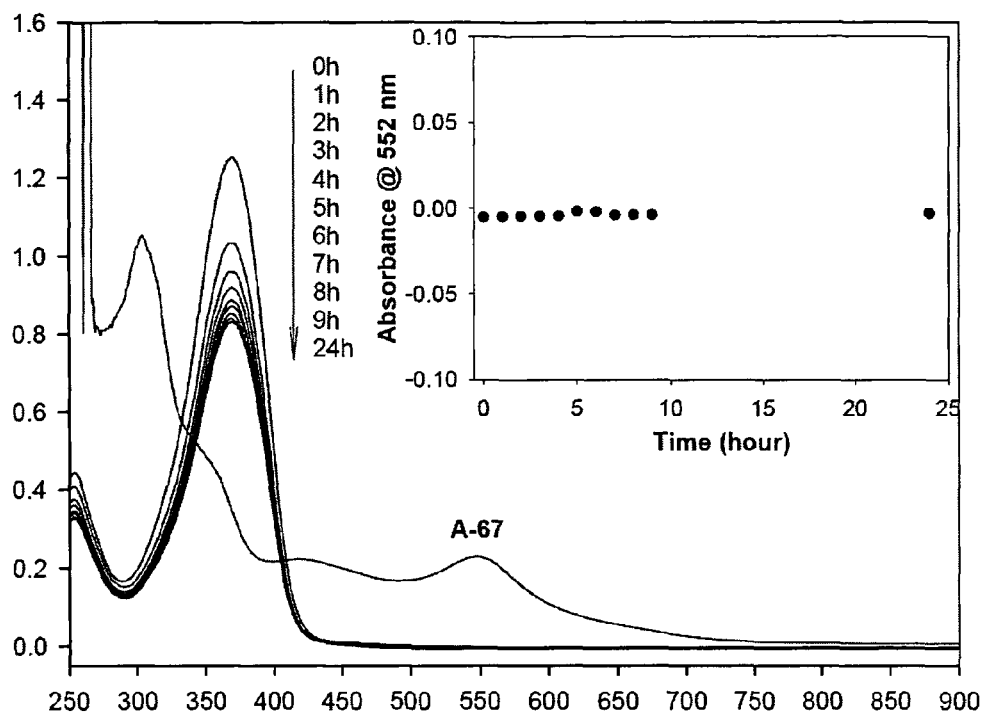
FIG. 16 is a graph of wavelength in units of nm (x axis) versus absorbance of the MeOH dipping solution (y axis). The decrease in the large peak over time is due to the adsorption of the catechol dye A-78 onto the $TiO_2$ substrate. The inset is a graph of absorbance at 552 nm (due to dendrimer A-67) (y axis) versus time in units of hours (x axis); no desorption of A-67 was observed.

(b) Co-Adsorption of the Catechol Dye A-78 Onto Dendrimer- (A-22- and A-67) Adsorbed $TiO_2$ Substrates Unlike the case of N3- and A29-adsorbed $TiO_2$ substrates, A-22 and A-67 molecules were not desorbed from the $TiO_2$ substrates during co-adsorption of A-78 onto the A-22 and A-67-adsorbed $TiO_2$ substrates. This may be due to reduced penetration and contact of MeOH molecules with the surface of $TiO_2$ when A-22 or A-67 molecules are adsorbed. Results are shown in FIGS. 15 and 16. FIG. 15 shows the absorbance change of A-78 in MeOH (5×10$^5$ mol/L) after dipping of an A-22-adsorbed $TiO_2$ substrate for 24 hours at room temperature. FIG. 16 shows the absorbance change of A-78 in MeOH (5×10$^5$ mol/L) after dipping of an A-67-adsorbed $TiO_2$ substrate for 24 hours at room temperature.

Figure 17:
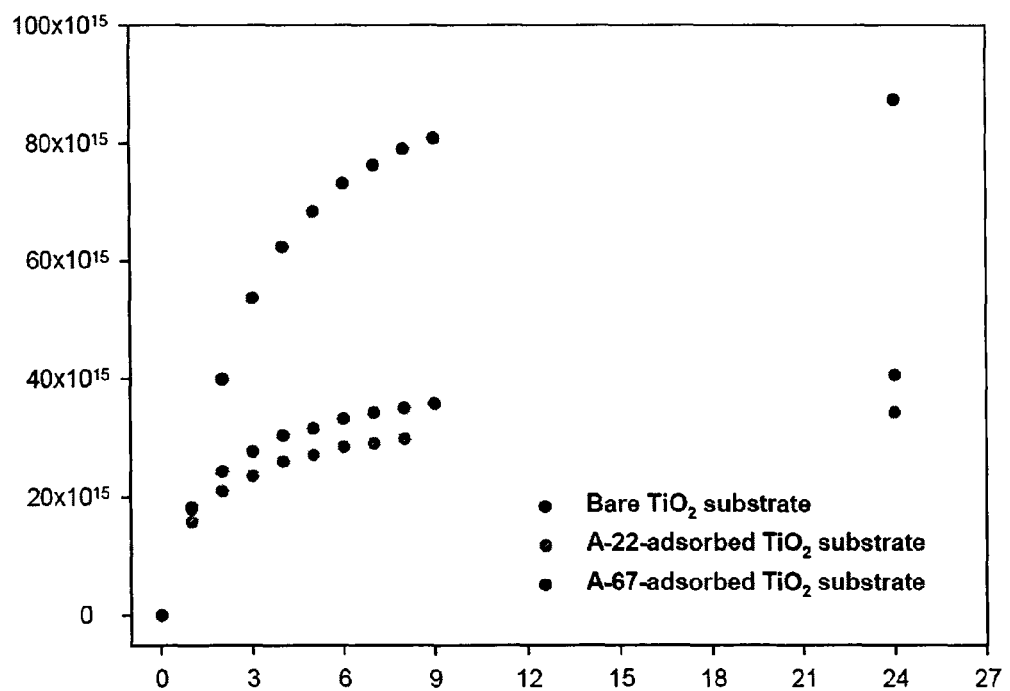
FIG. 17 is a graph of the number of molecules of A-78 adsorbed onto $TiO_2$ in units of $N_A/cm^2$ (y axis) versus time in units of hours (x axis); the uppermost curve shows adsorption onto a bare $TiO_2$ substrate, the middle curve shows adsorption onto an A-67-adsorbed $TiO_2$ substrate and the lower curve shows adsorption onto an A-22-adsorbed $TiO_2$ substrate.

The amounts of the adsorbed A-78 molecules ($N_A$/cm$^2$) onto the A-22-adsorbed $TiO_2$ substrate and onto the A-67-adsorbed $TiO_2$ substrate are 34.4×10$^{15}$ and 40.7×10$^{15}$ respectively. These values are lower than the amount of adsorbed A-78 molecules onto the bare $TiO_2$ substrate ($N_A$/cm$^2$, 88.5×10$^{15}$) (ca. 61% and 54% decrease, respectively). This is shown in FIG. 17, which shows the change in the number of A-78 molecules adsorbed onto the following $TiO_2$ substrates, during dipping of the substrates for 24 hours at room temperature: a bare $TiO_2$ substrate, an A-22-adsorbed substrate and an A-67-adsorbed substrate (all with areas of 0.88 cm$^2$; 0.8 cm×1.1 cm). However, these results show that an additional amount of A-78 dye (ca. 39% and 46%) can be adsorbed onto dendritic Ru dye-adsorbed $TiO_2$ substrates without loss of the Ru dye, and that additional photon-to-electron conversion, by a DTCT process, can be expected.

Figure 18:
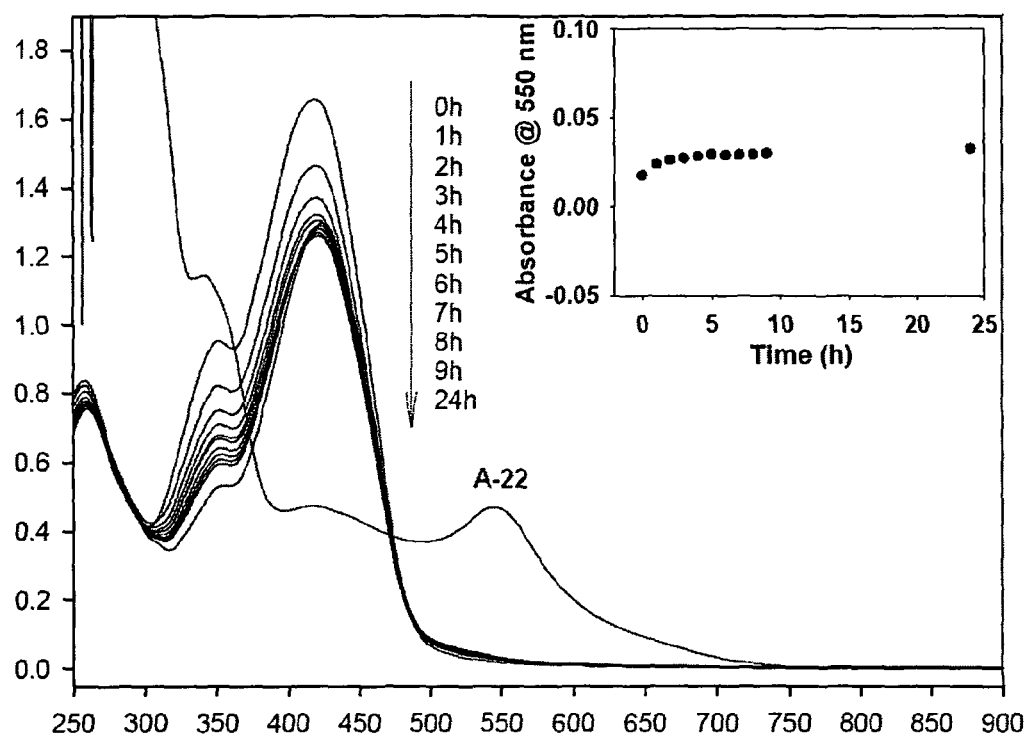
FIG. 18 is a graph of wavelength in units of nm (x axis) versus absorbance of the MeOH dipping solution (y axis). The decrease in the large peak over time is due to the adsorption of the catechol dye A-115 onto the $TiO_2$ substrate. The inset is a graph of absorbance at 550 nm (due to dendrimer A-22) (y axis) versus time in units of hours (x axis); very slight desorption of A-22 was observed.
Figure 19:
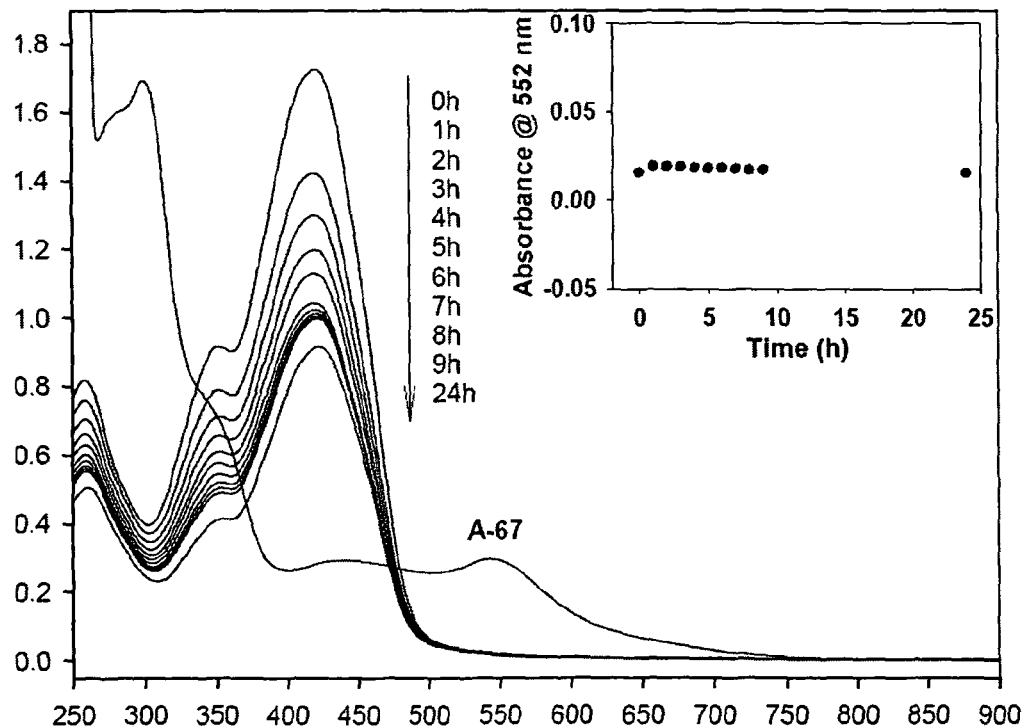
FIG. 19 is a graph of wavelength in units of nm (x axis) versus absorbance of the MeOH dipping solution (y axis). The decrease in the large peak over time is due to the adsorption of the catechol dye A-115 onto the $TiO_2$ substrate. The inset is a graph of absorbance at 552 nm (due to dendrimer A-67) (y axis) versus time in units of hours (x axis); no desorption of A-67 was observed.

(c) Co-Adsorption of the Catechol Dye A-115 Onto Dendrimer- (A-22- and A-67) Adsorbed $TiO_2$ Substrates The A-115 dye, which is expected to have the highest photon-to-current conversion efficiency of the catechol dyes tested, was adsorbed onto A-22-adsorbed $TiO_2$ substrates and A-67-adsorbed $TiO_2$ substrates in order to prepare more optimised photovoltaic devices. A-22- and A-67-adsorbed $TiO_2$ substrates were used, prepared by the best dipping solution; A-22-adsorbed $TiO_2$ substrate: DMF:MeCN=1:1 ($N_A$/cm$^2$=75.1×10$^{15}$), A-67-adsorbed $TiO_2$ substrate: DMF:

MeCN=9:1 ($N_A/cm^2=69.0\times10^{15}$). Unlike the case of co-adsorption of A-78 molecules onto the A-22-adsorbed $TiO_2$ substrates, A-22 molecules were very slightly desorbed from the $TiO_2$ during co-adsorption of A-115 molecules onto A-22-adsorbed $TiO_2$ substrates. This may be because the adsorption power of A-115 molecules is stronger than that of A-78 molecules. These results are shown in FIG. 18, which shows the absorbance change of A-115 in MeOH ($5\times10^{-5}$ mol/L) after dipping of an A-22 adsorbed $TiO_2$ substrate for 24 hours at room temperature. A-67 molecules were not however desorbed from the $TiO_2$ substrates during co-adsorption of A-115 onto the A-67-adsorbed $TiO_2$ substrates (FIG. 19).

Figure 20:
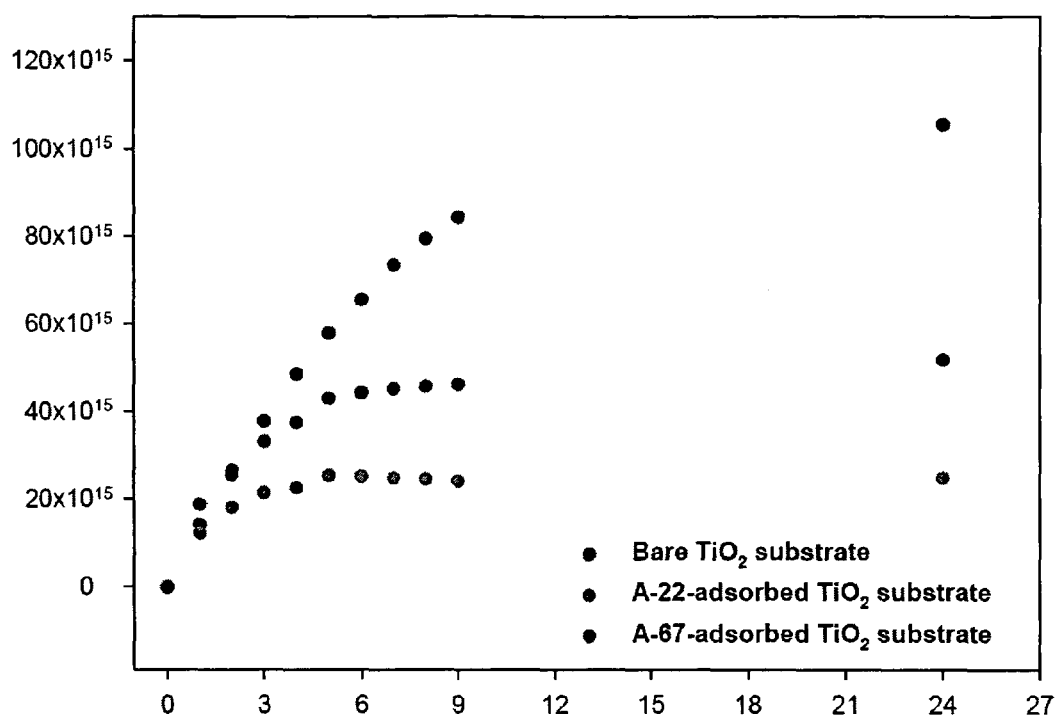
FIG. 20 is a graph of the number of molecules of A-115 adsorbed onto $TiO_2$ in units of $N_A/cm^2$ (y axis) versus time in units of hours (x axis); the uppermost curve shows adsorption onto a bare $TiO_2$ substrate, the middle curve shows adsorption onto an A-67-adsorbed $TiO_2$ substrate and the lower curve shows adsorption onto an A-22-adsorbed $TiO_2$ substrate.

The amounts of the adsorbed A-115 molecules ($N_A/cm^2$) onto the A-22-adsorbed $TiO_2$ substrate and onto the A-67-adsorbed $TiO_2$ substrate are $24.7\times10^{15}$ and $51.5\times10^{15}$ respectively. These values are lower than the amount of adsorbed A-115 molecules onto the bare $TiO_2$ substrate ($N_A/cm^2$, $105.3\times10^{15}$) (ca. 76% and 51% decrease, respectively). This is shown in FIG. 20, which shows the change in the number of A-115 molecules adsorbed onto the following $TiO_2$ substrates, during dipping of the substrates for 24 hours at room temperature: a bare $TiO_2$ substrate, an A-22-adsorbed substrate and an A-67-adsorbed substrate (all with areas of 0.88 $cm^2$; 0.8 cm×1.1 cm). However, these results show that an additional amount of A-115 dye (ca. 24% and 49% respectively) can be adsorbed onto dendritic Ru dye-adsorbed $TiO_2$ substrates without significant loss of the Ru dye, and that additional photon-to-electron conversion, by a DTCT process, can be expected.

(d) Co-Adsorption of Small Ru Dyes Onto the Dendritic A-Series Dye-Adsorbed $TiO_2$ Substrates Grätzel type Ru sensitizers generally show better photon-to-current conversion efficiencies than DTCT sensitizers (e.g. catechol molecules). The conversion efficiency of the dendritic A-series-based photovoltaic devices could be enhanced if small sized Ru sensitizers could be additionally adsorbed onto our dendritic A-series dye-adsorbed $TiO_2$ substrates.

Figure 21:
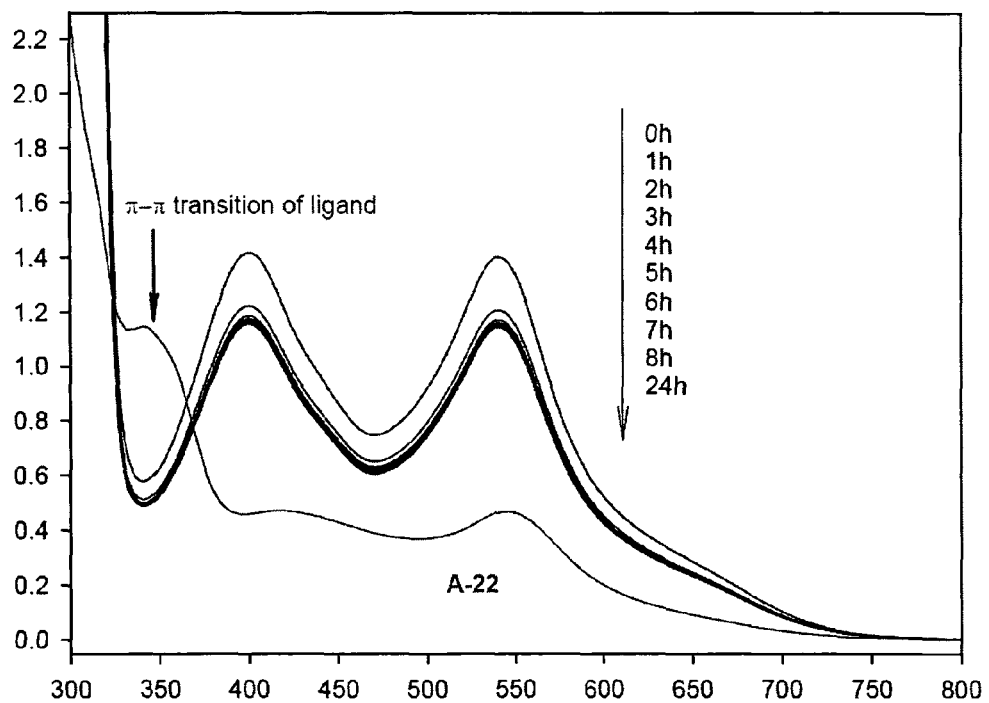
FIG. 21 is a graph of wavelength in units of nm (x axis) versus absorbance of the dipping solution (y axis). The decrease in the large peak over time is due to the adsorption of the N3 dye onto the A-22-adsorbed $TiO_2$ substrate.
Figure 22:
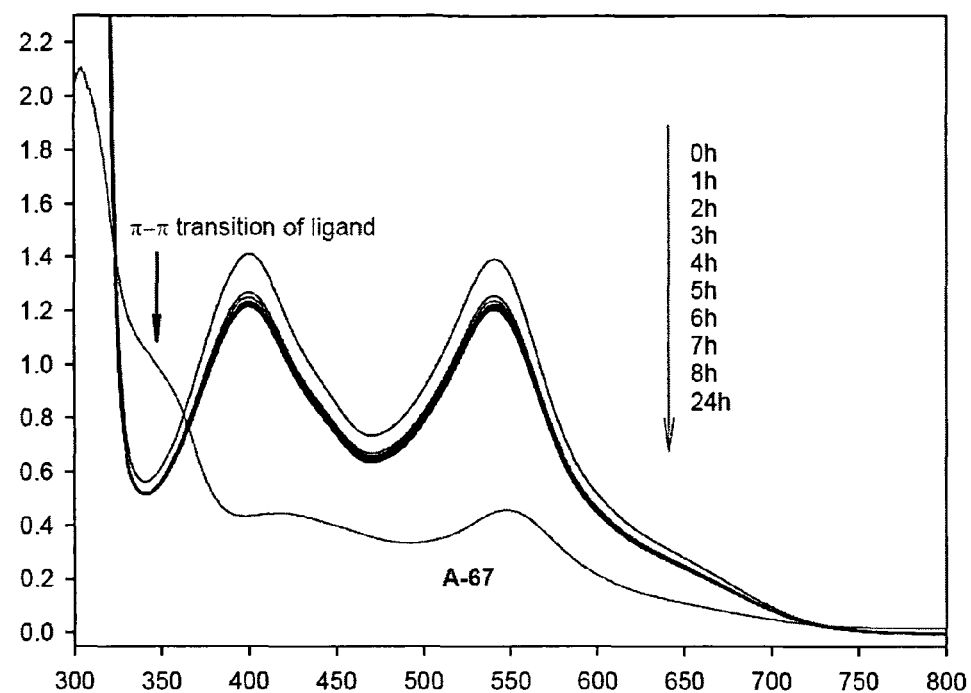
FIG. 22 is a graph of wavelength in units of nm (x axis) versus absorbance of the dipping solution (y axis). The decrease in the large peak over time is due to the adsorption of the N3 dye onto the A-67-adsorbed $TiO_2$ substrate.
Figure 23:
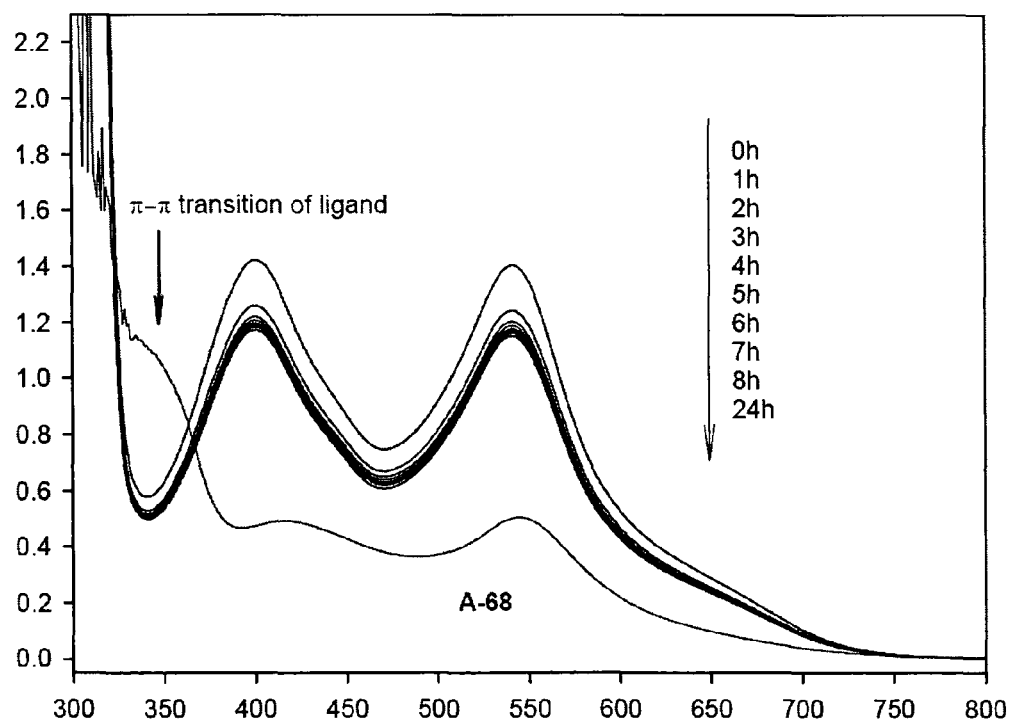
FIG. 23 is a graph of wavelength in units of nm (x axis) versus absorbance of the dipping solution (y axis). The decrease in the large peak over time is due to the adsorption of the N3 dye onto the A-68-adsorbed $TiO_2$ substrate.

A known Ru sensitizer with a high conversion efficiency, N3, was co-adsorbed onto the A-22-, A-67- and A-68-adsorbed $TiO_2$ substrates. The A-22-, A-67- and A-68-adsorbed $TiO_2$ substrates were prepared using a pure DMF dipping solution; A-22-adsorbed $TiO_2$ substrate: DMF ($N_A/cm^2=63.5\times10^{15}$); A-67-adsorbed $TiO_2$ substrate: DMF ($N_A/cm^2=62.8\times10^{15}$); and A-68-adsorbed $TiO_2$ substrate: DMF ($N_A/cm^2=44.4\times10^{15}$). As with co-adsorption of the catechol molecules onto the dendritic Ru dye-adsorbed substrates, the dendritic Ru dyes (A-22, A-67 and A-68) were not desorbed from the $TiO_2$ substrates during co-adsorption of N3 molecules onto the A-22-, A-67- and A-68-adsorbed $TiO_2$ substrates. This can be confirmed by the changes in the absorbance band at 340 nm which is the pi-pi transition band of the dendritic ligands of A-22, A-67 and A-68. A-22, A-67 and A-68 have very high molar coefficients of the pi-pi transition band at 340 nm. The results are shown in FIGS. 21 to 23. FIGS. 21 to 23 show, respectively, the absorbance change of N3 in MeCN:$^t$BuOH (1:1) ($1\times10^4$ mol/L) after dipping of an A-22-adsorbed, an A-67-adsorbed and an A-68-adsorbed $TiO_2$ substrate for 24 hours at room temperature. The numbers ($N_A/cm^2$) of N3 molecules adsorbed onto the A-22-, A-67- and A-68-adsorbed $TiO_2$ are $39.6\times10^{15}$, $29.6\times10^{15}$ and $39.2\times10^{15}$, respectively. These values are lower than the amount of N3 adsorbed onto bare $TiO_2$ ($N_A/cm^2=109.2\times10^{15}$) (ca. 64%, 73% and 64% decrease, respectively). However, these results show that additional amounts of N3 dye (ca. 36%, 27% and 36% respectively) can be adsorbed onto dendritic Ru dye-adsorbed $TiO_2$ substrates without significant loss of the dendritic Ru dye, and that additional photon-to-electron conversion, by the N3, can be expected.

Figure 24:
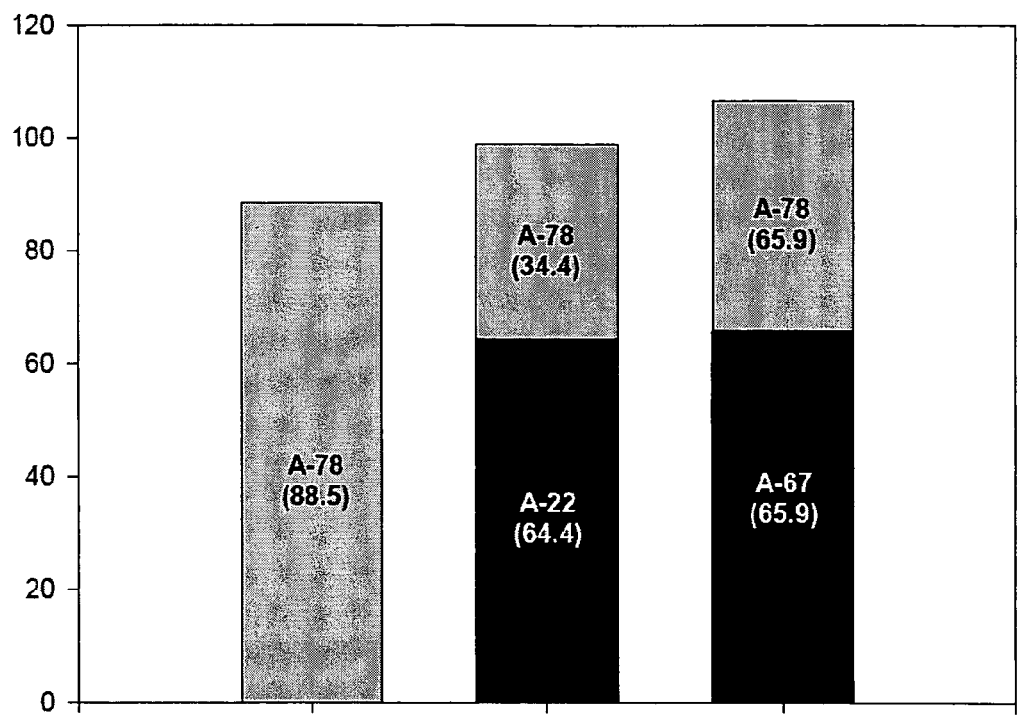
FIG. 24 is a bar chart of the number of dye molecules adsorbed onto $TiO_2$ in units of $\times 10^{15}$ $N_A/cm^2$ (y axis) for (a) A-78 adsorbed onto a bare $TiO_2$ substrate (left hand bar), (b) A-78 adsorbed onto an A-22-adsorbed $TiO_2$ substrate (middle bar), and (c) A-78 adsorbed onto an A-67-adsorbed $TiO_2$ substrate (right hand bar).
Figure 25:
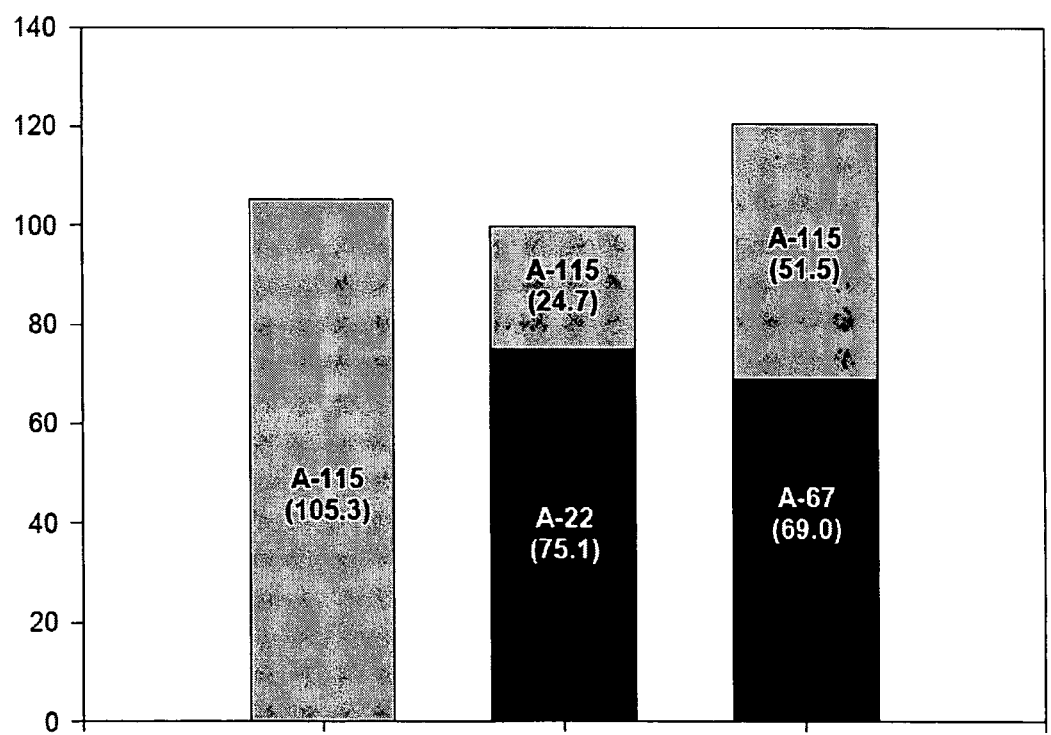
FIG. 25 is a bar chart of the number of dye molecules adsorbed onto $TiO_2$ in units of $\times 10^{15}$ $N_A/cm^2$ (y axis) for (a) A-115 adsorbed onto a bare $TiO_2$ substrate (left hand bar), (b) A-115 adsorbed onto an A-22-adsorbed $TiO_2$ substrate (middle bar), and (c) A-115 adsorbed onto an A-67-adsorbed $TiO_2$ substrate (right hand bar).
Figure 26:
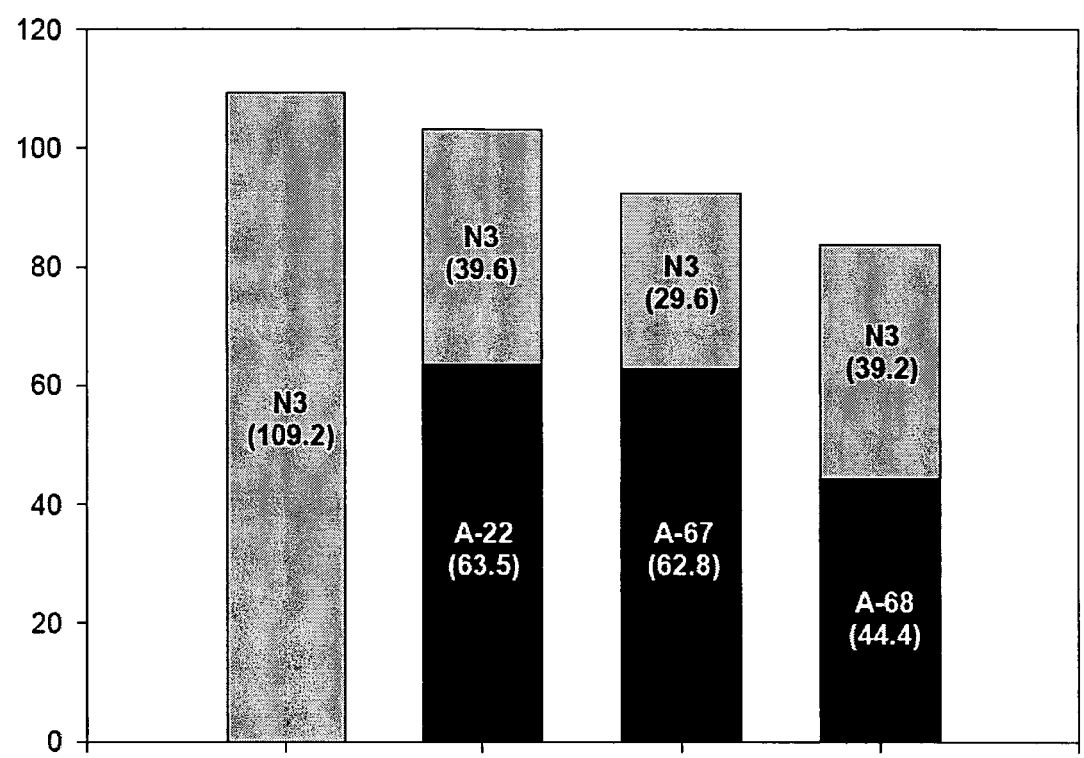
FIG. 26 is a bar chart of the number of dye molecules adsorbed onto $TiO_2$ in units of $\times 10^{15}$ $N_A/cm^2$ (y axis) for (a) N3 adsorbed onto a bare $TiO_2$ substrate (left hand bar), (b) N3 adsorbed onto an A-22-adsorbed $TiO_2$ substrate (bar second from left), (c) N3 adsorbed onto an A-67-adsorbed $TiO_2$ substrate (bar second from right), and (d) N3 adsorbed onto an A-68-adsorbed $TiO_2$ substrate (right hand bar).

In summary, the dendritic hydrophobic Ru sensitizers A-22, A-67 and A-68 are co-adsorbed effectively with catechol dyes (A-78 and A-115) and a small-sized Ru sensitizer (N3) without significant desorption from the $TiO_2$ substrates, whereas the less hydrophobic non-dendritic Ru sensitizers N3 and A-29 were desorbed from the $TiO_2$ substrates during a co-adsorption process. The co-adsorption results of catechol dyes (A-78 and A-115) and the small sized Ru sensitizer (N3) with the dendritic hydrophobic Ru sensitizers (A-22, A-67 and A-68) are summarised in FIGS. 24 to 26. FIG. 24 shows a comparison of the number of A-78 molecules adsorbed onto bare, A-22-adsorbed and A-67 adsorbed $TiO_2$ substrates using an A-78 solution in MeOH ($5\times10^5$ mol/L). FIG. 25 shows a comparison of the number of A-115 molecules adsorbed onto bare, A-22-adsorbed and A-67 adsorbed $TiO_2$ substrates using an A-115 solution in MeOH ($5\times10^5$ mol/L). FIG. 26 shows a comparison of the number of N3 molecules adsorbed onto bare, A-22-adsorbed and A-67 adsorbed $TiO_2$ substrates using an N3 solution in MeOH:$^t$BuOH (1:1) ($1\times10^4$ mol/L). It can be expected that the A-78 and A-115 dyes co-adsorbed with Ru dyes on $TiO_2$ substrates will have a higher conversion efficiency than A-78 or A-115 alone on $TiO_2$. The total co-adsorbed amount of N3 and dendritic dye is smaller than the amount of N3 dye on the 'N3-only' $TiO_2$ substrate. However, it can be expected that the co-adsorbed $TiO_2$ substrates will have a higher conversion efficiency of MLCT than the substrates adsorbed with N3 only because the molar extinction coefficient of MLCT of A-22, A-67 and A-68 is, respectively, 1.46, 1.55 and 1.63 times greater than that of N3.

Example 8

Synthesis of dendrimer L01

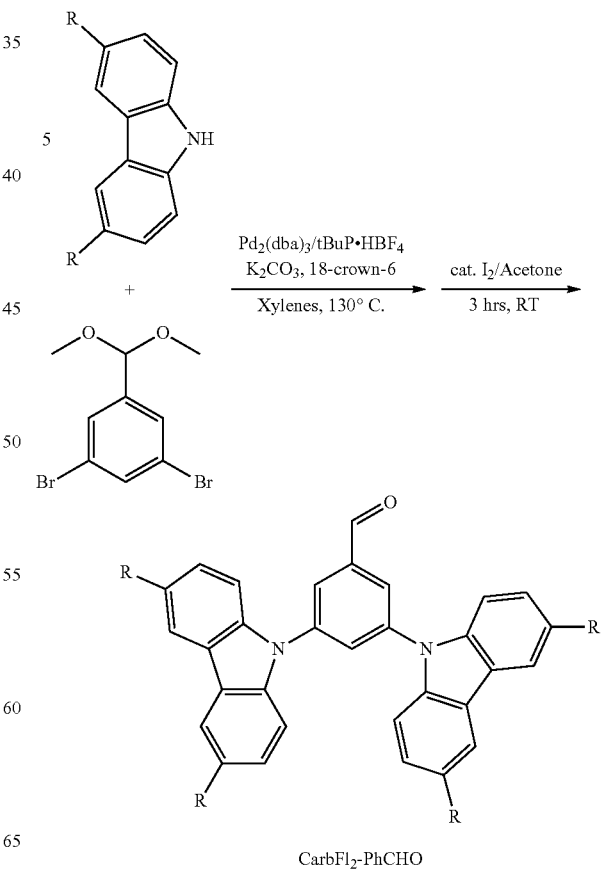

CarbFl$_2$-PhCHO

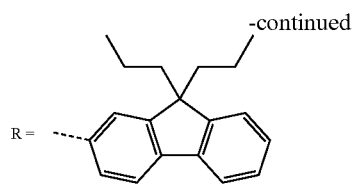

(i) Step 1—Preparation of CarbFl$_2$-PhCHO

To a dry 25 mL Schlenk tube was added 1,3-dibromo-5-(dimethoxymethyl)benzene (150 mg; 0.484 mmol), 3,5-bis(3,6-bis(9,9-di-n-propylfluoren-2-yl)carbazole (prepared according to reference *J. Mater. Chem.* 2008, 18, 2121; 706 mg; 1.06 mmol), tris(dibenzylideneacetone)dipalladium(0) (41.3 mg, 0.04 mmol), tri(tert-butyl)phosphonium tetrafluoroborate (46.7 mg; 0.16 mmol), anhydrous potassium carbonate (398 mg; 2.88 mmol) and 18-crown-6 (29 mg; 0.11 mmol). This mixture was degassed under vacuum then backfilled with argon then xylenes (3 mL) were added under argon flow. The resulting solution was degassed with 3 pump/fill cycles then heated at 130° C. and stirred overnight. The reaction was cooled to room temperature then the reaction mixture was filtered through Celite. The solvent was removed by rotary evaporation then the crude product was purified by column chromatography, eluted with 1:9 ethyl acetate in light petrol. The first fraction was collected and the solvent removed. The residue was dissolved in acetone (30 mL) with iodine (100 mg; 0.4 mmol). This mixture was stirred at room temperature for 3 hours before the acetone was removed, the crude product dissolved in dichloromethane (20 mL) then washed with 5% w/w aqueous sodium thiosulfate (10 mL), water (10 mL) and brine (10 mL), dried over anhydrous magnesium sulfate then concentrated to leave CarbFl$_2$-PhCHO as a yellow solid (498 mg; 72%). $^1$H NMR (500 MHz, CDCl$_3$) δ 10.32 (s, 1H, CHO), 8.55 (s, 4H, Cbz), 8.37 (s, 2H, Ph), 8.29 (s, 1H, Ph), 7.86 (d, $^3J$=8.5, 4H, Cbz), 7.83 (d, $^3J$=7.7, 4H, Fl), 7.76 (d, $^3J$=7.8, 4H, Fl), 7.73 (d, $^3J$=8.3, 4H, Cbz), 7.73 (s, 4H, Fl), 7.41-7.33 (m, 12H, Fl), 2.12-2.01 (m, 16H, Pr), 0.84-0.75 (m, 8H, Pr), 0.73-0.70 (m, 12H, Pr). MS (MALDI-TOF) Found 1428.54, Calc. 1428.78.

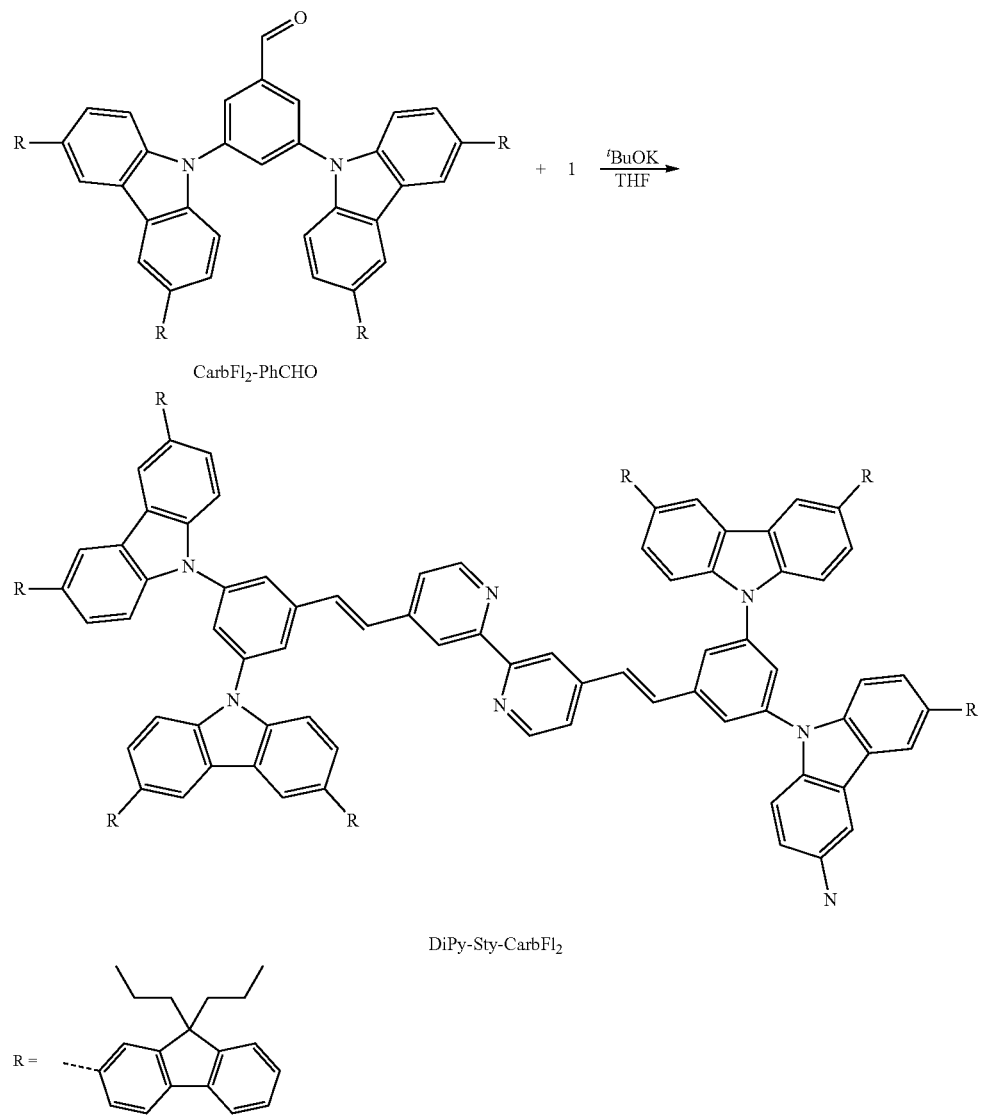

(ii) Step 2—Preparation of DiPy-Sty-CarbFl$_2$

To a mixture of CarbFl2-PhCHO (260 mg; 0.18 mmol), 1 (35 mg; 0.091 mmol) in THF (4 mL) was added dropwise a solution of potassium tert-butoxide (31 mg; 0.27 mmol) in THF (1 mL). The resulting brown solution was stirred at room temperature for 3 hours. After this time the reaction was quenched with water (10 mL) then the reaction mixture was concentrated by rotary evaporation. The pale brown suspension was filtered, then the precipitate was washed with water (25 mL) and the crude product recrystallised by slow evaporation of a dichloromethane/hexane mixture to afford DiPy-Sty-CarbFl$_2$ as a microcrystalline yellow powder (218 mg; 80%). MS (MALDI-TOF) Found 3005.6, Calc. 3005.6. $v_{max}$ 3056 (Aromatic C—H); 2953, 2928, 2868 (Alkyl C—H); 1587 (Cbz C—N); 1465, 1446 (Aromatic C=C); 960 (trans-alkene C—H). $\lambda_{max}$ (nm, log $\epsilon$) 324, 5.57; 273, 5.24.

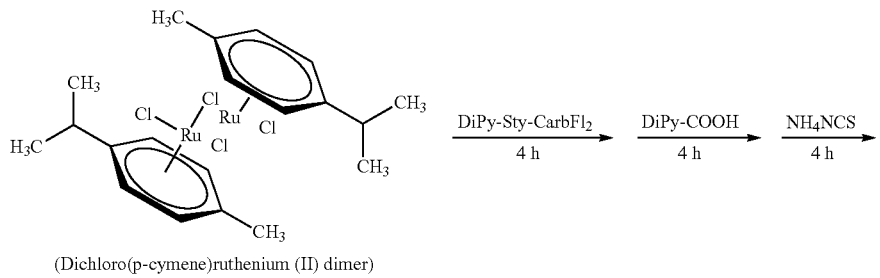

(Dichloro(p-cymene)ruthenium (II) dimer)

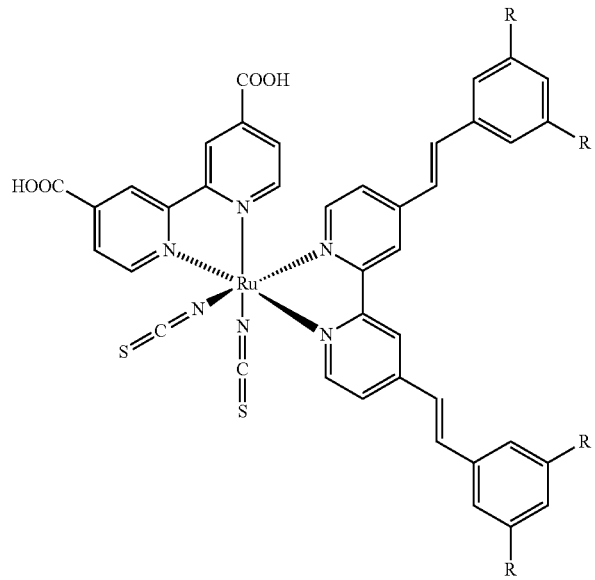

L01

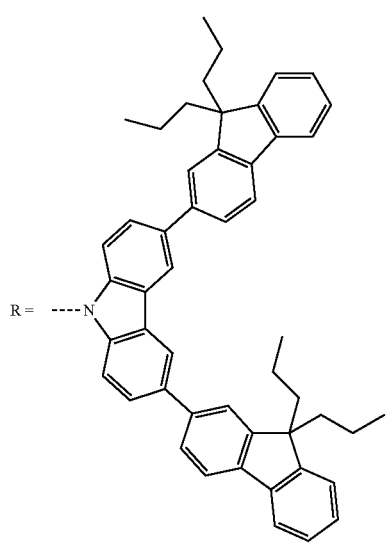

(iii) Step 3—Preparation of Dendrimer L01

To a dry, light-excluded 10 ml flask fitted with a condenser was added N,N-dimethylformamide (3 mL), Ru(II)(p-cymene)Cl$_2$ dimer (5.1 mg; 0.008 mmol) and DiPy-Sty-CarbFl$_2$ (50 mg; 0.016 mmol). The system was purged with argon before being heated to 80° C. with stirring for 4 hours. After this time 2,2'-bipyridine-4,4'-dicarboxylic acid (4.1 mg; 0.016 mmol) was added and the reaction was heated to 150° C. for 4 hours. Ammonium thiocyanate (31.6 mg; 0.42 mmol) was then added and the reaction stirred for a further 4 hours. After this time the resulting purple solution was cooled to room temperature, then the bulk of the reaction solvent was removed by rotary evaporation before water (10 mL) was added. The crude product was purified by size exclusion chromatography over Sephadex LH-20 beads swollen in dichloromethane and eluted with dichloromethane. The main purple band was collected to give 37 mg of dark purple powder. $^1$H-NMR (400 MHz, CDCl$_3$) δ (ppm) 8.44 (s, 8H); 8.14 (s, 2H); 8.01 (s, 4H); 7.79-7.10 (m, br, 56H); 1.93-1.89 (m, 32H); 0.7-0.2 (m, 80H). $\lambda_{max}$ (nm, log ε) 549, 4.02; 324, 5.58, 273, 5.22.

The invention claimed is:

1. A dye-sensitized photovoltaic device which comprises: a first electrode; a second electrode; and, disposed between the first and second electrodes:
    (a) an electron acceptor material which comprises a semiconductive metal oxide;
    (b) a redox mediator material; and
    (c) a photosensitizing dye which comprises a dendrimer of formula (V):

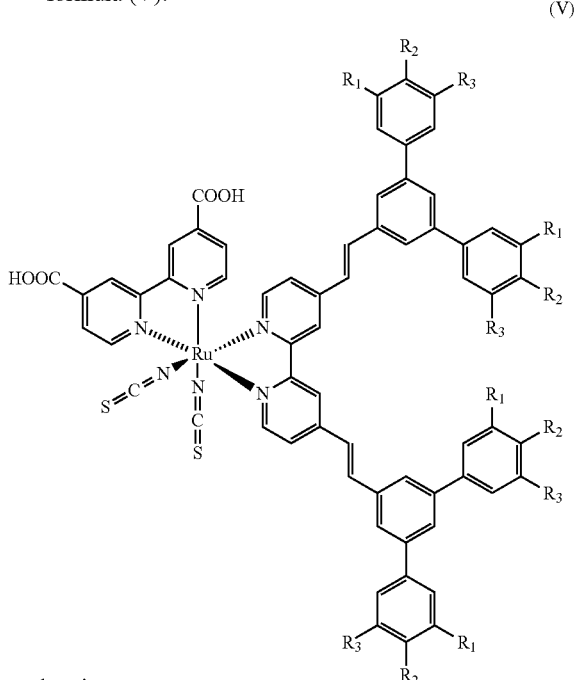

(V)

wherein:
(a) R$_2$ is —O-2-ethylhexyl and R$_3$ are both H;
(b) R$_1$ and R$_2$ are both —O-2-ethylhexyl and R$_3$ is H; or
(c) R$_1$, R$_2$ and R$_3$ are each —O-2-ethylhexl.

2. A dye-sensitized photovoltaic device according to claim 1 which further comprises a second photosensitizing dye attached to said semiconductive metal oxide, which second photosensitizing dye is other than said dendrimer of formula (V).

3. A dye-sensitized photovoltaic device according to claim 2 wherein the second photosensitizing dye is benzene-1,2-diol which is either unsubstituted or substituted in the 3, 4, 5 or 6 position with a group of formula (VI):

-G-[J]$_j$-R"        (Vi)

wherein

G is unsubstituted or substituted C$_{2-6}$ alkenylene;

j is an integer of 1 to 5;

each J, which is the same or different, is an unsubstituted or substituted heteroarylene group, or an unsubstituted or substituted arylene group; and R" is H, C$_{1-15}$ alkyl or DENDRON, wherein DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and C$_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

4. A dye-sensitized photovoltaic device according to claim 2 wherein the second photosensitizing dye is a compound of formula (VII):

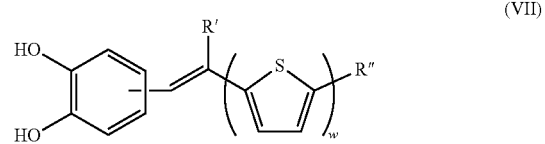

(VII)

wherein R' is H or CN; w is an integer of 1 to 5; and R" is H, C$_{1-15}$ alkyl or DENDRON, wherein DENDRON represents an at least partially conjugated dendritic molecular structure comprising at least one branching group and optionally at least one linking group, the branching groups being selected from aryl groups and heteroaryl groups, and the linking groups being selected from aryl, heteroaryl, vinyl, acetylenyl and C$_{1-15}$ alkyleneoxy groups, said branching groups being bonded to three or more groups, and said linking groups being bonded to two groups, said dendritic molecular structure terminating at its distal points in terminal aryl and/or heteroaryl groups, wherein each of said terminal aryl and/or heteroaryl groups is independently either unsubstituted or substituted with one, two, three or four surface groups.

5. A dye-sensitized photovoltaic device according to claim 2 wherein the second photosensitizing dye is a heteroleptic Ru(II) complex.

6. A dye-sensitized photovoltaic device according to claim 2 wherein the second photosensitizing dye is any one of the following compounds:

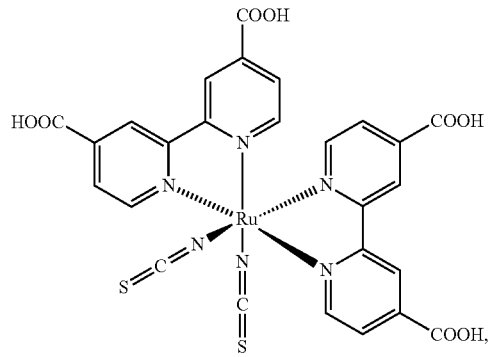

-continued

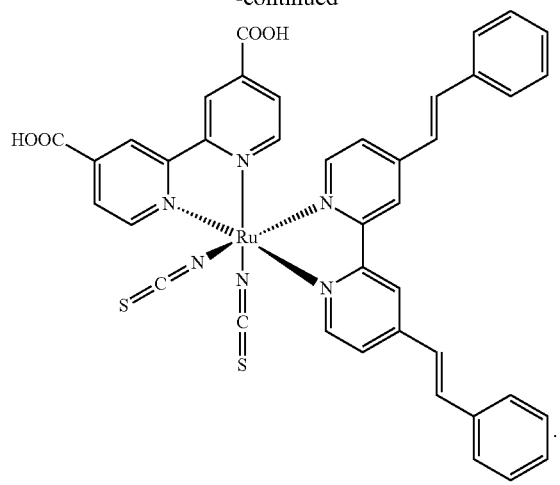

7. A dye-sensitized photovoltaic device according to claim 2 which further comprises a third photosensitizing dye attached to said semiconductive metal oxide, which third photosensitizing dye is a compound.

8. A dye-sensitized photovoltaic device according to claim 1 wherein the semiconductive metal oxide is titania.

9. A compound which is a dendrimer of formula (V):

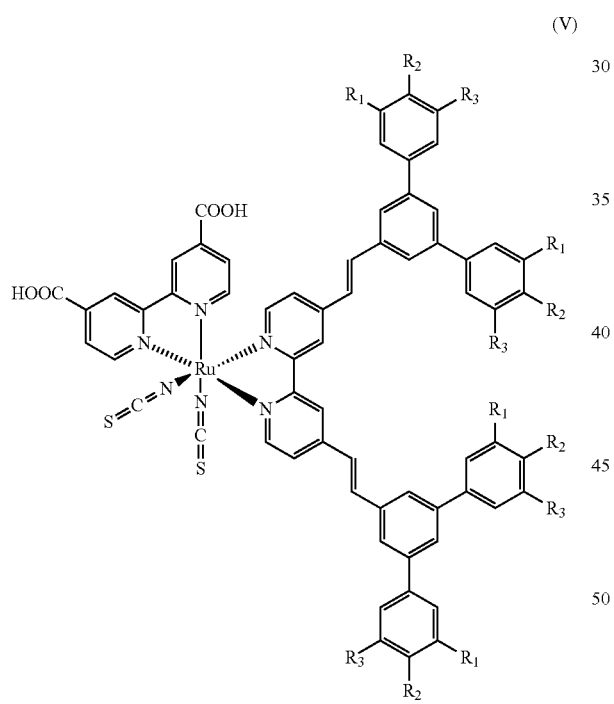

(V)

wherein:
(a) $R_2$ is —O-2-ethylhexyl and $R_1$ and $R_3$ are both H;
(b) $R_1$ and $R_2$ are both —O-2-ethylhexyl and $R_3$ is H; or
(c) $R_1$, $R_2$ and $R_3$ are each —O-2-ethylhexyl.

10. A method of use comprising:
selecting a compound which is a dendrimer of formula (V):

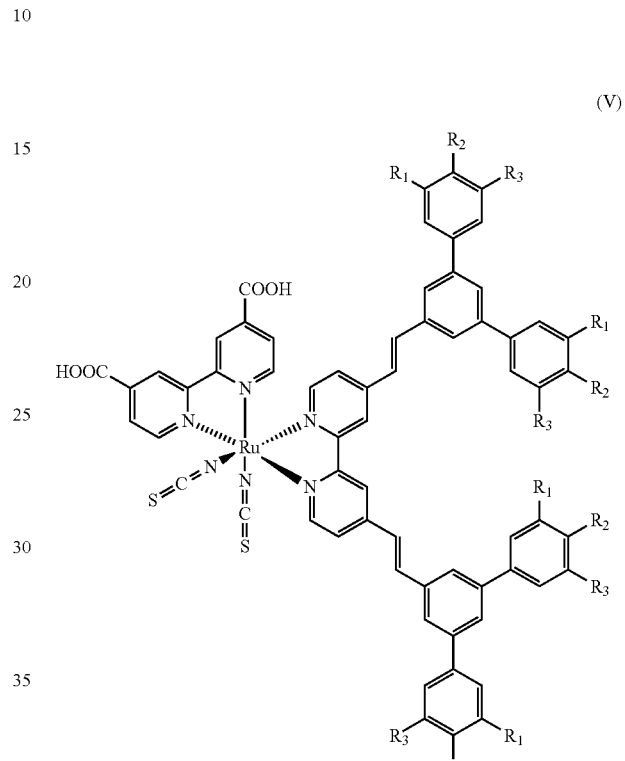

(V)

wherein:
(a) $R_2$ is —O—2-ethylhexyl and $R_1$ and $R_3$ are both H;
(b) $R_1$ and $R_2$ are both —O-2-ethylhexyl and $R_3$ H; or
(c) $R_1$, $R_2$ and $R_3$ are each —O-2-ethylhexyl, and using the compound as a photosensitizing dye in a dye sensitized photovoltaic device.

11. A photosensitizing dye which comprises a dendrimer as defined in claim 1.

* * * * *